(12) United States Patent
Pan et al.

(10) Patent No.: US 11,555,077 B2
(45) Date of Patent: Jan. 17, 2023

(54) 4-1BB ANTIBODY AND PREPARATION METHOD AND USE THEREOF

(71) Applicant: SHANGHAI HYAMAB BIOTECH CO., LTD., Shanghai (CN)

(72) Inventors: Heng Pan, Shanghai (CN); Haohan Liu, Shanghai (CN); Yingying Gao, Shanghai (CN); Shaoping Hu, Shanghai (CN); Yong Li, Shanghai (CN); Mingming Pan, Shanghai (CN); Tatchi Teddy Yang, Shanghai (CN); Qing Duan, Shanghai (CN); Lile Liu, Shanghai (CN)

(73) Assignee: Shanghai Hyamab Biotech Co., Ltd., Shanghai (CN)

( * ) Notice: Subject to any disclaimer, the term of this patent is extended or adjusted under 35 U.S.C. 154(b) by 177 days.

(21) Appl. No.: 16/762,871

(22) PCT Filed: Nov. 8, 2018

(86) PCT No.: PCT/CN2018/114641
§ 371 (c)(1),
(2) Date: Jun. 11, 2020

(87) PCT Pub. No.: WO2019/091436
PCT Pub. Date: May 16, 2019

(65) Prior Publication Data
US 2020/0347144 A1 Nov. 5, 2020

(30) Foreign Application Priority Data
Nov. 9, 2017 (CN) .......................... 201711099446.4

(51) Int. Cl.
*C07K 16/28* (2006.01)
*A61P 35/00* (2006.01)

(52) U.S. Cl.
CPC .......... *C07K 16/2878* (2013.01); *A61P 35/00* (2018.01); *C07K 2317/24* (2013.01);
(Continued)

(58) Field of Classification Search
None
See application file for complete search history.

(56) References Cited

U.S. PATENT DOCUMENTS 6,303,121 B1 10/2001 Kwon
7,288,638 B2 10/2007 Jure-Kunkel et al.
(Continued)

FOREIGN PATENT DOCUMENTS

AR      046094 A1    11/2005
CN     1289668 C    12/2006
(Continued)

OTHER PUBLICATIONS

Chester et al., Immunotherapy targeting 4-1BB: mechanistic rationale, clinical results, and future strategies, Blood, 131(1):49-57, 2018.*
(Continued)

*Primary Examiner* — Claire Kaufman
(74) *Attorney, Agent, or Firm* — Polsinelli PC

(57) ABSTRACT

Provided in the present invention are a 4-1BB antibody and a preparation method and the use thereof. In particular, provided in the present invention are a 4-1BB antibody, which has high affinity to 4-1BB protein, can effectively activate the signal downstream of the 4-1BB and significantly increase expression quantities of IFN-γ and IL-2 in human mixed lymphocytes or T lymphocytes, and can be used to treat cancers and autoimmune diseases.

12 Claims, 12 Drawing Sheets
Specification includes a Sequence Listing.

(52) U.S. Cl.
   CPC .............. *C07K 2317/565* (2013.01); *C07K 2317/622* (2013.01); *C07K 2319/33* (2013.01)

(56) References Cited

U.S. PATENT DOCUMENTS

| | | | |
|---|---|---|---|
| 2017/0226215 A1* | 8/2017 | Gray | A61P 13/12 |
| 2018/0282422 A1* | 10/2018 | Xu | A61K 39/395 |

FOREIGN PATENT DOCUMENTS

| | | |
|---|---|---|
| CN | 101628940 B | 11/2011 |
| CN | 106199005 B | 2/2019 |
| ES | 2866202 T3 | 10/2021 |
| WO | 96/32495 E | 10/1996 |
| WO | 2012032433 A1 | 3/2012 |
| WO | 2016134358 A1 | 8/2016 |

OTHER PUBLICATIONS

MacCallum et al., Antibody-antigen interactions: contact analysis and binding site topography, J. Mol. Biol. 262:732-745, 1996.*

Chen et al., Enhancement and destruction of antibody function by somatic mutation: unequal occurrence is controlled by V gene combinatorial associations, EMBO J. 14(12):2784-2794, 1995.*

Lamminmaki et al., Chrystal structure of a recombinant anti-estradiol Fab fragment in complex with the 17beta-estradiol, J. Biol. Chem. 276:36687-94, 2001.*

Kranz et al., REstricted reassociation of heavy and light chains from paten-specific monclonal antibodies. Proc. Natl. Aacad. Sci. USA, 78(9) 5807-5811, Sep. 1981.*

Nezlin, RS. Biochemistry of Antibodies, Plenum Press:New York, p. 160, 1970.*

Herold et al., Determinants of the assembly and function of antibody variable domains,Scientific Reports, 7:12276, DOI:10.1038/s41598-017-12519-9, Sep. 2017.*

Sela-Culang et al. , The structural basis of antibody-antigen recognition, Frontiers in Immunology, vol. 4, Article 302, doi: 10.3389/fimmu.2013.00302, Oct. 2013..*

English abstract for CN1289668; retrieved from www.espacenet.com on May 2, 2022.

English abstract for AR046094; retrieved from www.espacenet.com on May 2, 2022.

English abstract for CN101628940; retrieved from www.espacenet.com on May 2, 2022.

English abstract for ES2866202; retrieved from www.espacenet.com on May 2, 2022.

English abstract for CN106199005; retrieved from www.espacenet.com on May 2, 2022.

Larson, Rebecca C. et al.: "After two decades of fine-tuning Tcell engineering", Nature Reviews, vol. 21, Jan. 22, 2021 (Jan. 22, 2021), pp. 145-161, XP055801557, Retrieved from the Internet <URL:https://www.nature.com/articles/s41568-020-00323-z.pdf>.

Fisher, Timothy S. et al.: "Targeting of 4-1BB by monoclonal antibody PF-05082566 enhances T-cell function and promotes anti-tumor activity", Cancer Immunology, Immunotherapy, vol. 61, No. 10, Mar. 11, 2012 (Mar. 11, 2012), Berlin/Heidelberg, pp. 1721-1733, XP055391951, ISSN: 0340-7004, DOI: 10.1007/s00262-012-1237-1.

Kipriyanov et al., "Two amino acid mutations in an anti-human CD3 single chain Fv antibody fragment that affect the yield on bacterial secretion but not the affinity", PEDS, vol. 10, Apr. 1997, pp. 445-453. Abstract only.

Tian, Xiaojing: "Preparation of Anti-human 4-1BB monoclonal antibody and analysis of its biological functions", Current Immunologya, vol. 27, No. 3, Dec. 31, 2007 (Dec. 31, 2007), pp. 202-206, XP009520974, ISSN: 1001-2478.

Zhou, Huan et al.: "Preparation of Anti-human 4-1BB monoclonal antibody and characterization of its biological activities", Chineses Journal of Cellular and Molecular Immunology, vol. 27, No. 9, Dec. 31, 2011 (Dec. 31, 2011), pp. 993-996, XP009520975, DOI: 10.13423/j.cnki.cjcmi.006137.

* cited by examiner

SEQUENCE LISTING

<160> NUMBER OF SEQ ID NOS: 140

<210> SEQ ID NO 1
<211> LENGTH: 125
<212> TYPE: PRT
<213> ORGANISM: Artificial Sequence
<220> FEATURE:
<223> OTHER INFORMATION: the heavy chain variable region

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Thr Ser Val Thr Ala Ala Asp Thr Ala Val Tyr Tyr Cys Ala
                85                  90                  95

Lys Asp Ser Asp Tyr Tyr Gly Ser Gly Ser Tyr Ser Tyr Trp Tyr Phe
            100                 105                 110

Asp Leu Trp Gly Arg Gly Thr Leu Val Thr Val Ser Ser
        115                 120                 125
```

<210> SEQ ID NO 2
<211> LENGTH: 5
<212> TYPE: PRT
<213> ORGANISM: Artificial Sequence
<220> FEATURE:
<223> OTHER INFORMATION: CDR1

<400> SEQUENCE: 2

```
Ser Tyr Tyr Trp Ser
1               5
```

<210> SEQ ID NO 3
<211> LENGTH: 16
<212> TYPE: PRT
<213> ORGANISM: Artificial Sequence
<220> FEATURE:
<223> OTHER INFORMATION: CDR2

<400> SEQUENCE: 3

```
Tyr Ile Tyr Tyr Ser Gly Ser Thr Asn Tyr Asn Pro Ser Leu Lys Ser
1               5                   10                  15
```

<210> SEQ ID NO 4
<211> LENGTH: 17
<212> TYPE: PRT
<213> ORGANISM: Artificial Sequence
<220> FEATURE:
<223> OTHER INFORMATION: CDR3

<400> SEQUENCE: 4

```
Asp Ser Asp Tyr Tyr Gly Ser Gly Ser Tyr Ser Tyr Trp Tyr Phe Asp
1               5                   10                  15

Leu
```

```
<210> SEQ ID NO 5
<211> LENGTH: 107
<212> TYPE: PRT
<213> ORGANISM: Artificial Sequence
<220> FEATURE:
<223> OTHER INFORMATION: the light chain variable region

<400> SEQUENCE: 5

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Pro Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: CDR1??

<400> SEQUENCE: 6

Arg Ala Ser Gln Ser Val Ser Ser Asn Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR2'

<400> SEQUENCE: 7

Gly Ala Ser Thr Arg Ala Pro
1               5

<210> SEQ ID NO 8
<211> LENGTH: 9
<212> TYPE: PRT
<213> ORGANISM: Artificial Sequence
<220> FEATURE:
<223> OTHER INFORMATION: CDR3'

<400> SEQUENCE: 8

Gln Gln Tyr Asn Asn Trp Pro Leu Thr
1               5

<210> SEQ ID NO 9
<211> LENGTH: 128
<212> TYPE: PRT
<213> ORGANISM: Artificial Sequence
<220> FEATURE:
<223> OTHER INFORMATION: the heavy chain variable region
```

<400> SEQUENCE: 9

```
Gln Val Gln Leu Val Glu Ser Gly Gly Val Val Gln Pro Gly Arg
1               5                   10                  15

Ser Leu Arg Leu Ser Cys Ala Ala Ser Gly Leu Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Val Leu Trp Phe Gly Glu Leu Ser Tyr Asn Tyr Tyr
            100                 105                 110

Tyr Gly Met Asp Val Trp Gly Gln Gly Thr Thr Val Thr Val Ser Ser
        115                 120                 125
```

<210> SEQ ID NO 10
<211> LENGTH: 5
<212> TYPE: PRT
<213> ORGANISM: Artificial Sequence
<220> FEATURE:
<223> OTHER INFORMATION: CDR1

<400> SEQUENCE: 10

```
Ser Tyr Gly Met His
1               5
```

<210> SEQ ID NO 11
<211> LENGTH: 17
<212> TYPE: PRT
<213> ORGANISM: Artificial Sequence
<220> FEATURE:
<223> OTHER INFORMATION: CDR2

<400> SEQUENCE: 11

```
Val Ile Trp Tyr Asp Gly Ser Asn Lys Tyr Tyr Ala Asp Ser Val Lys
1               5                   10                  15

Gly
```

<210> SEQ ID NO 12
<211> LENGTH: 19
<212> TYPE: PRT
<213> ORGANISM: Artificial Sequence
<220> FEATURE:
<223> OTHER INFORMATION: CDR3

<400> SEQUENCE: 12

```
Glu Glu Val Leu Trp Phe Gly Glu Leu Ser Tyr Asn Tyr Tyr Tyr Gly
1               5                   10                  15

Met Asp Val
```

<210> SEQ ID NO 13
<211> LENGTH: 107
<212> TYPE: PRT
<213> ORGANISM: Artificial Sequence
<220> FEATURE:
<223> OTHER INFORMATION: the light chain variable region

```
<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Val Pro Leu
                85                  90                  95

Thr Phe Gly Gly Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: CDR1??

<400> SEQUENCE: 14

Arg Ala Ser Gln Gly Ile Ser Asn Tyr Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: CDR2??

<400> SEQUENCE: 15

Ala Ala Ser Thr Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: CDR3??

<400> SEQUENCE: 16

Gln Lys Tyr Asn Ser Val Pro Leu Thr
1               5

<210> SEQ ID NO 17
<211> LENGTH: 120
<212> TYPE: PRT
<213> ORGANISM: Artificial Sequence
<220> FEATURE:
<223> OTHER INFORMATION: the light chain variable region

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Ala Met His Trp Val Arg Gln Ala Pro Gly Lys Gly Leu Glu Trp Val
        35                  40                  45

Ala Ile Ile Trp Tyr Asp Gly Ser Asn Gln Tyr Tyr Ala Asp Ser Val
    50                  55                  60

Lys Gly Arg Phe Thr Ile Ser Arg Asp Asn Ser Met Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Glu Gln Trp Leu Val Ser Tyr Phe Asp Phe Trp Gly Gln
            100                 105                 110

Gly Thr Leu Val Thr Val Ser Ser
        115                 120

<210> SEQ ID NO 18
<211> LENGTH: 5
<212> TYPE: PRT
<213> ORGANISM: Artificial Sequence
<220> FEATURE:
<223> OTHER INFORMATION: CDR1

<400> SEQUENCE: 18

Ser Tyr Ala Met His
1               5

<210> SEQ ID NO 19
<211> LENGTH: 17
<212> TYPE: PRT
<213> ORGANISM: Artificial Sequence
<220> FEATURE:
<223> OTHER INFORMATION: CDR2

<400> SEQUENCE: 19

Ile Ile Trp Tyr Asp Gly Ser Asn Gln Tyr Tyr Ala Asp Ser Val Lys
1               5                   10                  15

Gly

<210> SEQ ID NO 20
<211> LENGTH: 11
<212> TYPE: PRT
<213> ORGANISM: Artificial Sequence
<220> FEATURE:
<223> OTHER INFORMATION: CDR3

<400> SEQUENCE: 20

Val Glu Gln Trp Leu Val Ser Tyr Phe Asp Phe
1               5                   10

<210> SEQ ID NO 21
<211> LENGTH: 106
<212> TYPE: PRT
<213> ORGANISM: Artificial Sequence
<220> FEATURE:
<223> OTHER INFORMATION: Light chain variable region

<400> SEQUENCE: 21

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Val Pro Arg Leu Leu Ile
        35                  40                  45
```

```
Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Gly Gly Thr Lys Val Glu Ile Lys
            100                 105

<210> SEQ ID NO 22
<211> LENGTH: 7
<212> TYPE: PRT
<213> ORGANISM: Artificial Sequence
<220> FEATURE:
<223> OTHER INFORMATION: CDR2

<400> SEQUENCE: 22

Gly Ala Ser Thr Arg Ala Thr
1               5

<210> SEQ ID NO 23
<211> LENGTH: 8
<212> TYPE: PRT
<213> ORGANISM: Artificial Sequence
<220> FEATURE:
<223> OTHER INFORMATION: CDR3

<400> SEQUENCE: 23

Gln Gln Tyr Asn Asn Trp Pro Thr
1               5

<210> SEQ ID NO 24
<211> LENGTH: 120
<212> TYPE: PRT
<213> ORGANISM: Artificial Sequence
<220> FEATURE:
<223> OTHER INFORMATION: Heavy chain variable region

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Met His Trp Val Arg Gln Ala Pro Gly Lys Gly Leu Glu Trp Val
        35                  40                  45

Ala Ile Ile Trp Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Lys Gln Trp Leu Val Ser Tyr Phe Asp Tyr Trp Gly Gln
            100                 105                 110

Gly Thr Leu Val Thr Val Ser Ser
        115                 120

<210> SEQ ID NO 25
<211> LENGTH: 11
<212> TYPE: PRT
<213> ORGANISM: Artificial Sequence
<220> FEATURE:
```

<223> OTHER INFORMATION: CDR3

<400> SEQUENCE: 25

Val Lys Gln Trp Leu Val Ser Tyr Phe Asp Tyr
1               5                   10

<210> SEQ ID NO 26
<211> LENGTH: 106
<212> TYPE: PRT
<213> ORGANISM: Artificial Sequence
<220> FEATURE:
<223> OTHER INFORMATION: Light chain variable region

<400> SEQUENCE: 26

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Val Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Ser Leu Ile Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Gly Gly Thr Lys Val Glu Ile Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: heavy chain variable region

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Ala Val Ser Ala Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Phe His Ser Gly Ser Asn Tyr Asn Pro Ser Leu
    50                  55                  60

Lys Ser Arg Val Thr Ile Ser Val Asp Pro Ser Lys Asn Gln Phe Ser
65                  70                  75                  80

Leu Lys Leu Ser Ser Val Thr Val Ala Asp Thr Ala Val Tyr Tyr Cys
                85                  90                  95

Ala Arg Glu Ser Ser Gly Tyr Asn Cys Phe Asp Tyr Trp Gly Gln Gly
            100                 105                 110

Thr Leu Val Thr Val Ser Ser
        115

<210> SEQ ID NO 28
<211> LENGTH: 6
<212> TYPE: PRT
<213> ORGANISM: Artificial Sequence
<220> FEATURE:
<223> OTHER INFORMATION: CDR1

<400> SEQUENCE: 28

Ser Gly Tyr Tyr Trp Gly
1               5

<210> SEQ ID NO 29
<211> LENGTH: 16
<212> TYPE: PRT
<213> ORGANISM: Artificial Sequence
<220> FEATURE:
<223> OTHER INFORMATION: CDR2

<400> SEQUENCE: 29

Ser Ile Phe His Ser Gly Ser Asn Tyr Tyr Asn Pro Ser Leu Lys Ser
1               5                   10                  15

<210> SEQ ID NO 30
<211> LENGTH: 10
<212> TYPE: PRT
<213> ORGANISM: Artificial Sequence
<220> FEATURE:
<223> OTHER INFORMATION: CDR3

<400> SEQUENCE: 30

Glu Ser Ser Gly Tyr Asn Cys Phe Asp Tyr
1               5                   10

<210> SEQ ID NO 31
<211> LENGTH: 108
<212> TYPE: PRT
<213> ORGANISM: Artificial Sequence
<220> FEATURE:
<223> OTHER INFORMATION: Light chain variable region

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Pro
                85                  90                  95

Tyr Thr Phe Gly Gln Gly Thr Lys Leu Glu Ile Lys
            100                 105

<210> SEQ ID NO 32
<211> LENGTH: 11
<212> TYPE: PRT
<213> ORGANISM: Artificial Sequence
<220> FEATURE:
<223> OTHER INFORMATION: CDR1

<400> SEQUENCE: 32

Arg Ala Ser Gln Ser Ile Ser Ser Trp Leu Ala
1               5                   10

<210> SEQ ID NO 33
<211> LENGTH: 7

```
<212> TYPE: PRT
<213> ORGANISM: Artificial Sequence
<220> FEATURE:
<223> OTHER INFORMATION: CDR2

<400> SEQUENCE: 33

Lys Ala Ser Ser Leu Glu Ser
1               5

<210> SEQ ID NO 34
<211> LENGTH: 10
<212> TYPE: PRT
<213> ORGANISM: Artificial Sequence
<220> FEATURE:
<223> OTHER INFORMATION: CDR3

<400> SEQUENCE: 34

Gln Gln Tyr Asn Ser Tyr Tyr Pro Tyr Thr
1               5                   10

<210> SEQ ID NO 35
<211> LENGTH: 119
<212> TYPE: PRT
<213> ORGANISM: Artificial Sequence
<220> FEATURE:
<223> OTHER INFORMATION: heavy chain variable region

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Phe His Ser Gly Ser Ser Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Arg Ser Val Thr Ala Ala Asp Thr Ala Val Tyr Tyr Cys
                85                  90                  95

Ala Arg Glu Ser Ser Gly Trp Asn Cys Phe Asp Tyr Trp Gly Gln Gly
            100                 105                 110

Thr Leu Val Thr Val Ser Ser
        115

<210> SEQ ID NO 36
<211> LENGTH: 17
<212> TYPE: PRT
<213> ORGANISM: Artificial Sequence
<220> FEATURE:
<223> OTHER INFORMATION: CDR2

<400> SEQUENCE: 36

Gly Ser Ile Phe His Ser Gly Ser Ser Tyr Tyr Asn Pro Ser Leu Lys
1               5                   10                  15

Ser

<210> SEQ ID NO 37
<211> LENGTH: 10
<212> TYPE: PRT
<213> ORGANISM: Artificial Sequence
<220> FEATURE:
<223> OTHER INFORMATION: CDR3
```

```
<400> SEQUENCE: 37

Glu Ser Ser Gly Trp Asn Cys Phe Asp Tyr
1               5                   10

<210> SEQ ID NO 38
<211> LENGTH: 107
<212> TYPE: PRT
<213> ORGANISM: Artificial Sequence
<220> FEATURE:
<223> OTHER INFORMATION: Light chain variable region

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Ile
                85                  90                  95

Thr Phe Gly Gln Gly Thr Arg Leu Glu Ile Lys
            100                 105

<210> SEQ ID NO 39
<211> LENGTH: 11
<212> TYPE: PRT
<213> ORGANISM: Artificial Sequence
<220> FEATURE:
<223> OTHER INFORMATION: CDR1

<400> SEQUENCE: 39

Arg Ala Ser Gln Thr Ile Ser Thr Trp Leu Ala
1               5                   10

<210> SEQ ID NO 40
<211> LENGTH: 7
<212> TYPE: PRT
<213> ORGANISM: Artificial Sequence
<220> FEATURE:
<223> OTHER INFORMATION: CDR2

<400> SEQUENCE: 40

Lys Ala Ser Asn Leu Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: CDR3

<400> SEQUENCE: 41

Gln Gln Tyr Asn Ser Tyr Ser Ile Thr
1               5

<210> SEQ ID NO 42
<211> LENGTH: 118
```

```
<212> TYPE: PRT
<213> ORGANISM: Artificial Sequence
<220> FEATURE:
<223> OTHER INFORMATION: heavy chain variable region

<400> SEQUENCE: 42

Gln Val Gln Leu Gln Gln Trp Gly Ala Gly Leu Leu Lys Pro Ser Glu
1               5                   10                  15

Thr Leu Ser Leu Thr Cys Gly Val Tyr Gly Gly Ser Phe Ser Thr Asn
            20                  25                  30

Tyr Trp Ser Trp Ile Arg Gln Ser Pro Gly Lys Gly Leu Glu Trp Ile
        35                  40                  45

Gly Glu Ile Asn His Ser Gly Asn Thr Glu Tyr Asn Pro Ser Leu Lys
    50                  55                  60

Ser Arg Leu Thr Ile Ser Ile Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Met Gly Tyr His Ser Pro Ser Phe Asp Phe Trp Gly Gln Gly Val
            100                 105                 110

Leu Val Thr Val Ser Ser
        115

<210> SEQ ID NO 43
<211> LENGTH: 5
<212> TYPE: PRT
<213> ORGANISM: Artificial Sequence
<220> FEATURE:
<223> OTHER INFORMATION: CDR1

<400> SEQUENCE: 43

Thr Asn Tyr Trp Ser
1               5

<210> SEQ ID NO 44
<211> LENGTH: 16
<212> TYPE: PRT
<213> ORGANISM: Artificial Sequence
<220> FEATURE:
<223> OTHER INFORMATION: CDR2

<400> SEQUENCE: 44

Glu Ile Asn His Ser Gly Asn Thr Glu Tyr Asn Pro Ser Leu Lys Ser
1               5                   10                  15

<210> SEQ ID NO 45
<211> LENGTH: 11
<212> TYPE: PRT
<213> ORGANISM: Artificial Sequence
<220> FEATURE:
<223> OTHER INFORMATION: CDR3

<400> SEQUENCE: 45

Arg Met Gly Tyr His Ser Pro Ser Phe Asp Phe
1               5                   10

<210> SEQ ID NO 46
<211> LENGTH: 107
<212> TYPE: PRT
<213> ORGANISM: Artificial Sequence
<220> FEATURE:
<223> OTHER INFORMATION: Light chain variable region
```

<400> SEQUENCE: 46

Lys Ile Val Met Thr Gln Ser Pro Ala Thr Leu Ser Val Ser Pro Gly
1               5                   10                  15

Glu Arg Ala Thr Leu Pro Cys Arg Val Ser Gln Gly Ile Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Ser Glu Phe Thr Leu Thr Ile Ser Ser Leu Gln Ser
65                  70                  75                  80

Glu Asp Leu Ala Leu Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 47
<211> LENGTH: 11
<212> TYPE: PRT
<213> ORGANISM: Artificial Sequence
<220> FEATURE:
<223> OTHER INFORMATION: CDR1

<400> SEQUENCE: 47

Arg Val Ser Gln Gly Ile Gly Ser Asn Leu Ala
1               5                   10

<210> SEQ ID NO 48
<211> LENGTH: 116
<212> TYPE: PRT
<213> ORGANISM: Artificial Sequence
<220> FEATURE:
<223> OTHER INFORMATION: heavy chain variable region

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Gly Pro Phe Asp Tyr Trp Gly Gln Gly Thr Leu Val
            100                 105                 110

Thr Val Ser Ser
        115

<210> SEQ ID NO 49
<211> LENGTH: 5
<212> TYPE: PRT
<213> ORGANISM: Artificial Sequence
<220> FEATURE:
<223> OTHER INFORMATION: CDR1

<400> SEQUENCE: 49

Ser Tyr Asp Ile Asn
1               5

<210> SEQ ID NO 50
<211> LENGTH: 17
<212> TYPE: PRT
<213> ORGANISM: Artificial Sequence
<220> FEATURE:
<223> OTHER INFORMATION: CDR2

<400> SEQUENCE: 50

Trp Met Asn Pro Asn Ser Gly Asn Thr Gly Tyr Ala Gln Lys Phe Gln
1               5                   10                  15

Gly

<210> SEQ ID NO 51
<211> LENGTH: 7
<212> TYPE: PRT
<213> ORGANISM: Artificial Sequence
<220> FEATURE:
<223> OTHER INFORMATION: CDR3

<400> SEQUENCE: 51

Glu Thr Gly Pro Phe Asp Tyr
1               5

<210> SEQ ID NO 52
<211> LENGTH: 107
<212> TYPE: PRT
<213> ORGANISM: Artificial Sequence
<220> FEATURE:
<223> OTHER INFORMATION: Light chain variable region

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Asn Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 53
<211> LENGTH: 11
<212> TYPE: PRT
<213> ORGANISM: Artificial Sequence
<220> FEATURE:
<223> OTHER INFORMATION: CDR1

<400> SEQUENCE: 53

Arg Ala Ser Gln Arg Ile Asn Asn Tyr Leu Asn
1               5                   10

<210> SEQ ID NO 54

```
<211> LENGTH: 7
<212> TYPE: PRT
<213> ORGANISM: Artificial Sequence
<220> FEATURE:
<223> OTHER INFORMATION: CDR2

<400> SEQUENCE: 54

Gly Ala Ser Ser Leu Gln Ser
1               5

<210> SEQ ID NO 55
<211> LENGTH: 9
<212> TYPE: PRT
<213> ORGANISM: Artificial Sequence
<220> FEATURE:
<223> OTHER INFORMATION: CDR3

<400> SEQUENCE: 55

Gln Gln Ser Tyr Ser Thr Pro Phe Thr
1               5

<210> SEQ ID NO 56
<211> LENGTH: 123
<212> TYPE: PRT
<213> ORGANISM: Artificial Sequence
<220> FEATURE:
<223> OTHER INFORMATION: heavy chain variable region

<400> SEQUENCE: 56

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Leu Ser
65                  70                  75                  80

Leu Asn Leu Ser Ser Val Thr Ala Ala Asp Thr Ala Val Tyr Tyr Cys
                85                  90                  95

Ala Arg Gln Gly Gly Val Ala Gly Thr Leu Tyr Trp Tyr Phe Asp Leu
            100                 105                 110

Trp Gly Arg Gly Thr Leu Val Thr Val Ser Ser
        115                 120

<210> SEQ ID NO 57
<211> LENGTH: 6
<212> TYPE: PRT
<213> ORGANISM: Artificial Sequence
<220> FEATURE:
<223> OTHER INFORMATION: CDR1

<400> SEQUENCE: 57

Ser Ser Asn Trp Trp Ser
1               5

<210> SEQ ID NO 58
<211> LENGTH: 16
<212> TYPE: PRT
<213> ORGANISM: Artificial Sequence
<220> FEATURE:
<223> OTHER INFORMATION: CDR2
```

-continued

<400> SEQUENCE: 58

Glu Ile Tyr His Ser Gly Ser Thr Asn Tyr Asn Pro Ser Leu Lys Ser
1               5                   10                  15

<210> SEQ ID NO 59
<211> LENGTH: 14
<212> TYPE: PRT
<213> ORGANISM: Artificial Sequence
<220> FEATURE:
<223> OTHER INFORMATION: CDR3

<400> SEQUENCE: 59

Gln Gly Gly Val Ala Gly Thr Leu Tyr Trp Tyr Phe Asp Leu
1               5                   10

<210> SEQ ID NO 60
<211> LENGTH: 112
<212> TYPE: PRT
<213> ORGANISM: Artificial Sequence
<220> FEATURE:
<223> OTHER INFORMATION: Light chain variable region

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Gly Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ile Gly Ser Gly Ser Gly Thr Asp Phe Thr Leu Lys Ile
65                  70                  75                  80

Arg Arg Val Glu Ala Glu Asp Val Gly Val Tyr Tyr Cys Met Gln Val
                85                  90                  95

Leu Gln Thr Pro Trp Thr Phe Gly Gln Gly Thr Lys Val Glu Ile Lys
            100                 105                 110

<210> SEQ ID NO 61
<211> LENGTH: 16
<212> TYPE: PRT
<213> ORGANISM: Artificial Sequence
<220> FEATURE:
<223> OTHER INFORMATION: CDR1

<400> SEQUENCE: 61

Arg Ser Ser Gln Gly Leu Leu His Ser Asn Gly Tyr Asn Tyr Leu Asp
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: CDR2

<400> SEQUENCE: 62

Leu Gly Ser Asn Arg Ala Ser
1               5

<210> SEQ ID NO 63
<211> LENGTH: 9
<212> TYPE: PRT

```
<213> ORGANISM: Artificial Sequence
<220> FEATURE:
<223> OTHER INFORMATION: CDR3

<400> SEQUENCE: 63

Met Gln Val Leu Gln Thr Pro Trp Thr
1               5

<210> SEQ ID NO 64
<211> LENGTH: 123
<212> TYPE: PRT
<213> ORGANISM: Artificial Sequence
<220> FEATURE:
<223> OTHER INFORMATION: heavy chain variable region

<400> SEQUENCE: 64

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ala Ile Arg Ser Ser
            20                  25                  30

Asn Trp Trp Ser Trp Val Arg Gln Ser Pro Gly Lys Gly Leu Glu Trp
        35                  40                  45

Ile Gly Glu Ile Tyr His Ser Gly Ser Thr Asn Tyr Lys Pro Ser Leu
    50                  55                  60

Lys Ser Arg Val Thr Ile Ser Ile Asp Lys Ser Lys Asn Gln Leu Ser
65                  70                  75                  80

Leu Lys Leu Ser Ser Val Thr Ala Ala Asp Met Ala Val Tyr Tyr Cys
                85                  90                  95

Ala Arg Gln Thr Gly Val Pro Gly Ser Leu Tyr Trp His Phe Asp Leu
            100                 105                 110

Trp Gly Arg Gly Thr Leu Val Thr Val Ser Ser
        115                 120

<210> SEQ ID NO 65
<211> LENGTH: 16
<212> TYPE: PRT
<213> ORGANISM: Artificial Sequence
<220> FEATURE:
<223> OTHER INFORMATION: CDR2

<400> SEQUENCE: 65

Glu Ile Tyr His Ser Gly Ser Thr Asn Tyr Lys Pro Ser Leu Lys Ser
1               5                   10                  15

<210> SEQ ID NO 66
<211> LENGTH: 14
<212> TYPE: PRT
<213> ORGANISM: Artificial Sequence
<220> FEATURE:
<223> OTHER INFORMATION: CDR3

<400> SEQUENCE: 66

Gln Thr Gly Val Pro Gly Ser Leu Tyr Trp His Phe Asp Leu
1               5                   10

<210> SEQ ID NO 67
<211> LENGTH: 112
<212> TYPE: PRT
<213> ORGANISM: Artificial Sequence
<220> FEATURE:
<223> OTHER INFORMATION: Light chain variable region
```

<400> SEQUENCE: 67

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 68
<211> LENGTH: 16
<212> TYPE: PRT
<213> ORGANISM: Artificial Sequence
<220> FEATURE:
<223> OTHER INFORMATION: CDR1

<400> SEQUENCE: 68

Arg Ser Ser Gln Ser Leu Leu His Ser Asn Gly Tyr Asn Tyr Leu Asp
1               5                   10                  15

<210> SEQ ID NO 69
<211> LENGTH: 9
<212> TYPE: PRT
<213> ORGANISM: Artificial Sequence
<220> FEATURE:
<223> OTHER INFORMATION: CDR3

<400> SEQUENCE: 69

Met Gln Ala Leu Gln Thr Pro Trp Thr
1               5

<210> SEQ ID NO 70
<211> LENGTH: 116
<212> TYPE: PRT
<213> ORGANISM: Artificial Sequence
<220> FEATURE:
<223> OTHER INFORMATION: heavy chain variable region

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Val Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Gly Pro Phe Asp Tyr Trp Gly Gln Gly Thr Leu Val
            100                 105                 110

Thr Val Ser Ser
        115

<210> SEQ ID NO 71
<211> LENGTH: 17
<212> TYPE: PRT
<213> ORGANISM: Artificial Sequence
<220> FEATURE:
<223> OTHER INFORMATION: CDR2

<400> SEQUENCE: 71

Trp Met Asn Pro Asn Ser Gly Asn Thr Gly Tyr Val Gln Lys Phe Gln
1               5                   10                  15

Gly

<210> SEQ ID NO 72
<211> LENGTH: 107
<212> TYPE: PRT
<213> ORGANISM: Artificial Sequence
<220> FEATURE:
<223> OTHER INFORMATION: Light chain variable region

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 73
<211> LENGTH: 11
<212> TYPE: PRT
<213> ORGANISM: Artificial Sequence
<220> FEATURE:
<223> OTHER INFORMATION: CDR1

<400> SEQUENCE: 73

Arg Ala Ser Gln Ser Ile Ser Ile Tyr Leu Asn
1               5                   10

<210> SEQ ID NO 74
<211> LENGTH: 123
<212> TYPE: PRT
<213> ORGANISM: Artificial Sequence
<220> FEATURE:
<223> OTHER INFORMATION: heavy chain variable region

<400> SEQUENCE: 74

Gln Val Gln Leu Gln Glu Ser Gly Pro Gly Leu Val Lys Pro Ser Gly
1               5                   10                  15

```
Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Met Ser Val Asp Lys Ser Lys Asn Gln Phe Ser
65                  70                  75                  80

Leu Glu Leu Arg Ser Val Thr Ala Ala Asp Thr Ala Val Tyr Tyr Cys
                85                  90                  95

Ala Arg Asp Ala Val Asp Ala Tyr Tyr Tyr Tyr Gly Met Asp Val
            100                 105                 110

Trp Gly Gln Gly Thr Thr Val Thr Val Ser Ser
        115                 120
```

<210> SEQ ID NO 75
<211> LENGTH: 14
<212> TYPE: PRT
<213> ORGANISM: Artificial Sequence
<220> FEATURE:
<223> OTHER INFORMATION: CDR3

<400> SEQUENCE: 75

```
Asp Ala Val Asp Ala Tyr Tyr Tyr Tyr Gly Met Asp Val
1               5                   10
```

<210> SEQ ID NO 76
<211> LENGTH: 107
<212> TYPE: PRT
<213> ORGANISM: Artificial Sequence
<220> FEATURE:
<223> OTHER INFORMATION: Light chain variable region

<400> SEQUENCE: 76

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Leu Asn Ser Tyr Pro Phe
                85                  90                  95

Thr Phe Gly Pro Gly Thr Lys Val Asp Leu Lys
            100                 105
```

<210> SEQ ID NO 77
<211> LENGTH: 11
<212> TYPE: PRT
<213> ORGANISM: Artificial Sequence
<220> FEATURE:
<223> OTHER INFORMATION: CDR1

<400> SEQUENCE: 77

```
Arg Ala Ser Gln Gly Ile Ser Ser Tyr Leu Ala
1               5                   10
```

```
<210> SEQ ID NO 78
<211> LENGTH: 9
<212> TYPE: PRT
<213> ORGANISM: Artificial Sequence
<220> FEATURE:
<223> OTHER INFORMATION: CDR3

<400> SEQUENCE: 78

Gln His Leu Asn Ser Tyr Pro Phe Thr
1               5

<210> SEQ ID NO 79
<211> LENGTH: 119
<212> TYPE: PRT
<213> ORGANISM: Artificial Sequence
<220> FEATURE:
<223> OTHER INFORMATION: heavy chain variable region

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Gly Pro Gly Lys Gly Leu Glu Trp Val
        35                  40                  45

Ser Thr Ile Ile Gly Ser Gly Asp Ser Thr Tyr Tyr Thr Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Lys Ser Gly Trp Tyr Tyr Phe Asp Tyr Trp Gly Gln Gly
            100                 105                 110

Thr Leu Val Thr Val Ser Ser
        115

<210> SEQ ID NO 80
<211> LENGTH: 5
<212> TYPE: PRT
<213> ORGANISM: Artificial Sequence
<220> FEATURE:
<223> OTHER INFORMATION: CDR1

<400> SEQUENCE: 80

Asn Tyr Ala Met Ser
1               5

<210> SEQ ID NO 81
<211> LENGTH: 17
<212> TYPE: PRT
<213> ORGANISM: Artificial Sequence
<220> FEATURE:
<223> OTHER INFORMATION: CDR2

<400> SEQUENCE: 81

Thr Ile Ile Gly Ser Gly Asp Ser Thr Tyr Tyr Thr Asp Ser Val Lys
1               5                   10                  15

Gly

<210> SEQ ID NO 82
<211> LENGTH: 10
<212> TYPE: PRT
<213> ORGANISM: Artificial Sequence
```

<220> FEATURE:
<223> OTHER INFORMATION: CDR3

<400> SEQUENCE: 82

Asp Lys Ser Gly Trp Tyr Tyr Phe Asp Tyr
1               5                   10

<210> SEQ ID NO 83
<211> LENGTH: 108
<212> TYPE: PRT
<213> ORGANISM: Artificial Sequence
<220> FEATURE:
<223> OTHER INFORMATION: Light chain variable region

<400> SEQUENCE: 83

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asp Tyr Phe Pro
                85                  90                  95

Ile Thr Phe Gly Gln Gly Thr Arg Leu Glu Ile Lys
            100                 105

<210> SEQ ID NO 84
<211> LENGTH: 12
<212> TYPE: PRT
<213> ORGANISM: Artificial Sequence
<220> FEATURE:
<223> OTHER INFORMATION: CDR1

<400> SEQUENCE: 84

Cys Arg Ala Ser Gln Ser Ile Ser Asn Trp Leu Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: CDR3

<400> SEQUENCE: 85

Gln Gln Tyr Asn Asp Tyr Phe Pro Ile Thr
1               5                   10

<210> SEQ ID NO 86
<211> LENGTH: 128
<212> TYPE: PRT
<213> ORGANISM: Artificial Sequence
<220> FEATURE:
<223> OTHER INFORMATION: heavy chain variable region

<400> SEQUENCE: 86

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
         20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Asn Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Gly Pro Tyr Leu Tyr Ser Ser Gly Trp Tyr Asp Tyr Tyr Tyr
                100                 105                 110

Tyr Gly Met Asp Val Trp Gly Gln Gly Thr Thr Val Thr Val Ser Ser
            115                 120                 125
```

<210> SEQ ID NO 87
<211> LENGTH: 20
<212> TYPE: PRT
<213> ORGANISM: Artificial Sequence
<220> FEATURE:
<223> OTHER INFORMATION: CDR3

<400> SEQUENCE: 87

```
Gly Pro Tyr Leu Tyr Ser Ser Gly Trp Tyr Asp Tyr Tyr Tyr Tyr Gly
1               5                   10                  15

Met Asp Val Trp
            20
```

<210> SEQ ID NO 88
<211> LENGTH: 107
<212> TYPE: PRT
<213> ORGANISM: Artificial Sequence
<220> FEATURE:
<223> OTHER INFORMATION: Light chain variable region

<400> SEQUENCE: 88

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Pro Leu
                85                  90                  95

Thr Phe Gly Gly Gly Thr Lys Val Glu Ile Lys
            100                 105
```

<210> SEQ ID NO 89
<211> LENGTH: 12
<212> TYPE: PRT
<213> ORGANISM: Artificial Sequence
<220> FEATURE:
<223> OTHER INFORMATION: CDR1

<400> SEQUENCE: 89

Cys Arg Ala Ser Gln Ser Ile Ser Ser Tyr Leu Asn
1               5                   10

<210> SEQ ID NO 90
<211> LENGTH: 7
<212> TYPE: PRT
<213> ORGANISM: Artificial Sequence
<220> FEATURE:
<223> OTHER INFORMATION: CDR2

<400> SEQUENCE: 90

Ala Ala Ser Ser Leu Gln Ser
1               5

<210> SEQ ID NO 91
<211> LENGTH: 9
<212> TYPE: PRT
<213> ORGANISM: Artificial Sequence
<220> FEATURE:
<223> OTHER INFORMATION: CDR3

<400> SEQUENCE: 91

Gln Gln Ser Tyr Arg Thr Pro Leu Thr
1               5

<210> SEQ ID NO 92
<211> LENGTH: 128
<212> TYPE: PRT
<213> ORGANISM: Artificial Sequence
<220> FEATURE:
<223> OTHER INFORMATION: heavy chain variable region

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Tyr Leu Tyr Ser Ser Gly Trp Tyr Asp Tyr Tyr Tyr
            100                 105                 110

Tyr Gly Met Asp Val Trp Gly Gln Gly Thr Thr Val Thr Val Ser Ser
        115                 120                 125

<210> SEQ ID NO 93
<211> LENGTH: 107
<212> TYPE: PRT
<213> ORGANISM: Artificial Sequence
<220> FEATURE:
<223> OTHER INFORMATION: Light chain variable region

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Thr Pro Leu
                85                  90                  95

Thr Phe Gly Gly Gly Thr Lys Val Glu Ile Lys
            100                 105

<210> SEQ ID NO 94
<211> LENGTH: 11
<212> TYPE: PRT
<213> ORGANISM: Artificial Sequence
<220> FEATURE:
<223> OTHER INFORMATION: CDR1

<400> SEQUENCE: 94

Arg Ala Ser Gln Ile Ile Ser Ser Tyr Leu Asn
1               5                   10

<210> SEQ ID NO 95
<211> LENGTH: 116
<212> TYPE: PRT
<213> ORGANISM: Artificial Sequence
<220> FEATURE:
<223> OTHER INFORMATION: heavy chain variable region

<400> SEQUENCE: 95

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Ser Tyr Asn Pro Ser Leu
50                  55                  60

Arg Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Gly Gly Phe Asp Tyr Trp Gly Gln Gly Thr Leu Val
            100                 105                 110

Thr Val Ser Ser
        115

<210> SEQ ID NO 96
<211> LENGTH: 17
<212> TYPE: PRT
<213> ORGANISM: Artificial Sequence
<220> FEATURE:
<223> OTHER INFORMATION: CDR2

<400> SEQUENCE: 96

Gly Ser Ile Tyr His Ser Gly Ser Thr Ser Tyr Asn Pro Ser Leu Arg
1               5                   10                  15

Ser

<210> SEQ ID NO 97
<211> LENGTH: 7
<212> TYPE: PRT
<213> ORGANISM: Artificial Sequence
<220> FEATURE:
<223> OTHER INFORMATION: CDR3

<400> SEQUENCE: 97

Asp Ala Gly Gly Phe Asp Tyr
1               5

<210> SEQ ID NO 98
<211> LENGTH: 107
<212> TYPE: PRT
<213> ORGANISM: Artificial Sequence
<220> FEATURE:
<223> OTHER INFORMATION: Light chain variable region

<400> SEQUENCE: 98

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Cys Cys Gln Gln Tyr Asn Ser Tyr Ser His
                85                  90                  95

Thr Phe Gly Gln Gly Thr Lys Leu Glu Ile Lys
            100                 105

<210> SEQ ID NO 99
<211> LENGTH: 8
<212> TYPE: PRT
<213> ORGANISM: Artificial Sequence
<220> FEATURE:
<223> OTHER INFORMATION: CDR3

<400> SEQUENCE: 99

Gln Gln Tyr Asn Ser Tyr Ser His
1               5

<210> SEQ ID NO 100
<211> LENGTH: 119
<212> TYPE: PRT
<213> ORGANISM: Artificial Sequence
<220> FEATURE:
<223> OTHER INFORMATION: heavy chain variable region

<400> SEQUENCE: 100

Gln Val Gln Leu Gln Glu Ser Gly Pro Gly Leu Val Arg Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Phe His Ser Gly Asn Thr Tyr Tyr Asn Pro Ser Leu
    50                  55                  60

Lys Ser Arg Val Ile Val Ser Gly Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Thr Arg Glu Ser Ser Gly Phe Asn Val Phe Asp Ile Trp Gly Gln Gly
            100                 105                 110

Thr Met Val Thr Val Ser Ser
        115

<210> SEQ ID NO 101
<211> LENGTH: 16
<212> TYPE: PRT
<213> ORGANISM: Artificial Sequence
<220> FEATURE:
<223> OTHER INFORMATION: CDR2

<400> SEQUENCE: 101

Ser Ile Phe His Ser Gly Asn Thr Tyr Tyr Asn Pro Ser Leu Lys Ser
1               5                   10                  15

<210> SEQ ID NO 102
<211> LENGTH: 10
<212> TYPE: PRT
<213> ORGANISM: Artificial Sequence
<220> FEATURE:
<223> OTHER INFORMATION: CDR3

<400> SEQUENCE: 102

Glu Ser Ser Gly Phe Asn Val Phe Asp Ile
1               5                   10

<210> SEQ ID NO 103
<211> LENGTH: 107
<212> TYPE: PRT
<213> ORGANISM: Artificial Sequence
<220> FEATURE:
<223> OTHER INFORMATION: Light chain variable region

<400> SEQUENCE: 103

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 104
<211> LENGTH: 11
<212> TYPE: PRT
<213> ORGANISM: Artificial Sequence
<220> FEATURE:
<223> OTHER INFORMATION: CDR1

<400> SEQUENCE: 104

Arg Ala Ser Gln Asn Ile Gly Ser Trp Leu Ala
1               5                   10

<210> SEQ ID NO 105
<211> LENGTH: 9
<212> TYPE: PRT
<213> ORGANISM: Artificial Sequence
<220> FEATURE:
<223> OTHER INFORMATION: CDR3

<400> SEQUENCE: 105

Gln Gln Tyr Asn Ser Tyr Ser Tyr Thr
1               5

<210> SEQ ID NO 106
<211> LENGTH: 375
<212> TYPE: DNA
<213> ORGANISM: Artificial Sequence
<220> FEATURE:
<223> OTHER INFORMATION: heavy chain variable region

<400> SEQUENCE: 106
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagagcca gttctccctg     240
aagctgacct ctgtgaccgc tgcggacacg gccgtgtatt actgtgcgaa agattcggat     300
tactatggtt cggggagtta ttcgtactgg tacttcgatc tctggggccg tggcaccctg     360
gtcactgtct cctca                                                     375

<210> SEQ ID NO 107
<211> LENGTH: 321
<212> TYPE: DNA
<213> ORGANISM: Artificial Sequence
<220> FEATURE:
<223> OTHER INFORMATION: Light chain variable region

<400> SEQUENCE: 107
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggcccctgg tatcccagcc     180
aggttcagtg gcagtgggtc tgggacagag ttcactctca ccatcagcag cctgcagtct     240
gaagattttg cagtttatta ctgtcagcag tataataact ggcctctcac tttcggcgga     300
gggaccaagg tggagatcaa a                                              321

<210> SEQ ID NO 108
<211> LENGTH: 384
<212> TYPE: DNA
<213> ORGANISM: Artificial Sequence
<220> FEATURE:
<223> OTHER INFORMATION: heavy chain variable region

<400> SEQUENCE: 108
caggtgcagc tggtggagtc tgggggaggc gtggtccagc ctggggaggtc cctgagactc      60 tcctgtgcag cgtctggatt gaccttcagt agctatggca tgcactgggt ccgccaggct     120

| | |
|---|---|
| ccaggcaagg ggctggagtg ggtggcagtt atatggtatg atggaagtaa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagaggag | 300 |
| gtactatggt tcggggagtt atcgtataac tactactacg gtatggacgt ctggggccaa | 360 |
| gggaccacgg tcaccgtctc ctca | 384 |

<210> SEQ ID NO 109
<211> LENGTH: 321
<212> TYPE: DNA
<213> ORGANISM: Artificial Sequence
<220> FEATURE:
<223> OTHER INFORMATION: Light chain variable region

<400> SEQUENCE: 109

| | |
|---|---|
| gacatccaga tgacccagtc tccatcctcc ctgtctgcat ctgtaggaga cagagtcacc | 60 |
| atcacttgcc gggcgagtca gggcattagc aattatttag cctggtatca gcagaaacca | 120 |
| gggaaagttc ctaagctcct gatctatgct gcatccactt tgcaatcagg ggtcccatct | 180 |
| cggttcagtg gcagtggatc tgggacagat ttcactctca ccatcagcag cctgcagcct | 240 |
| gaagatgttg caacttatta ctgtcaaaag tataacagtg cccgctcac tttcggcgga | 300 |
| gggaccaagg tggagatcaa a | 321 |

<210> SEQ ID NO 110
<211> LENGTH: 360
<212> TYPE: DNA
<213> ORGANISM: Artificial Sequence
<220> FEATURE:
<223> OTHER INFORMATION: heavy chain variable region

<400> SEQUENCE: 110

| | |
|---|---|
| caggtgcagc tggtggagtc tgggggaggc gtggtccagc ctgggaggtc cctgagactc | 60 |
| tcctgtgcag cgtctggatt caccttcagt agctatgcca tgcactgggt ccgccaggct | 120 |
| ccaggcaagg ggctggagtg ggtggcaatt atatggtatg atggaagtaa tcaatactat | 180 |
| gcagactccg tgaagggccg attcaccatc tccagagaca attccatgaa cacgctgtat | 240 |
| ctgcaaatga acagcctgag agccgaggac acggctgtgt attattgtgc gagagtggag | 300 |
| cagtggctgg tgtcctactt tgacttctgg ggccagggaa ccctggtcac cgtctcctca | 360 |

<210> SEQ ID NO 111
<211> LENGTH: 318
<212> TYPE: DNA
<213> ORGANISM: Artificial Sequence
<220> FEATURE:
<223> OTHER INFORMATION: Light chain variable region

<400> SEQUENCE: 111

| | |
|---|---|
| gaaatagtga tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggttc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcag tataataact ggcctacttt cggcggaggg | 300 |
| accaaggtgg agatcaaa | 318 |

<210> SEQ ID NO 112
<211> LENGTH: 360

<212> TYPE: DNA
<213> ORGANISM: Artificial Sequence
<220> FEATURE:
<223> OTHER INFORMATION: heavy chain variable region

<400> SEQUENCE: 112

| | | | | | |
|---|---|---|---|---|---|
| caggtgcagc | tggtggagtc | tgggggaggc | gtggtccagc | ctgggaggtc | cctgagactc | 60 |
| tcctgtgcag | cgtctggatt | ctccttcagt | agctatgcca | tgcactgggt | ccgccaggct | 120 |
| ccaggcaagg | ggctggagtg | ggtggcaatt | atatggtatg | atggaagtaa | tcaatactat | 180 |
| gcagactccg | tgaagggccg | attcaccatc | tccagagaca | attccaagaa | cacgctgtat | 240 |
| ctgcagatga | acagcctgag | agccgaagac | acggctgtgt | attactgtgc | gcgagtgaaa | 300 |
| cagtggctgg | tgtcctactt | tgactactgg | ggccagggaa | ccctggtcac | cgtctcctca | 360 |

<210> SEQ ID NO 113
<211> LENGTH: 318
<212> TYPE: DNA
<213> ORGANISM: Artificial Sequence
<220> FEATURE:
<223> OTHER INFORMATION: Light chain variable region

<400> SEQUENCE: 113

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagc | agcaacttag | cctggtacca | gcagaaacct | 120 |
| ggccaggttc | ccaggctcct | catctatggt | gcatccacca | gggccactgg | tatcccagcc | 180 |
| aggttcagtg | gcagtgggtc | tgggacagag | ttcagtctca | tcatcagcag | cctgcagtct | 240 |
| gaagattttg | cagtttatta | ctgtcagcag | tataataact | ggcctacttt | cggcggaggg | 300 |
| accaaggtgg | agatcaaa | | | | | 318 |

<210> SEQ ID NO 114
<211> LENGTH: 357
<212> TYPE: DNA
<213> ORGANISM: Artificial Sequence
<220> FEATURE:
<223> OTHER INFORMATION: heavy chain variable region

<400> SEQUENCE: 114

| | | | | | |
|---|---|---|---|---|---|
| caggtgcagt | tgcaggagtc | gggcccagga | ctggtgaagc | cttcggagac | cctgtccctc | 60 |
| acctgcgctg | tctctgctta | ctccatcagt | agcggttact | actggggctg | gatccggcag | 120 |
| cccccaggga | aggggctgga | gtggattggg | agtatctttc | atagtgggag | caactactac | 180 |
| aacccgtccc | tcaagagtcg | agtcaccata | tcagtagacc | cgtccaagaa | ccagttctcc | 240 |
| ctgaagctga | gctctgtgac | cgtcgcagac | acggccgtgt | attactgtgc | gagagaatcc | 300 |
| agtggctaca | actgttttga | ctactggggc | cagggaaccc | tggtcaccgt | ctcctca | 357 |

<210> SEQ ID NO 115
<211> LENGTH: 324
<212> TYPE: DNA
<213> ORGANISM: Artificial Sequence
<220> FEATURE:
<223> OTHER INFORMATION: Light chain variable region

<400> SEQUENCE: 115

| | | | | | |
|---|---|---|---|---|---|
| gacatccaga | tgacccagtc | tccttccacc | ctgtctgcat | ctgtaggaga | cagagtcacc | 60 |
| atcacttgcc | gggccagtca | gagtattagt | agctggttgg | cctggtatca | gcagaaacca | 120 |
| gggaaagccc | ctaagctcct | gatctataag | gcgtctagtt | tagaaagtgg | ggtcccatca | 180 |

```
aggttcagcg gcagtggatc tgggacagaa ttcactctca ccatcagcag cctgcagcct    240
gatgattttg caacttatta ctgccaacag tataatagtt attacccgta cacttttggc    300
caggggacca agctggagat caag                                           324
```

<210> SEQ ID NO 116
<211> LENGTH: 357
<212> TYPE: DNA
<213> ORGANISM: Artificial Sequence
<220> FEATURE:
<223> OTHER INFORMATION: heavy chain variable region

<400> SEQUENCE: 116

```
caggtgcagc tgcaggagtc gggcccagga ctggtgaagc cttcggagac cctgtcactc     60
acctgcgctg tctctggtta ctccatcagc agtggttact actggggctg gatccggcag    120
cccccaggga aggggctgga gtggattggg agtatctttc atagtgggag tagttactac    180
aacccgtccc tcaagagtcg agtcaccata tcagtcgaca cgtccaagaa ccagttctcc    240
ctgaagttga ggtctgtgac cgccgccgac acggccgtgt attactgtgc gagagagagt    300
agtggctgga actgctttga ctattggggc cagggaaccc tggtcaccgt ctcctca       357
```

<210> SEQ ID NO 117
<211> LENGTH: 321
<212> TYPE: DNA
<213> ORGANISM: Artificial Sequence
<220> FEATURE:
<223> OTHER INFORMATION: Light chain variable region

<400> SEQUENCE: 117

```
gacatccaga tgacccagtc tccttccacc ctgtctgcat ctgtaggaga cagagtcacc     60
atcacttgcc gggccagtca gactattagt acctggttgg cctggtatca gcagaaacca    120
gggaaagccc ctaagctcct gatctataag gcgtctaatt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgatcac cttcggccaa    300
gggacacgac tggagattaa a                                              321
```

<210> SEQ ID NO 118
<211> LENGTH: 354
<212> TYPE: DNA
<213> ORGANISM: Artificial Sequence
<220> FEATURE:
<223> OTHER INFORMATION: heavy chain variable region

<400> SEQUENCE: 118

```
caggtgcagc tacagcagtg gggcgcagga ctgttgaagc cttcggagac cctgtccctc     60
acctgcggtg tctatggtgg gtccttcagt actaactact ggagctggat ccgtcagtcc    120
ccagggaagg ggctgagtg gattggggaa atcaatcata gtggaaacac cgagtacaac    180
ccgtccctca agagtcgact caccatatca atagacacgt ccaagaacca gttctccctg    240
aagctgacct ctgtgaccgc cgcggacacg gctgtgtatt actgtgcgag aatggggtat    300
cacagtccct cttttgactt ctggggccag ggagtcctgg tcaccgtctc ctca          354
```

<210> SEQ ID NO 119
<211> LENGTH: 321
<212> TYPE: DNA
<213> ORGANISM: Artificial Sequence
<220> FEATURE:
<223> OTHER INFORMATION: Light chain variable region

<400> SEQUENCE: 119

```
aaaatagtga tgacgcagtc tccagccacc ctgtctgtgt ctccagggga aagagccacc      60
ctcccctgca gggtcagtca aggtattggc agcaacttag cctggtacca gcagaaacct    120
ggccaggctc ccaggctcct catctatggt gcgtccacca gggccactgg tgtcccagcc    180
aggttcagtg gcagtgggtc tgggtcagag ttcactctca ccatcagcag cctgcagtct    240
gaagatcttg cactttatta ctgtcagcag tataataact ggccgctcac tttcggcgga    300
gggaccaagg tggagatcaa a                                               321
```

<210> SEQ ID NO 120
<211> LENGTH: 348
<212> TYPE: DNA
<213> ORGANISM: Artificial Sequence
<220> FEATURE:
<223> OTHER INFORMATION: heavy chain variable region

<400> SEQUENCE: 120

```
caggtgcagc tggtgcagtc tggggctgag gtgaagaagc ctggggcctc agtgaaggtc      60
tcctgcaagg cttctggata caccttcacc agttatgata tcaactgggt tcgacaggcc    120
actggacaag gcttgagtg gatgggatgg atgaaccctaa acagtggtaa cacaggctat    180
gcacagaagt tccagggcag agtcaccatg accaggaaca cctccataag cacagcctac    240
atggagctga gcagcctgag atctgaggac acggccgtgt attactgtgc gagagaaact    300
gggccctttg actactgggg ccagggaacc ctggtcaccg tctcctca                 348
```

<210> SEQ ID NO 121
<211> LENGTH: 321
<212> TYPE: DNA
<213> ORGANISM: Artificial Sequence
<220> FEATURE:
<223> OTHER INFORMATION: Light chain variable region

<400> SEQUENCE: 121

```
gacatccaga tgacccagtc tccatcctcc ctgtctgcat ctgtaggaga cagagtcacc      60
atcacttgcc gggcaagtca gagaattaac aactatttaa attggtatca gcagaaacca    120
gggaaagccc ctaagctcct gatctatggt gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccattcac tttcggccct    300
gggaccaaag tggatatcaa a                                               321
```

<210> SEQ ID NO 122
<211> LENGTH: 369
<212> TYPE: DNA
<213> ORGANISM: Artificial Sequence
<220> FEATURE:
<223> OTHER INFORMATION: heavy chain variable region

<400> SEQUENCE: 122

```
caggtgcagc tgcaggagtc gggcccagga ctggtgaagc cttcggggac cctgtccctc      60
acctgcgctg tctctggtgg ctccatcagc agtagtaact ggtggagttg gtccgccag     120 cccccaggga aggggctgga gtggattggg gaaatctatc atagtgggag caccaactac    180
aacccgtccc tcaagagtcg agtcaccata tcagtagaca gtccaagaa ccagctctcc     240 ctgaacctga gctctgtgac cgccgcggac acggccgtgt attactgtgc gagacaagga    300
```

```
ggagtggctg gtaccctcta ctggtacttc gatctctggg gccgtggcac cctggtcact    360
gtctcctca                                                            369
```

```
<210> SEQ ID NO 123
<211> LENGTH: 336
<212> TYPE: DNA
<213> ORGANISM: Artificial Sequence
<220> FEATURE:
<223> OTHER INFORMATION: Light chain variable region

<400> SEQUENCE: 123
gatattgtga tgactcagtc tccactctcc ctgcccgtca cccctggaga gccggcctcc     60
atctcctgca ggtctagtca gggcctcctg catagtaatg gatacaacta tttggattgg    120
tacctgcaga agccagggca gtctccacag ctcctgatct atctgggttc taatcgggcc    180
tccggggtcc ctgacaggtt cattggcagt ggatcaggca cagatttta actgaaaatc     240 aggagagtgg aggctgagga tgttggggtt tattactgca tgcaagttct acaaactccg    300
tggacgttcg gccaagggac caaggtggaa atcaaa                              336
```

```
<210> SEQ ID NO 124
<211> LENGTH: 369
<212> TYPE: DNA
<213> ORGANISM: Artificial Sequence
<220> FEATURE:
<223> OTHER INFORMATION: heavy chain variable region

<400> SEQUENCE: 124
caggtgcagc tgcaggagtc gggcccagga ctggtgaagc cttcggggac cctgtccctc     60
acctgcgctg tctctggtgg cgccatcagg agcagtaact ggtggagttg gtccgccag    120 tccccaggga aggggctgga gtggattggg gaaatctatc atagtgggag taccaactac    180
aagccgtccc tcaagagtcg agtcaccata tcaatagaca agtccaagaa ccagctctcc    240
ctgaagctga gttctgtgac cgccgcggac atggccgtgt attactgtgc gagacagaca    300
ggagtgcctg gttccctcta ctggcacttc gatctctggg gccgtggcac cctggtcact    360
gtctcctca                                                            369
```

```
<210> SEQ ID NO 125
<211> LENGTH: 336
<212> TYPE: DNA
<213> ORGANISM: Artificial Sequence
<220> FEATURE:
<223> OTHER INFORMATION: Light chain variable region

<400> SEQUENCE: 125
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttta actgaaaatc     240 agcagagtgg aggctgagga tgttggggtt tattactgca tgcaagctct acaaactccg    300
tggacgttcg gccaagggac caaggtggaa atcaaa                              336
```

```
<210> SEQ ID NO 126
<211> LENGTH: 348
<212> TYPE: DNA
<213> ORGANISM: Artificial Sequence
<220> FEATURE:
<223> OTHER INFORMATION: heavy chain variable region
```

<400> SEQUENCE: 126

```
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atgaacccta acagtggtaa cacaggctat   180
gtacagaagt tccagggcag agtcaccatg accaggaaca cctccataag cacagcctac   240
atggagctga gcagcctgag atctgaggac acggccgtgt attactgtgc gagagaaact   300
gggccctttg actactgggg ccagggaacc ctggtcaccg tctcctca               348
```

<210> SEQ ID NO 127
<211> LENGTH: 321
<212> TYPE: DNA
<213> ORGANISM: Artificial Sequence
<220> FEATURE:
<223> OTHER INFORMATION: Light chain variable region

<400> SEQUENCE: 127

```
gacatccaga tgacccagtc tccatcctcc ctgtctgcat ctgtaggaga cagagtcacc    60
atcacttgcc gggcaagtca gagcattagc atctatttaa attggtatca gcagaaaccg   120
gggaaagccc ctaagctcct gatctatggt gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccattcac tttcggccct   300
gggaccaaag tggatatcaa a                                             321
```

<210> SEQ ID NO 128
<211> LENGTH: 369
<212> TYPE: DNA
<213> ORGANISM: Artificial Sequence
<220> FEATURE:
<223> OTHER INFORMATION: heavy chain variable region

<400> SEQUENCE: 128

```
caggtgcagc tgcaggagtc gggcccagga ctggtgaagc cttcggggac cctgtccctc    60
acctgcgctg tctctggtgg ctccatcagc agtagtaact ggtggagttg ggtccgccag   120
cccccaggga aggggctgga gtggattggg gaaatctatc atagtgggag caccaactat   180
aacccgtccc tcaagagtcg agtcaccatg tcagtagaca agtccaagaa ccagttctcc   240
ctggagctga gtctgtgac cgccgcggac acggccgtgt attactgtgc gagagacgca   300
gttgacgctt actactacta ctacggtatg gacgtctggg gccaagggac cacggtcacc   360
gtctcctca                                                           369
```

<210> SEQ ID NO 129
<211> LENGTH: 321
<212> TYPE: DNA
<213> ORGANISM: Artificial Sequence
<220> FEATURE:
<223> OTHER INFORMATION: Light chain variable region

<400> SEQUENCE: 129

```
gacatccagt tgacccagtc tccatccttc ctgtctgcat ctgtaggaga cagagtcacc    60
atcacttgcc gggccagtca gggcattagc agttatttag cctggtatca gcaaaaacca   120
gggaaagccc ctaagctcct gatctatgct gcatccactt tgcaaagtgg ggtcccatcg   180
aggttcagcg gcagtggatc tgggacagaa ttcactctca caatcagcag cctgcagcct   240
```

```
gaagattttg caacttatta ctgtcaacac cttaatagtt acccattcac tttcggccct    300
gggaccaaag tggatctcaa a                                              321
```

<210> SEQ ID NO 130
<211> LENGTH: 357
<212> TYPE: DNA
<213> ORGANISM: Artificial Sequence
<220> FEATURE:
<223> OTHER INFORMATION: heavy chain variable region

<400> SEQUENCE: 130

```
gaggtgcagc tgttggagtc tgggggaggc ttggtacagc ctgggggtc cctgagactc     60 tcctgtgcag cctctggatt cacctttagc aactatgcca tgagctgggt ccgccagggt   120
ccagggaagg gctggagtg gtctcaact attattggta gtggtgatag cacatactac     180
acagactccg tgaagggccg gttcaccatc tccagagaca attccaagaa cacgttgttt   240
ctgcaaatga acagcctgag agccgaggac acggccgtat attactgtgc gagagataaa   300
agtggctggt actactttga ctactgggc cagggaaccc tggtcaccgt ctcctca      357
```

<210> SEQ ID NO 131
<211> LENGTH: 324
<212> TYPE: DNA
<213> ORGANISM: Artificial Sequence
<220> FEATURE:
<223> OTHER INFORMATION: Light chain variable region

<400> SEQUENCE: 131

```
gacatccaga tgacccagtc tccttccacc ctgtctgcat ctgtaggaga cagagtcacc    60
atcacttgcc gggccagtca gagtattagt aactggttgg cctggtatca gcagaaacca   120
ggaaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatgatt attttccgat caccttcggc   300
caagggacac gactggagat taaa                                          324
```

<210> SEQ ID NO 132
<211> LENGTH: 384
<212> TYPE: DNA
<213> ORGANISM: Artificial Sequence
<220> FEATURE:
<223> OTHER INFORMATION: heavy chain variable region

<400> SEQUENCE: 132

```
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg gctggagtg gtggcagtt atatggtatg atggaagtaa taaatactat    180
gcagactccg tgaagggccg attcaacatc tccagagaca attccaagaa cacgctgtat   240
ctgcaaatga acagcctgag agccgaggac acggctgtgt attactgtgc gagaggaccc   300
tatctgtata gcagtggctg gtacgactac tactactacg gtatggacgt ctggggccaa   360
gggaccacgg tcaccgtctc ctca                                          384
```

<210> SEQ ID NO 133
<211> LENGTH: 321
<212> TYPE: DNA
<213> ORGANISM: Artificial Sequence
<220> FEATURE:
<223> OTHER INFORMATION: Light chain variable region

<400> SEQUENCE: 133

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtc tgcaaagtgg ggtcccatca   180
aggttcagtg gcagtgggtc tgggacagat ttcactctca ccatcagcag tctgcaacct   240
gaagattttg caacttacta ctgtcaacag agttacagaa ccccgctcac tttcggcgga   300
gggaccaagg tggagatcaa a                                             321
```

<210> SEQ ID NO 134
<211> LENGTH: 384
<212> TYPE: DNA
<213> ORGANISM: Artificial Sequence
<220> FEATURE:
<223> OTHER INFORMATION: heavy chain variable region

<400> SEQUENCE: 134

```
caggtgcagt tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagaggaccc   300
tatctgtata gcagtggctg gtacgactac tactactacg gtatggacgt ctggggccaa   360
gggaccacgg tcaccgtctc ctca                                          384
```

<210> SEQ ID NO 135
<211> LENGTH: 321
<212> TYPE: DNA
<213> ORGANISM: Artificial Sequence
<220> FEATURE:
<223> OTHER INFORMATION: Light chain variable region

<400> SEQUENCE: 135

```
gacatccaga tgacccagtc tccatcctcc ctgtctgcat ctgtaggaga cagagtcacc    60
atcacttgcc gggcaagtca gatcattagc agctatttaa actggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagaa ccccgctcac tttcggcgga   300
gggaccaagg tggagatcaa a                                             321
```

<210> SEQ ID NO 136
<211> LENGTH: 348
<212> TYPE: DNA
<213> ORGANISM: Artificial Sequence
<220> FEATURE:
<223> OTHER INFORMATION: heavy chain variable region

<400> SEQUENCE: 136

```
caggtgcagc tgcaggagtc gggcccagga ctggtgaagc cttcggagac cctgtccctc    60
acctgcgctg tctctggtta ctccatcagc agtggttact actggggctg gatccggcag   120
ccccccaggga aggggctgga gtggattggg agtatctatc atagtgggag tacctcctac   180
aacccgtccc tcaggagtcg agtcaccata tcagtagaca cgtccaagaa ccagttctcc   240
```

```
ctgaagctga gctctgtgac cgccgcagac acggccgtgt attactgtgc gagagatgct    300
gggggctttg actactgggg ccagggaacc ctggtcaccg tctcctca                 348
```

<210> SEQ ID NO 137
<211> LENGTH: 321
<212> TYPE: DNA
<213> ORGANISM: Artificial Sequence
<220> FEATURE:
<223> OTHER INFORMATION: Light chain variable region

<400> SEQUENCE: 137

```
gacatccaga tgacccagtc tccttccacc ctgtctgcat ctgtaggaga cagagtcacc    60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttattg ctgccaacag tataatagtt attctcacac ttttggccag    300
gggaccaagc tggagatcaa a                                              321
```

<210> SEQ ID NO 138
<211> LENGTH: 357
<212> TYPE: DNA
<213> ORGANISM: Artificial Sequence
<220> FEATURE:
<223> OTHER INFORMATION: heavy chain variable region

<400> SEQUENCE: 138

```
caggtgcagc tgcaggagtc gggcccagga ctggtgaggc cttcggagac cctgtccctc    60
acctgcgctg tctctggata ctccatcagc agtggttact actggggctg gatccggcag    120
cccccaggga aggggctgga gtggattggg agtatctttc acagtgggaa tacctactac    180
aatccgtccc tcaagagtcg agtcatcgta tcaggagaca cgtccaagaa ccagttctcc    240
ctgaagctga gctctgtgac cgccgcagac acggccgtgt attactgtac gagagaaagt    300
tctgggttca atgtttttga catctggggc caagggacaa tggtcaccgt ctcttca       357
```

<210> SEQ ID NO 139
<211> LENGTH: 321
<212> TYPE: DNA
<213> ORGANISM: Artificial Sequence
<220> FEATURE:
<223> OTHER INFORMATION: Light chain variable region

<400> SEQUENCE: 139

```
gacatccaga tgacccagtc tccttccacc ctgtctgcat ctgtaggaga cagagtcacc    60
atcacttgcc gggccagtca gaatattggt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtacac ttttggccag    300
gggaccaagc tggagatcaa a                                              321
```

<210> SEQ ID NO 140
<211> LENGTH: 19
<212> TYPE: PRT
<213> ORGANISM: Artificial Sequence
<220> FEATURE:
<223> OTHER INFORMATION: CDR3

<400> SEQUENCE: 140

Gly Pro Tyr Leu Tyr Ser Ser Gly Trp Tyr Asp Tyr Tyr Tyr Gly
1               5                   10                  15

Met Asp Val

4-1BB ANTIBODY AND PREPARATION METHOD AND USE THEREOF

RELATED APPLICATIONS

This application is a national stage filing under 35 U.S.C. § 371 of international application number PCT/CN2018/114641, filed on Nov. 8, 2018, which claims the benefit of priority to Chinese Patent Application No. 201711099446.4, filed on Nov. 9, 2017. The entire contents of each of the prior applications are herein incorporated by reference.

SEQUENCE LISTING

This application contains a Sequence Listing that has been submitted in ASCII format via EFS-Web and is hereby incorporated by reference in its entirety. The ASCII copy is named "104775-657940-70005US00-Sequence-Listing_ST25.txt", is $70.8 \times 10^3$ bytes in size, and was created on May 5, 2020.

TECHNICAL FIELD

The present invention relates to the field of biomedicine, and more specifically to 4-1BB antibody and preparation method and use thereof.

BACKGROUND 4-1BB, also known as CD137, or TNFRF9, is a member of the TNF receptor family. 4-1BB is a type I transmembrane protein with a reading frame containing 255 amino acids (NCBI: NP_001552), consisting of an N-terminal signal peptide containing 17 amino acids, an extracellular domain of 169 amino acids, and a transmembrane domain of 27 amino acids and a C-terminal intracellular domain of 42 amino acid. The 4-1BB molecule is mainly expressed in activated T cells, NK cells, regulatory T cells, dendritic cells, monocytes, neutrophils and eosinophils, and endothelial cells of tumor vessels have also been reported to express 4-1BB.

During the activation of T cells, 4-1BB molecules can provide costimulatory signals. When the T cell receptor is exposed to the antigen, it will increase the expression of 4-1BB. The binding of 4-1BB to the ligand will cause the activation of the NFκB signaling pathway, resulting in the activation and proliferation of T cells, and 4-1BB can also inhibit the apoptosis of activated cells. It has been confirmed in animal models and in vitro experiments that anti-4-1BB activating monoclonal antibodies have anti-tumor activity. It can selectively cause the proliferation of CD8+ T cells, and up-regulate the expression of pro-inflammatory cytokine IFN-γ, and can enhance the killing effect of antigen-specific effector T cells, thereby promoting the removal of tumors. Anti-4-1BB activating monoclonal antibodies can also cause the expansion of NK cells and can increase the cytotoxic activity of CD8+ T cells through it. The anti-4-1BB agonistic antibodies can also cause upregulated expression of adhesion molecules in the endothelial cells of blood vessels in tumor cells, and promote the infiltration of activated T lymphocytes into tumor tissues.

In addition, in animal models, anti-4-1BB activating antibodies can also alleviate autoimmune diseases such as autoimmune encephalomyelitis, lupus-like syndrome, and collagen-induced arthritis.

At present, the existing 4-1BB antibodies in the art still have many deficiencies in antigen binding activity and activation of downstream signals of 4-1BB molecules and the like. There is no widely used 4-1BB antibody drug product, and development of 4-1BB activating antibodies is an urgent need for the treatment of cancer and autoimmune diseases.

SUMMARY OF THE INVENTION

The purpose of the present invention is to provide a high-affinity 4-1BB antibody and the preparation method and application thereof.

In a first aspect of the present invention, it provides a heavy chain variable region of an antibody, which comprises the following three complementary determining regions CDRs:

CDR1 as shown in SEQ ID NO: 2 or SEQ ID NO: 10;
CDR2 as shown in SEQ ID NO: 3 or SEQ ID NO: 11; and
CDR3 as shown in SEQ ID NO: 4 or SEQ ID NO: 12, wherein, any one of the above-mentioned amino acid sequences further comprises a derivative sequence that is optionally added, deleted, modified, and/or substituted with one amino acid and capable of retaining the binding affinity of 4-1BB.

In another preferred embodiment, the heavy chain variable region comprises the following three complementary determining regions CDRs:

CDR1 as shown in SEQ ID NO: 2;
CDR2 as shown in SEQ ID NO: 3; and
CDR3 as shown in SEQ ID NO: 4;
or,
CDR1 as shown in SEQ ID NO: 10;
CDR2 as shown in SEQ ID NO: 11; and
CDR3 as shown in SEQ ID NO: 12, wherein, any one of the above-mentioned amino acid sequences further comprises a derivative sequence that is optionally added, deleted, modified, and/or substituted with one amino acid and capable of retaining the 4-1BB binding affinity.

In another preferred embodiment, the amino acid sequence of the CDR3 comprises a derivative sequence optionally added, deleted, modified, and/or substituted with one amino acid and capable of retaining 4-1BB binding affinity.

In another preferred embodiment, the heavy chain variable region further comprises a human-derived FR region or a murine-derived FR region.

In another preferred embodiment, the heavy chain variable region has an amino acid sequence as shown in SEQ ID NO: 1 or SEQ ID NO: 9.

In a second aspect of the present invention, it provides a heavy chain of an antibody, having the heavy chain variable region according to the first aspect of the present invention.

In another preferred embodiment, the heavy chain of the antibody further comprises a heavy chain constant region.

In another preferred embodiment, the heavy chain constant region is derived from human, a murine or a rabbit.

In a third aspect of the present invention, it provides a light chain variable region of an antibody, which comprises the following three complementary determining regions CDRs:

CDR1' as shown in SEQ ID NO: 6 or SEQ ID NO: 14;
CDR2' as shown in SEQ ID NO: 7 or SEQ ID NO: 15; and
CDR3' as shown in SEQ ID NO: 8 or SEQ ID NO: 16.

In another preferred embodiment, the light chain variable region comprises the following three complementary determining regions CDRs:

CDR1' as shown in SEQ ID NO: 6;

CDR2' as shown in SEQ ID NO: 7; and
CDR3' as shown in SEQ ID NO: 8;
or,
CDR1' as shown in SEQ ID NO: 14;
CDR2' as shown in SEQ ID NO: 15; and
CDR3' as shown in SEQ ID NO: 16.

In another preferred embodiment, the light chain variable region further comprises a human-derived FR region or a murine-derived FR region.

In another preferred embodiment, the light chain variable region has an amino acid sequence as shown in SEQ ID NO: 5 or SEQ ID NO: 13.

In a fourth aspect of the present invention, it provides a light chain of an antibody, having the light chain variable region according to the third aspect of the present invention.

In another preferred embodiment, the light chain of the antibody further comprises a light chain constant region.

In another preferred embodiment, the light chain constant region is derived from human, a murine or a rabbit.

In a fifth aspect of the present invention, it provides an antibody having:
(1) a heavy chain variable region according to the first aspect of the present invention; and/or
(2) a light chain variable region according to the third aspect of the present invention;
or an antibody having: a heavy chain according to the second aspect of the present invention; and/or a light chain according to the fourth aspect of the present invention.

In another preferred embodiment, the $EC_{50}$ of the affinity of the antibody for NF κ B transcription factor is 0.1-5 nM.

In another preferred embodiment, the $EC_{50}$ of the affinity of the antibody after cross-linking for the NF κ B transcription factor is 0.4-1 nM.

In another preferred embodiment, the cross-linking means that the antibody can be enriched by binding to other media through its own Fc segment, wherein the other media comprises media specifically binds the antibody Fc segment, including but not limited to anti-Fc antibody and cell surface Fc receptor.

In another preferred embodiment, the NF κ B transcription factor is located downstream of the human 4-1BB protein.

In another preferred embodiment, the antibody is selected from animal-derived antibodies, chimeric antibodies, humanized antibodies, and a combination thereof.

In another preferred embodiment, the antibody is a double-chain antibody or a single-chain antibody.

In another preferred embodiment, the antibody is a monoclonal antibody.

In another preferred embodiment, the antibody is a partially or fully humanized monoclonal antibody.

In another preferred embodiment, the heavy chain variable region sequence of the antibody is shown as SEQ ID NO: 1; and the light chain variable region sequence of the antibody is shown as SEQ ID NO: 5.

In another preferred embodiment, the heavy chain variable region sequence of the antibody is shown as SEQ ID NO: 9; and the light chain variable region sequence of the antibody is shown as SEQ ID NO: 13.

In another preferred embodiment, the antibody is in the form of a drug conjugate.

In a sixth aspect of the present invention, it provides a recombinant protein having:
(i) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; and
(ii) an optional tag sequence to facilitate expression and/or purification.

In another preferred embodiment, the tag sequence comprises a 6His tag.

In another preferred embodiment, the recombinant protein (or polypeptide) includes a fusion protein.

In another preferred embodiment, the recombinant protein is a monomer, a dimer, or a polymer.

In a seventh aspect of the present invention, it provides a chimeric antigen receptor (CAR) construct, wherein the scFV segment of the monoclonal antibody antigen binding region of the CAR construct is a binding region that specifically binds to 4-1BB, and the scFv has the heavy chain variable region according to the first aspect of the present invention and the light chain variable region according to the third aspect of the present invention.

In an eighth aspect of the present invention, it provides a recombinant immune cell, wherein the immune cell expresses an exogenous CAR construct as described in the seventh aspect of the present invention.

In another preferred embodiment, the immune cell is selected from the group consisting of an NK cell and a T cell.

In another preferred embodiment, the immune cell is derived from human or a non-human mammal (such as a mouse).

In a ninth aspect of the present invention, it provides an antibody-drug conjugate, wherein the antibody-drug conjugate comprises:
(a) an antibody portion selected from the group consisting of the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, and a combination thereof; and
(b) a coupling portion coupled to the antibody portion, wherein the coupling portion is selected from the group consisting of a detectable label, a drug, a toxin, a cytokine, a radionuclide, an enzyme, and a combination thereof.

In another preferred embodiment, the antibody portion and the coupling portion are coupled by a chemical bond or a linker.

In a tenth aspect of the present invention, it provides a use of an active ingredient selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, the recombinant protein according to the sixth aspect of the present invention, the immune cell according to the eighth aspect of the present invention, the antibody-drug conjugate according to the ninth aspect of the present invention, and a combination thereof, wherein the active ingredient is used for (a) the preparation of a detection reagent or a kit; and/or (b) the preparation of a drug for preventing and/or treating a 4-1BB related disease.

In another preferred embodiment, the 4-1BB related disease is selected from the group consisting of a cancer, autoimmune diseases, viral infections, graft-versus-host diseases, inflammatory diseases, immune diseases, and a combination thereof.

In another preferred embodiment, the cancer includes a solid tumor and a blood cancer.

In another preferred embodiment, the solid tumor is selected from the group consisting of bladder cancer, biliary tract cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal carcinoma, saliva cancer, gastric cancer, thymic epithelial cancer, and thyroid cancer, and a combination thereof.

In another preferred embodiment, the autoimmune disease is selected from the group consisting of systemic lupus erythematosus, rheumatoid arthritis, ulcerative colitis, type I diabetes, psoriasis, multiple sclerosis, and a combination thereof.

In another preferred embodiment, the antibody is in the form of a drug conjugate (ADC).

In another preferred embodiment, the detection reagent or kit is used to diagnose 4-1BB-related diseases.

In another preferred embodiment, the detection reagent or kit is used to detect 4-1BB in a sample.

In another preferred embodiment, the detection reagent is a test piece.

In an eleventh aspect of the present invention, it provides a pharmaceutical composition comprising:

(i) an active ingredient selected from the group consisting of the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the immune cell according to the eighth aspect of the present invention, the antibody drug conjugate according to the ninth aspect of the present invention, and a combination thereof; and (ii) a pharmaceutically acceptable carrier.

In another preferred embodiment, the pharmaceutical composition is a liquid preparation.

In another preferred embodiment, the pharmaceutical composition is an injection.

In a twelfth aspect of the present invention, it provides a polynucleotide encoding a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention; and (2) the recombinant protein according to the sixth aspect of the present invention;

(3) the CAR construct according to the seventh aspect of the present invention.

In another preferred embodiment, the nucleic acid encoding the heavy chain variable region is shown as SEQ ID NO: 106 and/or the nucleic acid encoding the light chain variable region is shown as SEQ ID NO: 107.

In another preferred embodiment, the nucleic acid encoding the heavy chain variable region is shown as SEQ ID NO: 108 and/or the nucleic acid encoding the light chain variable region is shown as SEQ ID NO: 109 in the sequence listing.

In a thirteenth aspect of the present invention, it provides a vector containing the polynucleotide according to the twelfth aspect of the present invention.

In another preferred embodiment, the vector includes: a bacterial plasmid, a bacteriophage, a yeast plasmid, a plant cell virus, a mammalian cell virus such as adenovirus, retrovirus, or other vectors.

In a fourteenth aspect of the present invention, it provides a genetically engineered host cell containing the vector according to the thirteenth aspect of the present invention or with the polynucleotide according to the twelfth aspect of the present invention integrated in the genome.

In a fifteenth aspect of the present invention, it provides a in vitro method for detecting 4-1BB in a sample (including diagnostic or non-diagnostic detection), comprising the steps of:

(1) contacting the sample with the antibody according to the fifth aspect of the present invention in vitro;

(2) detecting whether an antigen-antibody complex is formed, wherein the formation of the complex indicates the presence of 4-1BB in the sample.

In a sixteenth aspect of the present invention, it provides a detection plate, wherein the detection plate comprises: a substrate (supporting plate) and a test strip, wherein the test strip contains the antibody according to the fifth aspect of the present invention or the immunoconjugate according to the ninth aspect of the present invention.

In a seventeenth aspect of the present invention, it provides a kit, wherein the kit comprises:

(1) a first container containing the antibody according to the fifth aspect of the invention; and/or (2) a second container containing a secondary antibody against the antibody according to the fifth aspect of the present invention;

or, the kit comprises the detection plate according to the sixteenth aspect of the present invention.

In an eighteenth aspect of the present invention, it provides a method for preparing a recombinant polypeptide, wherein the method comprises:

(a) cultivating the host cell according to the fourteenth aspect of the present invention under conditions suitable for expression;

(b) isolating the recombinant polypeptide from the culture, wherein the recombinant polypeptide is the antibody according to the fifth aspect of the present invention or the recombinant protein according to the sixth aspect of the present invention.

In a nineteenth aspect of the present invention, it provides a method for treating 4-1BB-related diseases, wherein the method comprises: administering the antibody according to the fifth aspect of the present invention, an antibody-drug conjugate of the antibody, or a CAR-T cell expressing the antibody, or a combination thereof to a subject in need.

In another aspect of the present invention, it provides a method for detecting a cell overexpressing 4-1BB protein, comprising the steps of: in vitro contacting the antibody according to the fifth aspect of the present invention with a test sample, thereby detecting the binding of the antibody to the test sample.

In another aspect of the present invention, it provides a composition for detecting a cell overexpressing 4-1BB protein, comprising the antibody according to the fifth aspect of the present invention as an active ingredient.

The technical problem to be solved by the present invention is to overcome the shortage of the current lack of 4-1BB antibody, especially the humanized 4-1BB antibody, to provide a 4-1BB antibody with a strong specificity and high biological activity and a preparation method thereof. The 4-1BB antibody has high affinity with human and monkey-derived 4-1BB protein, and can activate the downstream signal of 4-1BB molecule, and can significantly increase the expression level of IFN-γ and IL-2 in human mixed lymphocyte or T lymphocyte reaction.

The present invention first prepares human-derived 4-1BB as an immunogen, and uses the human-derived antibody transgenic mouse technology to prepare fully human-derived antibodies to obtain the lead antibody of the 4-1BB antibody, and then through the preliminary production, purification and identification of the lead antibody, the antibodies with excellent biological levels that can effectively stimulate the 4-1BB receptor and activate its downstream signals, resulting in a significant increase in the expression levels of IFN-γ and IL-2 in human T lymphocyte responses are obtained, and then the amino acid sequences of the heavy chain variable region and the light chain variable region of the 4-1BB antibody are obtained and sequenced by molecular biology method.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
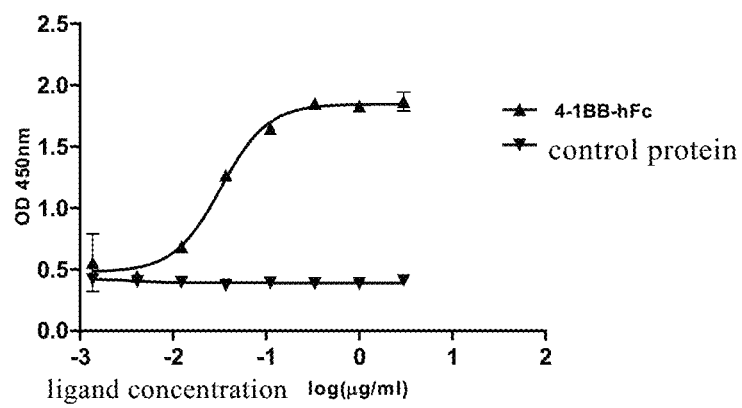
FIG. 1 shows the binding activity of the 4-1BB-hFc protein to the fusion protein of his-muCD8a-4-1BBL.

After extensive and intensive research, the present inventor has for the first time unexpectedly discovered a 4-1BB antibody with high affinity and specificity, and obtained a fully humanized antibody based on the antibody. The antibody of the present invention has high affinity for 4-1BB protein, and can effectively activate the downstream signal of 4-1BB, and can significantly increase the expression levels of IFN-γ and IL-2 in human mixed lymphocytes or T lymphocytes, and can be used to treat cancer and autoimmune diseases. On this basis, the present invention has been completed.

Terms

As used herein, the term "conjugate" refers to a soluble receptor or a fragment thereof or an analogue thereof, or an antibody or a fragment thereof or an analogue thereof that is capable of binding to a target.

As used herein, the terms "4-1BB conjugate", "4-1BB antibody", "anti-4-1BB antibody", and "antibody of the present invention" have the same meaning and refer to an antibody or a fragment thereof or an analogue thereof that can specifically recognize 4-1BB and bind to 4-1BB.

As used herein, the terms "administration" and "treatment" refer to the application of exogenous drugs, therapeutic agents, diagnostic agents, or compositions to animals, humans, subjects, cells, tissues, organs, or biological fluids. "Administration" and "treatment" may refer to treatment, pharmacokinetics, diagnosis, research and experimental methods. The treatment of cells includes the contact of reagents with cells, the contact of reagents with fluids, and the contact of fluids with cells. "Administration" and "treatment" also mean treatment in vitro and ex vivo by an agent, diagnosis, binding composition, or by another cell. When "treatment" is applied to humans, animals or research subjects, it refers to therapeutic treatments, prevention or preventive measures, research and diagnosis; including the contact of 4-1BB conjugate with a human or animal, subject, cell, tissue, physiological compartment or a physiological fluid.

As used herein, the term "treatment" refers to the administration of an internal or external therapeutic agent to a patient, comprising any one of the 4-1BB conjugates of the present invention and a composition thereof, and the patient has one or more symptoms of the disease, and the therapeutic agent is known to have a therapeutic effect on these symptoms. Generally, the patient is administered with an amount of a therapeutic agent (a therapeutically effective amount) effective to relieve symptoms of one or more diseases.

As used herein, the term "optional" or "optionally" means that the subsequently described event or circumstance can occur, but not necessarily.

Antibody

As used herein, the term "antibody" refers to an immunoglobulin, which is a tetrapeptide chain structure formed by two identical heavy chains and two identical light chains connected by interchain disulfide bonds. The immunoglobulin heavy chain constant regions have different amino acid compositions and arrangements, so that the antigenicities are also different. According to this, immunoglobulins can be divided into five categories, or called different types of immunoglobulins, namely IgM, IgD, IgG, IgA and IgE, and the heavy chain constant regions corresponding to the different types of immunoglobulins are called α, δ, ε, γ, and μ, respectively. IgG represents the most important class of immunoglobulins. Due to differences in chemical structure and biological functions, it can be divided into 4 subclasses: IgG1, IgG2, IgG3, and IgG4. The light chain is divided into κ or λ chains by different constant regions. The subunit structures and three-dimensional configurations of different classes of immunoglobulins are well known to those skilled in the art.

The sequence of about 110 amino acids near the N-terminus of the antibody heavy and light chains varies greatly and is a variable region (V region); the remaining amino acid sequences near the C-terminus are relatively stable and are constant regions (C region). The variable region includes three hypervariable regions (HVR) and four relatively conserved FR regions (FR). The amino acid sequences of the four FRs are relatively conservative and do not directly participate in the binding reaction. The three hypervariable regions determine the specificity of the antibody, also known as the complementarity determining regions (CDR). Each light chain variable region (LCVR) and heavy chain variable region (HCVR) are composed of 3 CDR regions and 4 FR regions, and the sequence from the amino terminal to the carboxy terminal is FR1, CDR1, FR2, CDR2, FR3, CDR3, FR4. The three CDR regions of the light chain, namely light chain hypervariable regions (LCDR), refer to LCDR1, LCDR2, and LCDR3; the three CDR regions of the heavy chain, namely heavy chain hypervariable regions (HCDR), refer to HCDR1, HCDR2, and HCDR3. The number and position of the CDR amino acid residues of the LCVR and HCVR regions of the antibody or antigen-binding fragment in the present invention comply with the known Kabat numbering rules (LCDR1-3, HCDR2-3), or the numbering rules for kabat and chothia (HCDR1). The four FR regions in the natural heavy and light chain variable regions are roughly in the β-fold configuration, connected by the three CDRs that form the connecting loop, and in some cases part of the β-folded structure may be formed. The CDRs in each chain are closely together through the FR region and together with the CDRs of the other chain to form the antigen-binding site of the antibody. The amino acid sequences of antibodies of the same type can be compared to determine which amino acids constitute the FR or CDR regions. The constant regions are not directly involved in the binding of antibodies to antigens, but they exhibit different effector functions, such as antibody-dependent cytotoxicity involved in antibodies.

As used herein, the term "antigen-binding fragment" refers to an Fab fragment, an Fab' fragment, an F(ab') 2 fragment, or a single Fv fragment having an antigen-binding activity. Fv antibodies contain antibody heavy chain variable regions and light chain variable regions, but no constant region, and have the smallest antibody fragments of all antigen binding sites. Generally, Fv antibodies also contain a polypeptide linker between the VH and VL domains, and can form the structure required for antigen binding.

As used herein, the term "antigenic determinant" refers to a discrete three-dimensional site on an antigen that is recognized by an antibody or antigen-binding fragment of the present invention.

The present invention includes not only whole antibodies, but also fragments of antibodies with immunological activity or fusion proteins formed by antibodies and other sequences. Therefore, the present invention also includes fragments, derivatives and analogues of the antibodies.

In the present invention, antibodies include murine, chimeric, humanized, or fully human antibodies prepared by techniques well known to those skilled in the art. Recombinant antibodies, such as chimeric and humanized monoclonal antibodies, including human and non-human parts, can be prepared using DNA recombination techniques well known in the art.

As used herein, the term "monoclonal antibody" refers to an antibody secreted from a clone derived from a single cell. Monoclonal antibodies are highly specific and target a single epitope. The cells may be eukaryotic, prokaryotic or phage cloned cell lines.

As used herein, the term "chimeric antibody" is a chimeric gene spliced from a V region gene of a murine antibody and a C region gene of a human antibody, and then inserted into a vector to transfect an antibody molecule expressed by a host cell. It not only retains the high specificity and affinity of the parent murine antibody, but also enables its human Fc segment to effectively mediate the biological effect function.

As used herein, the term "humanized antibody" is a modification of the variable region of the mouse antibody of the present invention, having a CDR region derived from (or substantially derived from) a non-human antibody (preferably a mouse monoclonal antibody), and FR regions and constant regions derived essentially from human-derived antibody sequences; that is, the CDR region sequences of mouse antibodies are grafted onto different types of human germline antibody framework sequences. Because CDR sequences are responsible for most antibody-antigen interactions, expression vectors can be constructed to express recombinant antibodies that mimic the properties of specific naturally occurring antibodies.

In the present invention, the antibody may be monospecific, bispecific, trispecific, or more multispecific.

In the present invention, the antibody of the present invention also includes conservative variants, which means that at most 10, preferably at most 8, more preferably at most 5, most preferably at most 3 amino acids are replaced by amino acids with similar or close properties to form a polypeptide, compared with the amino acid sequence of the antibody of the present invention. These conservative variant peptides are preferably produced by amino acid substitution according to Table A.

TABLE A

| initial residue | representative substitution | preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-4-1BB Antibody 4-1BB, also known as CD137, or TNFRF9, is a member of the TNF receptor family. 4-1BB is a type I transmembrane protein with a reading frame containing 255 amino acids (NCBI: NP_001552), consisting of an N-terminal signal peptide containing 17 amino acids, an extracellular region of 169 amino acids, and a transmembrane region of 27 amino acids and a 42-amino acid C-terminal intracellular region. The specific sequence is shown as SEQ ID NO: 22 in the present invention.

As used herein, the term "4-1BB" generally refers to a natural or recombinant human 4-1BB, as well as a non-human homolog of human 4-1BB. Unless otherwise indicated, the molecular weight of the 4-1BB homodimer is used to calculate the molar concentration of 4-1BB.

As used herein, the term "human 4-1BB" includes the mature form of human 4-1BB protein and its natural variants and polymorphisms.

The present invention provides a high affinity antibody against 4-1BB, which includes a heavy chain and a light chain, wherein the heavy chain contains an amino acid sequence of a heavy chain variable region (VH), and the light chain contains an amino acid sequence of a light chain variable region (VL).

Preferably, the each CDR of the heavy chain variable region (VH) amino acid sequence and the light chain variable region (VL) amino acid sequence are selected from the group consisting of:

a1) SEQ ID NO: 2 or SEQ ID NO: 10;
a2) SEQ ID NO: 3 or SEQ ID NO: 11;
a3) SEQ ID NO: 4 or SEQ ID NO: 12;
a4) SEQ ID NO: 6 or SEQ ID NO: 14;
a5) SEQ ID NO: 7 or SEQ ID NO: 15;
a6) SEQ ID NO: 8 or SEQ ID NO: 16;
a7) sequences with addition, deletion, modification and/or substitution of at least one (such as 1-5, 1-3, preferably 1-2, more preferably 1) amino acid in any one of the above amino acid sequences and have 4-1BB binding affinity.

In another preferred embodiment, the sequence formed by the addition, deletion, modification and/or substitution of at least one amino acid sequence preferably has a homology of at least 80%, preferably at least 90%, and more preferably at least 95%, most preferably at least 99% of the amino acid sequence.

Preferably, the above-mentioned amino acid sequence numbers are shown in Table 1.

52F4G2, 118F3A2, 170D7F2, 172E3E3, 178D10D11, 182A5B3, 100F3C4, 119B6G5, 258F5A8, 259G10E11, 263A11E3, 289B6G6. Since their performances were lower than those of clones 57B3D10 and 113F6C6, no further experiments were conducted. For detailed experimental results, please refer to the examples.

The antibody of the present invention may be one or more of an antibody full-length protein, an antigen-antibody binding domain protein fragment, a bispecific antibody, a multispecific antibody, a single chain antibody fragment (scFv), a single-domain antibody (sdAb), single-domain antibody, and monoclonal antibodies or polyclonal antibodies prepared from the above antibodies. The monoclonal antibody can be developed in various ways and technologies, including hybridoma technology, phage display technology, single lymphocyte gene cloning technology, etc. The mainstream is to prepare monoclonal antibodies from wild-type or transgenic mice through hybridoma technology.

The antibody full-length protein is a conventional antibody full-length protein in the art, which includes a heavy chain variable region, a light chain variable region, a heavy chain constant region, and a light chain constant region. The heavy chain variable region and light chain variable region of the protein, together with the human heavy chain constant region and the human light chain constant region, constitute a full human antibody full-length protein. Preferably, the antibody full length protein is IgG1, IgG2, IgG3 or IgG4.

The single chain antibody is a conventional single chain antibody in the art, which includes a heavy chain variable region, a light chain variable region and a short peptide of 15-20 amino acids.

The antigen-antibody binding domain protein fragments are conventional antigen-antibody binding domain protein fragments in the art, which include a light chain variable region, a light chain constant region, and an Fd segment of a heavy chain constant region. Preferably, the protein fragments of the antigen-antibody binding domain are Fab and F(ab').

The single domain antibody is a conventional single domain antibody in the art, which includes a heavy chain variable region and a heavy chain constant region.

The single-domain antibody is a conventional single-domain antibody in the art, which includes only a heavy chain variable region.

Specifically, the antibody of the present invention may be a double-chain or single-chain antibody, and may be selected

TABLE 1

| | 4-1BB antibody protein sequence number | | | | | | | |
|---|---|---|---|---|---|---|---|---|
| | Heavy chain protein | | | | Light chain protein | | | |
| Clone number | Variable region | CDR1 | CDR2 | CDR3 | Variable region | CDR1 | CDR2 | CDR3 |
| 57B3D10 | 1 | 2 | 3 | 4 | 5 | 6 | 7 | 8 |
| 113F6C6 | 9 | 10 | 11 | 12 | 13 | 14 | 15 | 16 |

Wherein, the numbers in Table 1 are the numbers of "SEQ ID NO" in the sequence list, such as the amino acid sequence of the heavy chain protein variable region of 57B3D10 is shown as SEQ ID NO: 1, while the amino acid sequence of the CDR1 domain in the variable region of the heavy chain protein of 57B3D10 is shown as SEQ ID NO: 2.

In fact, during the antibody screening process, the inventors also conducted relevant experiments on the 4-1BB antibody of clone number of 11H10C9, 15G10D4, 23G3B8, from animal-derived antibodies, chimeric antibodies, and humanized antibodies, more preferably humanized antibodies, human-animal chimeric antibodies, and more preferably a fully humanized antibody.

The antibody derivative of the present invention may be any one or more of single chain antibodies, and/or antibody fragments, such as: Fab, Fab', (Fab')$_2$ or other known antibody derivatives in the art, as well as IgA, IgD, IgE, IgG and IgM antibodies or other subtype antibodies.

Wherein, the animal is preferably a mammal, such as a mouse.

The antibody of the present invention may be a murine-derived antibody, chimeric antibody, humanized antibody, CDR grafted and/or modified antibody targeting human 4-1BB.

In a preferred embodiment of the present invention, any one or several sequences of the above SEQ ID NO: 2, 3 and 4, and SEQ ID NO: 6, 7 and 8, and the above sequences with at least one amino acid added, deleted, modified, and/or substituted and have 4-1BB binding affinity, locate in the CDR region of the heavy chain variable region (VH).

In a preferred embodiment of the present invention, any one or several sequences of the above SEQ ID NO: 10, 11 and 12, and SEQ ID NO: 14, 15 and 16, and the above sequences with at least one amino acid added, deleted, modified, and/or substituted and have 4-1BB binding affinity, locate in the CDR region of the light chain variable region (VL).

In a more preferred embodiment of the present invention, VH CDR1, CDR2, CDR3 are independently selected from any one or several sequences of SEQ ID NO: 2, 3 and 4, and SEQ ID NO: 6, 7 and 8 and the above sequences with at least one amino acid added, deleted, modified and/or substituted and have 4-1BB binding affinity; VL CDR1, CDR2, CDR3 are each independently selected from any one or several sequences of SEQ ID NO: 10, 11 and 12, and SEQ ID NO: 14, 15 and 16, and the above sequences with at least one amino acid added, deleted, modified and/or substituted and have 4-1BB binding affinity.

In the above content of the present invention, the number of added, deleted, modified and/or substituted amino acids is preferably not more than 30% of the total number of amino acids in the original amino acid sequences, more preferably not more than 20%, more preferably 1-15%, more preferably 1-10%.

In the present invention, the number of the added, deleted, modified and/or substituted amino acids is usually 1, 2, 3, 4 or 5, preferably 1-3, more preferably 1-2, most preferably, 1.

Polynucleotide

The present invention also provides a nucleic acid encoding the above-mentioned polypeptide.

Preferably, the nucleic acid encoding the heavy chain variable region is shown as SEQ ID NO: 106 in the sequence listing or SEQ ID NO: 108 in the sequence listing; and/or the nucleotide sequence of the nucleic acid encoding the light chain variable region is shown as SEQ ID NO: 107 in the sequence listing or SEQ ID NO: 109 in the sequence listing.

More preferably, the nucleic acid encoding the heavy chain variable region is shown as SEQ ID NO: 106 in the sequence listing, and the nucleic acid encoding the light chain variable region is shown as SEQ ID NO: 107 in the sequence listing; the nucleic acid encoding the heavy chain variable region is shown as SEQ ID NO: 108 in the sequence listing, and the nucleic acid encoding the light chain variable region is shown as SEQ ID NO: 109 in the sequence listing.

The numbering of the above nucleotide sequences is shown in Table 2:

TABLE 2 numbers of 4-1BB antibody gene sequences

| Clone number | Heavy chain variable region | Light chain variable region |
|---|---|---|
| 57B3D10 | 106 | 107 |
| 113F6C6 | 108 | 109 |

The numbers in Table 2 are the numbers of "SEQ ID NO." in the sequence listing. For example, the nucleotide sequence encoding the variable region of the heavy chain protein of 57B3D10 is SEQ ID NO: 106 in the sequence listing.

Wherein, the nucleotide sequence encoding the CDR1 domain in the heavy chain protein variable region of 57B3D10 is from position 91 to position 105 in SEQ ID NO: 106 of the sequence listing;

the nucleotide sequence encoding the CDR2 domain in the heavy chain protein variable region of 57B3D10 is from position 148 to position 195 in SEQ ID NO: 106 of the sequence listing;

the nucleotide sequence encoding the CDR3 domain in the heavy chain protein variable region of 57B3D10 is from position 292 to position 342 in SEQ ID NO: 106 of the sequence listing;

the nucleotide sequence encoding the CDR1 domain of the light chain protein variable region of 57B3D10 is from position 67 to position 102 in SEQ ID NO: 107 of the sequence listing;

the nucleotide sequence encoding the CDR2 domain of the light chain protein variable region of 57B3D10 is from position 148 to position 168 in SEQ ID NO: 107 of the sequence listing;

the nucleotide sequence encoding the CDR3 domain of the light chain protein variable region of 57B3D10 is from position 265 to position 288 in SEQ ID NO: 107 of the sequence listing;

the nucleotide sequence encoding the CDR1 domain in the heavy chain protein variable region of 113F6C6 is from position 91 to position 105 in SEQ ID NO: 108 of the sequence listing;

the nucleotide sequence encoding the CDR2 domain in the heavy chain protein variable region of 113F6C6 is from position 148 to position 198 in SEQ ID NO: 108 of the sequence listing;

the nucleotide sequence encoding the CDR3 domain in the heavy chain protein variable region of 113F6C6 is from position 295 to position 351 in SEQ ID NO: 108 of the sequence listing;

the nucleotide sequence encoding the CDR1 domain in the light chain protein variable region of 113F6C6 is from position 70 to position 102 in SEQ ID NO: 109 of the sequence listing;

the nucleotide sequence encoding the CDR2 domain in the light chain protein variable region of 113F6C6 is from position 148 to position 168 in SEQ ID NO: 109 of the sequence listing;

the nucleotide sequence encoding the CDR3 domain in the light chain protein variable region of 113F6C6 is from position 265 to position 291 in SEQ ID NO: 109 of the sequence listing;

the preparation method of the nucleic acid is a conventional preparation method in the art, and preferably includes the following steps: obtaining a nucleic acid molecule encoding the above protein by gene cloning technology, or obtaining a nucleic acid molecule encoding the above protein by artificial full sequence synthesis.

Those skilled in the art know that the nucleotide sequence encoding the amino acid sequences of the above-mentioned proteins may be appropriately substituted, deleted, altered, inserted, or added to provide a polynucleotide homolog. The homologue of the polynucleotide in the present invention can be prepared by replacing, deleting, or adding one or more bases of the gene encoding the protein sequence within the range of maintaining antibody activity.

Preparation for the Antibody

Any method suitable for producing monoclonal antibodies can be used to produce the anti-4-1BB antibody of the present invention. For example, animals can be immunized with linked or naturally occurring 4-1BB homodimer or fragments thereof. Appropriate immunization methods can be used, including adjuvants, immunostimulants, repeated booster immunizations, and one or more routes can be used.

Any suitable form of 4-1BB can be used as an immunogen (antigen) for generating non-human antibodies specific for 4-1BB, and screening the biological activity of the antibodies. The activating immunogen can be full-length mature human 4-1BB, including natural homodimers, or peptides containing single/multiple epitopes. The immunogen can be used alone or in combination with one or more immunogenicity enhancers known in the art. Immunogens can be purified from natural sources or produced in genetically modified cells. The DNA encoding the immunogen may be genomic or non-genomic in origin (e.g., cDNA). Suitable genetic vectors can be used to express DNA encoding immunogens, including, but not limited to, adenovirus vectors, adeno-associated virus vectors, baculovirus vectors, plasmids, and non-viral vectors.

An exemplary method for producing the anti-human 4-1BB antibody of the present invention is described in Example 1.

The fully humanized antibody can be selected from any kind of immunoglobulin, including IgM, IgD, IgG, IgA and IgE. In the present invention, the antibody is an IgG antibody, and the IgG4 subtype is used. Screening of antibodies with the biological assays described in the examples below makes it easy to optimize the necessary constant domain sequences to produce the desired biological activity.

Similarly, any type of light chain can be used in the compounds and methods herein. In particular, κ, λ chains or variants thereof can be used in the compounds and methods of the present invention.

An exemplary method of humanizing the anti-human 4-1BB antibody of the present invention is described in Example 3.

The sequences of the DNA molecule of the antibody or fragment thereof of the present invention can be obtained by conventional techniques, such as PCR amplification or genomic library screening. In addition, the coding sequences of the light chain and the heavy chain can be fused together to form a single chain antibody.

Once the relevant sequence is obtained, the relevant sequence can be obtained in large quantities by the recombination method. This is usually done by cloning it into a vector, then transferring it into a cell, and then isolating the relevant sequence from the proliferated host cells by conventional methods.

In addition, synthetic methods can be used to synthesize the relevant sequences, especially when the length of the fragments is short. Generally, a long sequence can be obtained by synthesizing multiple small fragments and then connecting them. This DNA sequence can then be introduced into various existing DNA molecules (or such as vectors) and cells known in the art.

The present invention also relates to vectors containing the appropriate DNA sequence as described above and an appropriate promoter or control sequence. These vectors can be used to transform appropriate host cells so that they can express proteins.

The host cell is a various host cell conventional in the art, as long as it can satisfy the above-mentioned recombinant expression vector to stably replicate itself, and the nucleic acid carried can be effectively expressed. Specifically, the host cell may be a prokaryotic cell, such as a bacterial cell; or a lower eukaryotic cell, such as a yeast cell; or a higher eukaryotic cell, such as a mammalian cell. Preferred animal cells include (but are not limited to): CHO-S, CHO-K1, HEK-293 cells.

Preferred host cells include *E. coli* TG1 or BL21 cells (expressing single chain antibodies or Fab antibodies), or CHO-K1 cells (expressing full-length IgG antibodies).

The steps of transforming host cells with recombinant DNA described in the present invention can be performed by techniques well known in the art. The obtained transformant can be cultured by a conventional method, and the transformant expresses the polypeptide encoded by the gene of the present invention. Depending on the host cell used, it is cultured under conventional conditions using conventional media.

Generally, the transformed host cells are cultured under conditions suitable for expression of the antibody of the present invention. Then conventional immunoglobulin purification steps, such as protein A-Sepharose, hydroxyapatite chromatography, gel electrophoresis, dialysis, ion exchange chromatography, hydrophobic chromatography, molecular sieve chromatography, or affinity chromatography and other conventional separation and purification means well known to the silled in the art are used to purify the antibodies of the present invention.

The obtained monoclonal antibody can be identified by conventional means. For example, the binding specificity of monoclonal antibodies can be determined by immunoprecipitation or in vitro binding tests (such as radioimmunoassay (RIA) or enzyme-linked immunosorbent assay (ELISA)).

Uses

The present invention provides a use of the antibody of the present invention, for example, for the preparation of a diagnostic preparation, or the preparation of a medicament for the prevention and/or treatment of 4-1BB-related diseases. The 4-1BB-related diseases include cancers, autoimmune diseases, viral infections, graft-versus-host diseases, inflammatory diseases, immune diseases, and a combination thereof. Wherein, the cancers include solid tumors and blood cancers, and the solid tumors are selected from the group consisting of bladder cancer, biliary tract cancer, brain cancer, breast cancer, colon cancer, esophageal cancer, gastric cancer, glioma, head cancer, leukemia, liver cancer, lung cancer, lymphoma, myeloma, neck cancer, ovarian cancer, melanoma, pancreatic cancer, renal cancer, salivary cancer, gastric cancer, thymic epithelial cancer, and thyroid cancer, and a combination thereof; the autoimmune diseases include: systemic lupus erythematosus, rheumatoid arthritis, ulcerative colitis, type I diabetes, psoriasis, multiple sclerosis, and a combination thereof.

Pharmaceutical Composition

The present invention also provides a composition. In a preferred embodiment, the composition is a pharmaceutical composition, which contains the above-mentioned antibody or an active fragment thereof or a fusion protein thereof or an ADC thereof or a corresponding CAR-T cell, and a pharmaceutically acceptable carrier. Generally, these substances can be formulated in a non-toxic, inert and pharmaceutically acceptable aqueous carrier medium, wherein the pH is usually about 5-8, preferably about 6-8, although the pH value may vary depending on the nature of the substance being formulated and the condition to be treated. The formulated pharmaceutical composition can be administered by conventional routes, including (but not limited to): intratumoral, intraperitoneal, intravenous, or topical administration.

The antibody of the present invention may also be used for cell therapy by expressing a nucleotide sequence in a cell, for example, the antibody is used for chimeric antigen receptor T cell immunotherapy (CAR-T) and the like.

The pharmaceutical composition of the present invention can be directly used to bind 4-1BB protein molecules, and thus can be used to prevent and treat 4-1BB-related diseases. In addition, other therapeutic agents can be used simultaneously.

The pharmaceutical composition of the present invention contains a safe and effective amount (such as 0.001-99 wt %, preferably 0.01-90 wt %, more preferably 0.1-80 wt %) of the above-mentioned monoclonal antibody (or its conjugate) of the present invention and a pharmaceutical acceptable carrier or excipient. Such carrier includes (but is not limited to): saline, buffer, glucose, water, glycerin, ethanol, and a combination thereof. The pharmaceutical preparation should match the mode of administration. The pharmaceutical composition of the present invention can be prepared in the form of an injection, for example, prepared by a conventional method using physiological saline or an aqueous solution containing glucose and other adjuvants. Pharmaceutical compositions such as injections and solutions are preferably manufactured under sterile conditions. The amount of active ingredient administered is a therapeutically effective amount, for example, about 1 microgram/kg body weight to about 100 mg/kg body weight per day. In addition, the polypeptide of the present invention can be used together with other therapeutic agents.

When using a pharmaceutical composition, a safe and effective amount of the pharmaceutical composition is applied to mammals, wherein the safe and effective amount is usually at least about 10 μg/kg body weight, and in most cases does not exceed about 50 mg/kg body weight. Preferably the dose is about 10 micrograms/kg body weight to about 20 mg/kg body weight. Of course, the specific dosage should also consider factors such as the route of administration, the patient's health status, etc., which are within the skills of skilled physicians.

Detection Uses and Kits

The antibodies of the present invention can be used in the detection applications, for example, for testing samples, thereby providing diagnostic information.

In the present invention, the samples (specimen) used include cells, tissue samples and biopsy specimens. The term "biopsy" used in the present invention shall include all kinds of biopsies known to those skilled in the art. Therefore, the biopsy used in the present invention may include, for example, a tissue sample prepared by an endoscopic method or a puncture or needle biopsy of an organ.

The samples used in the present invention include fixed or preserved cell or tissue samples.

The present invention also provides a kit containing the antibody (or a fragment thereof) of the present invention. In a preferred embodiment of the present invention, the kit further includes a container, an instruction for use, a buffer, and the like. In a preferred embodiment, the antibody of the present invention may be fixed to the detection plate.

The present invention also provides a method for detecting a cell overexpressing 4-1BB protein, which includes the steps of contacting the above protein with the sample to be tested in vitro and detecting the binding of the protein with the sample to be tested.

The meaning of the overexpression is conventional in the art, and refers to the overexpression of RNA or protein of the 4-1BB protein in the sample to be tested (due to increased transcription, post-transcriptional processing, translation, post-translational processing, and protein degradation changes), and increased local overexpression and functional activity due to changes in protein delivery patterns (increased nuclear localization) (e.g., in the case of increased enzymatic hydrolysis of the substrate).

The binding detection method is a conventional detection method in the art, preferably FACS detection.

The present invention provides a composition for detecting a cell overexpressing 4-1BB protein, which comprises the above protein as an active ingredient. Preferably, it also comprises a compound composed of the above-mentioned functional fragments of the protein as an active ingredient.

Based on the common sense in the art, the above-mentioned preferred conditions can be arbitrarily combined to obtain preferred embodiments of the present invention.

The reagents and raw materials used in the present invention are commercially available.

The Main Advantages of the Present Invention Include:

The protein of the present invention is a fully human 4-1BB antibody, which has high affinity with 4-1BB protein, and can bind to the extracellular region of 4-1BB protein receptor, and can activate the downstream signal of 4-1BB molecule at the cellular level. The mixed lymphocyte experiment and the T cell stimulation experiment prove that the 4-1BB antibody has a good biological activity, and it can significantly increase the expression levels of IFN-γ and IL-2 in human mixed lymphocytes or T lymphocytes. It can be seen that the 4-1BB antibody is not only a fully human sequence, but also has excellent characteristics including the high specificity of binding to the human 4-1BB protein and the ability to regulate the immune response of human lymphocytes.

The present invention will be further described below in conjunction with specific embodiments. It should be understood that these examples are only used to illustrate the present invention and not to limit the scope of the present invention. The experimental methods without specific conditions in the following examples generally follow the conventional conditions or the conditions recommended by the manufacturer. Unless otherwise stated, percentages and parts are calculated by weight.

The room temperature described in the examples is conventional room temperature in the art, and is generally 10-30° C.

Unless otherwise specified, the PBS described in the examples is PBS phosphate buffer, pH 7.2.

EXAMPLE 1

Preparation of the 4-1BB Antibody (1) Preparation of the Immunogen A

The amino acid sequence Leu24-Gln186 (as shown in SEQ ID NO: 21 of the sequence listing) of extracellular domain of human 4-1BB protein was cloned into a pCpC vector (purchased from Invitrogen, V044-50) with a human IgG Fc fragment (hFc) and the plasmid was prepared according to the established standard molecular biology method. HEK293 cells (purchased from Invitrogen) were transiently transfected (PEI, Polysciences) and expanding cultured using FreeStyle™ 293 (Invitrogen) at 37° C. After 4 days, the cell culture was collected, and the cell components were removed by centrifugation to obtain a culture supernatant containing the extracellular region of 4-1BB protein. The culture supernatant was loaded onto a protein A affinity chromatography column (Mabselect Sure, purchased from GE Healthcare), meanwhile the changes in ultraviolet absorption value (A280 nm) were monitored with an ultraviolet (UV) detector. After the sample was loaded, the protein A affinity chromatography column was washed with PBS phosphate buffer (pH 7.2) until the UV absorption value returned to the baseline, and then eluted with 0.1 M glycine hydrochloric acid (pH 2.5) to collect the hFc-tagged 4-1BB protein (4-1BB-hFc) eluted from the Protein A affinity chromatography column. It was dialyzed with PBS phosphate buffer (pH 7.2) in a refrigerator at 4° C. overnight. After dialysis, the protein was sterile filtered at 0.22 microns and stored at −80° C. to obtain purified immunogen A. Immunogen A requires a series of quality control tests before use, such as the detection of protein concentration, purity, molecular weight, and biological activity etc. The results are shown in FIG. 1 and Table 3. Table 3 shows that the binding of 4-1BB to its ligand protein 4-1BBL at the protein level will change with the concentration of 4-1BBL, wherein, the control protein is a non-4-1BB fusion protein, and the data in the table is the $OD_{450\ nm}$ value.

Wherein, the biological activity of immunogen A was detected by ELISA, specifically:

the hFc-tagged 4-1BB extracellular domain protein (4-1BB-hFc) was diluted with PBS to 0.5 μg/mL, added to the ELISA microplate at 100 μl/well, and incubated overnight at 4° C. After blocked with ELISA blocking solution (containing 1% BSA, PBS phosphate buffer of pH 7.4, wherein the percentage is the mass percentage) at 37° C. for two hours, his-muCD8a-4-1BBL$^{ECD}$ fusion protein with gradient dilution was added and incubated at 37° C. for 1 hour. His-muCD8a-4-1BBL$^{ECD}$ is composed of the fusion of a 4-1BB ligand 4-1BBL extracellular domain (Arg71-Glu254 of NCBI sequence NP_003802.1) and a mouse CD8a extracellular domain (Lys28-Asp194 of NCBI sequence NP_001074579.1), and his-tag is on the N side. The expression method of his-muCD8a-4-1BBL$^{ECD}$ protein, such as immunogen A, was prepared and purified by nickel column affinity chromatography.

Next, biotin-labeled rat anti-mouse CD8a antibody was added and incubated at 37° C. for 1 hour. Streptavidin-labeled horseradish peroxidase (purchased from Sigma, article number 52438) was added, and after incubated at room temperature for 30 minutes, 100 μl/well TMB color developing solution was added. After incubated for 15 minutes at room temperature, 50 μl of 1N hydrochloric acid was added to stop the color reaction, and the $OD_{450\ nm}$ reading was read with an ELISA plate reader.

TABLE 3 binding activity of 4-1BB-hFc protein to the receptor 4-1BBL

| Sample | $OD_{450\ nm}$ his-muCD8a-4-1BBL$^{ECD}$ protein concentration (μg/mL) | | | | | | | |
|---|---|---|---|---|---|---|---|---|
| | 3 | 1 | 0.3333 | 0.1111 | 0.037 | 0.0123 | 0.0041 | 0.0014 |
| 4-1BB$^{ECD}$-hFc | 1.87 | 1.83 | 1.85 | 1.65 | 1.26 | 0.68 | 0.44 | 0.56 |
| control protein (non-4-1BB-hFc) | 0.41 | 0.38 | 0.39 | 0.39 | 0.37 | 0.40 | 0.40 | 0.42 |

(2) Preparation of the Immunogen B

Figure 2:
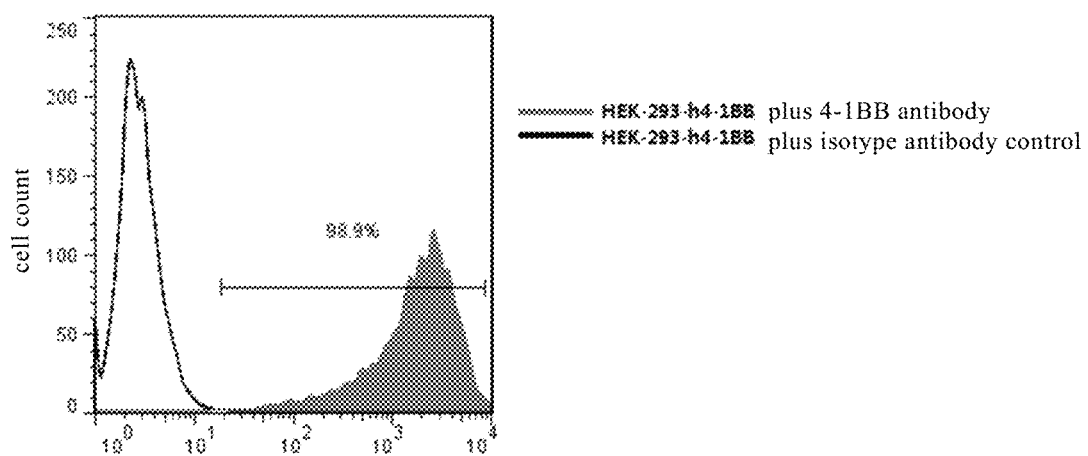
FIG. 2 shows FACS screening and detecting of HEK293 cells transfected with 4-1BB protein.

The full-length amino acid sequence of human 4-1BB (as shown in SEQ ID NO: 23 of the sequence listing) was cloned into pIRES vector (purchased from Clontech) and a plasmid was prepared. After plasmid transfection of HEK293 cell line and CHOK1 cell line (both purchased from Invitrogen) (transfection using X-treme GENE HP DNA Transfection Reagent, purchased from Roche, item No. Cat #06 366 236 001, following the instructions), cells were selectively cultured in DMEM medium containing 0.5 μg/mL of 10% (w/w) FBS for 2 weeks, subcloned in 96-well culture plate by a limiting dilution method, and placed and cultured at 37° C., 5% (v/v) $CO_2$. After about 2 weeks, a part of the monoclonal wells were selected and expanded into 6-well plates. The amplified clones were screened by flow cytometry using a known 4-1BB antibody (purchased from BD). Immunogen B is obtained by selecting a cell line with better growth, higher fluorescence intensity, and monoclonal cell to continue to expand the culture and freeze storage in liquid nitrogen. The specific selection results are shown in Table 4 and FIG. 2. The positive cells (%) in Table 4 refer to the percentage of positive cells in the total number of cells. Table 4 shows that a series of 4-1BB-positive HEK293 cell lines have been prepared.

TABLE 4

FACS screening detection results of HEK293 cells transfected with 4-1BB protein

| | | h4-1BB antibody | |
|---|---|---|---|
| serial number | transfected cell clone number | positive cells (%) | average fluorescence intensity |
| 1 | 3C10 | 98.3 | 1248.6 |
| 3 | 4G8 | 98.9 | 1185.6 |
| 4 | 4H7 | 97.5 | 1026.2 |
| 5 | 4G5 | 97.7 | 924.9 |
| 6 | 4B7 | 99.5 | 833.4 |
| 7 | 4G10 | 97.8 | 752.7 |
| 8 | 4F11 | 97.9 | 726.1 |
| 9 | 3F10 | 99.2 | 712.8 |
| 10 | 3C9 | 99.2 | 707.1 |
| 11 | 3F1 | 99.3 | 697.5 |
| 12 | 3F3 | 98.6 | 602.8 |
| 13 | 4E10 | 93.1 | 527.8 |
| 14 | 4C12 | 99.0 | 478.6 |
| 15 | 4H9 | 98.3 | 457.5 |
| 16 | 4G11 | 99.2 | 400.7 |
| 17 | 4H6 | 99.4 | 365.8 |
| 18 | 4B6 | 98.1 | 266.2 |
| 19 | 3F11 | 98.9 | 217.6 |
| 20 | 4C4 | 92.9 | 117.1 |

(3) Preparation of Hybridoma Cells and Antibody Screening

Harbour transgenic mice were introduced with human immunoglobulin variable region genes and rat immuno-globulin constant region genes, while the Ig expression of the mice themselves was silenced. After being immunized with antigens, the transgenic mice can produce immune responses and antibody titers comparable to normal mice (such as Balb/c).

Figure 3:
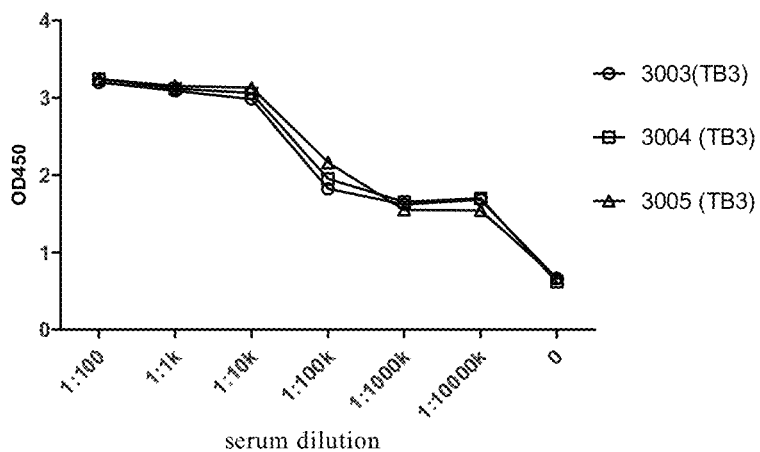
FIG. 3 shows the ELISA detection of serum antibody titers of Harbour transgenic mice after 4-1BB immunization.
Figure 4:
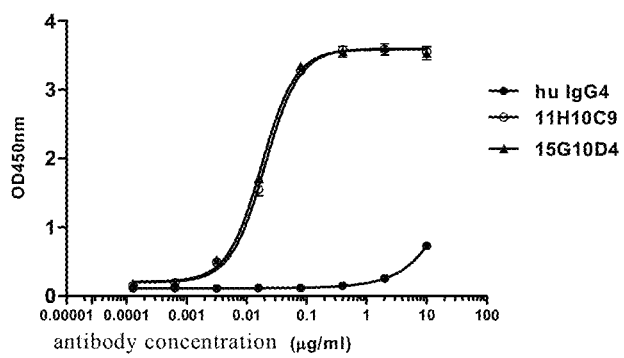
FIG. 4A-4H show the binding reaction of each 4-1BB fully human antibody to human 4-1BB-hFc protein detected by ELISA, respectively.
Figure 4:
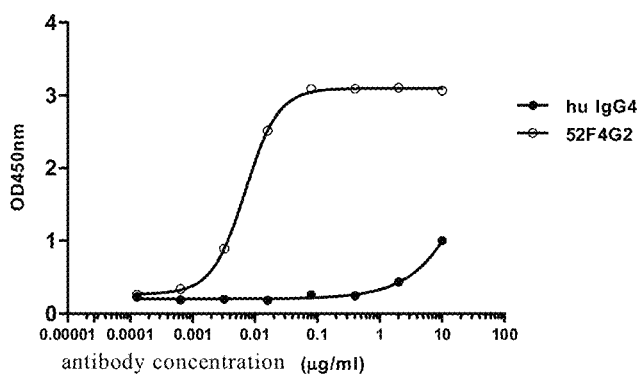
Figure 4:
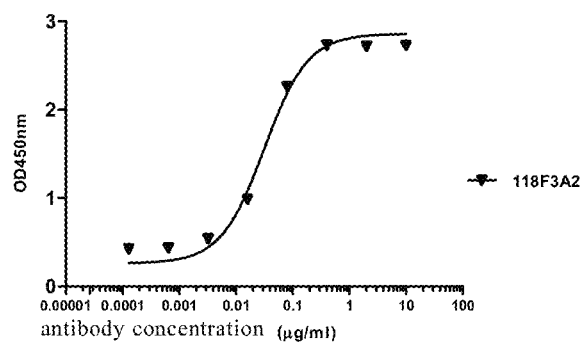
Figure 4:
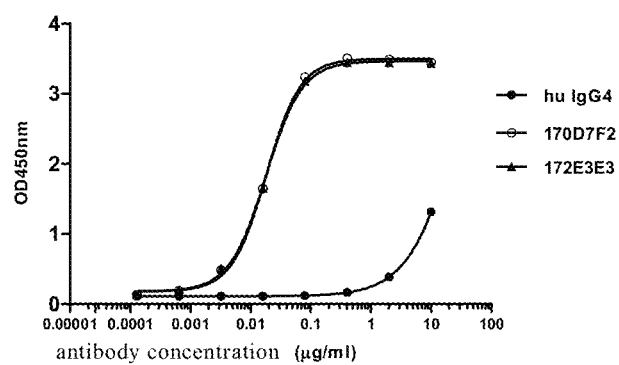
Figure 4:
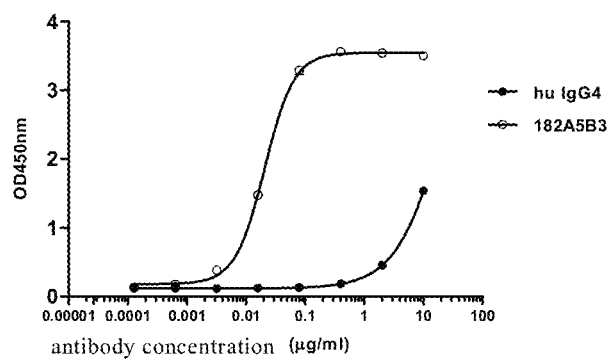
Figure 4:
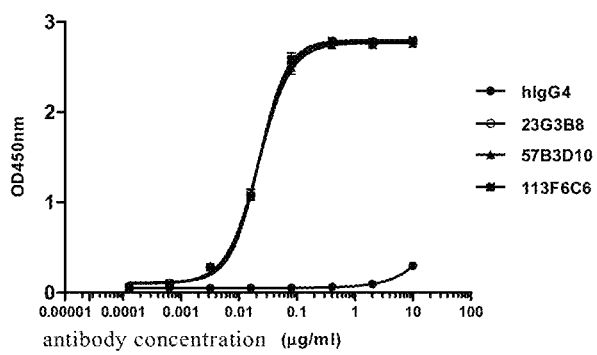
Figure 4:
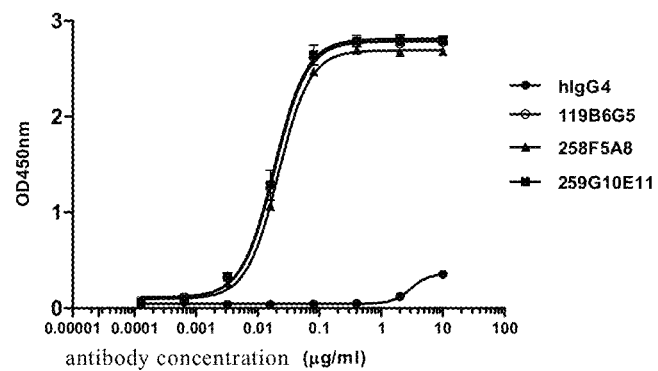
Figure 4:
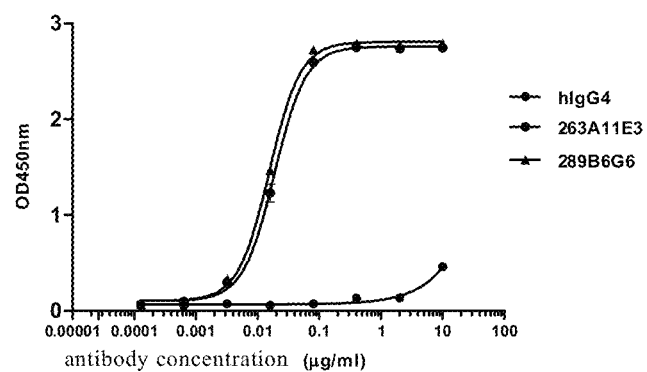
Figure 5:
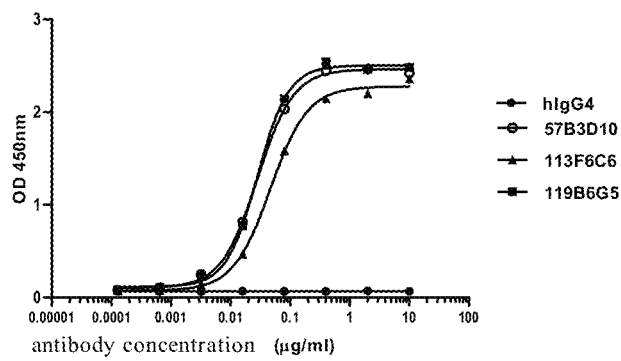
FIGS. 5A and 5B show the binding reaction of each 4-1BB fully human antibody to monkey 4-1BB-hFc protein detected by ELISA, respectively.
Figure 5:
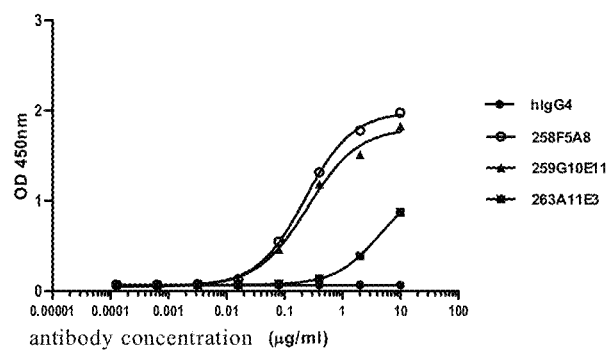
Figure 6:
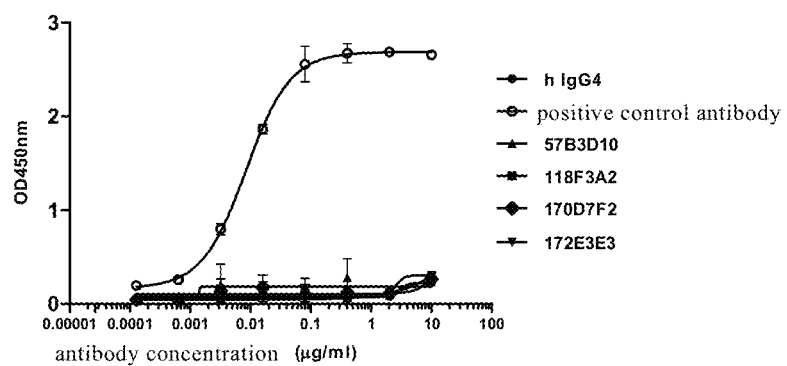
FIGS. 6A and 6B show the binding reaction of each 4-1BB fully human antibody to monkey 4-1BB-hFc protein detected by ELISA, respectively.
Figure 6:
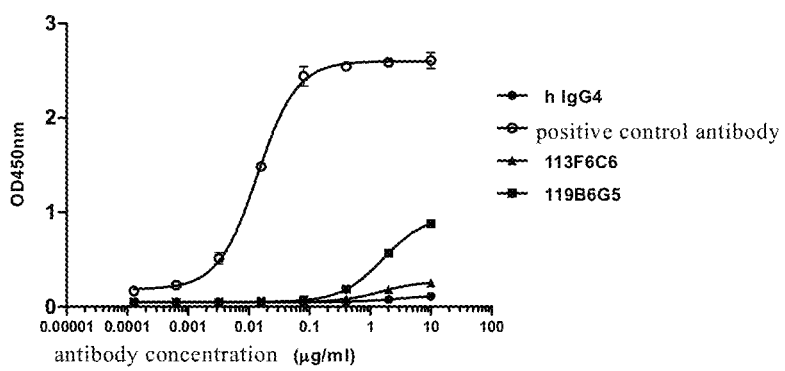
Figure 7:
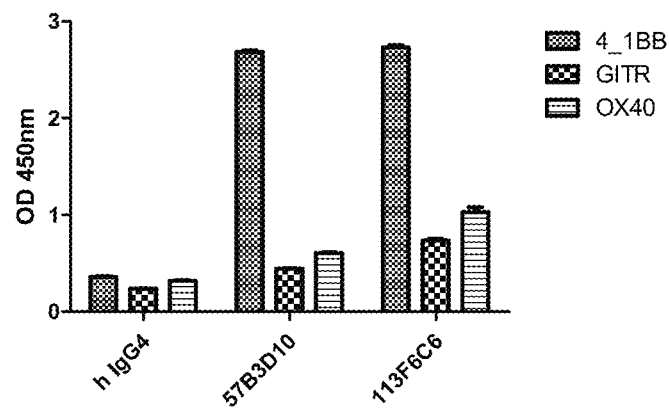
FIG. 7 shows the binding reaction of 4-1BB fully human antibody to other immune checkpoint proteins detected by ELISA.
Figure 8A:
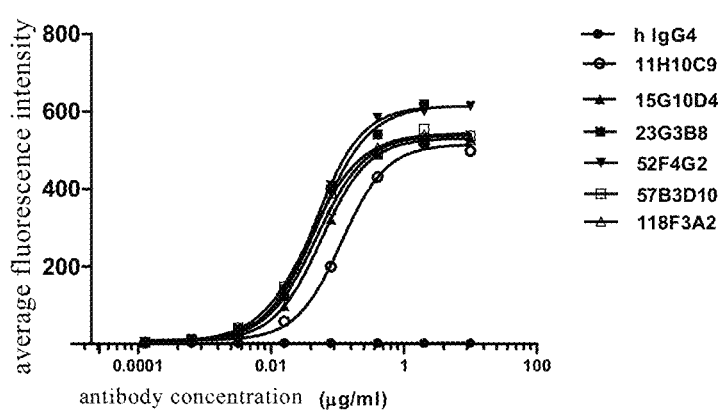
FIG. 8A-8E show the binding reaction of each 4-1BB fully human antibody to CHOk1-h4-1BB detected by FACS, respectively.
Figure 8B:
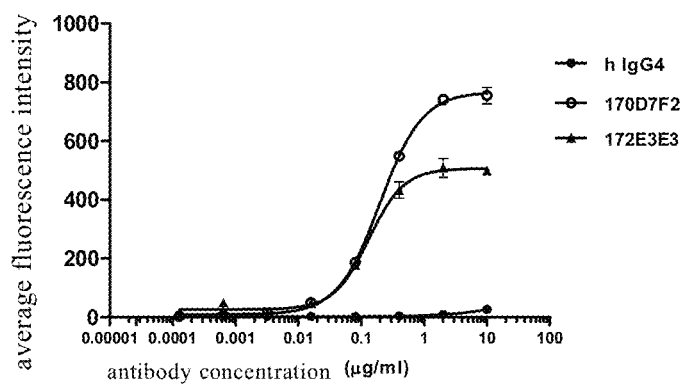
Figure 8C:
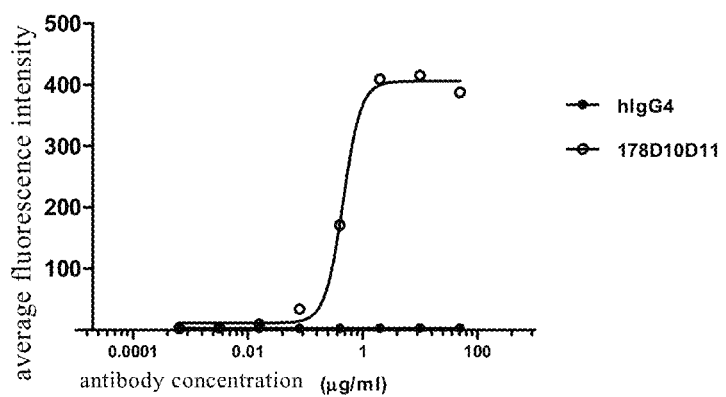
Figure 8D:
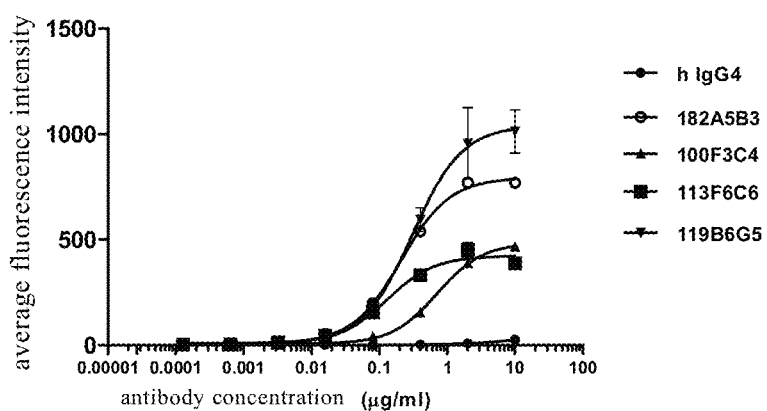
Figure 8E:
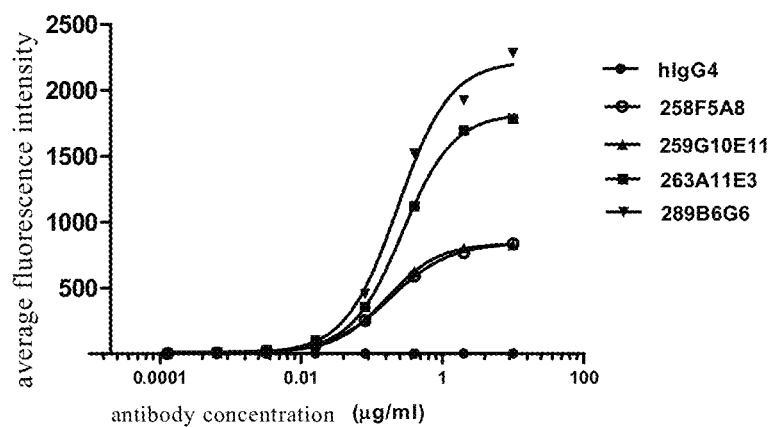
Figure 9A:
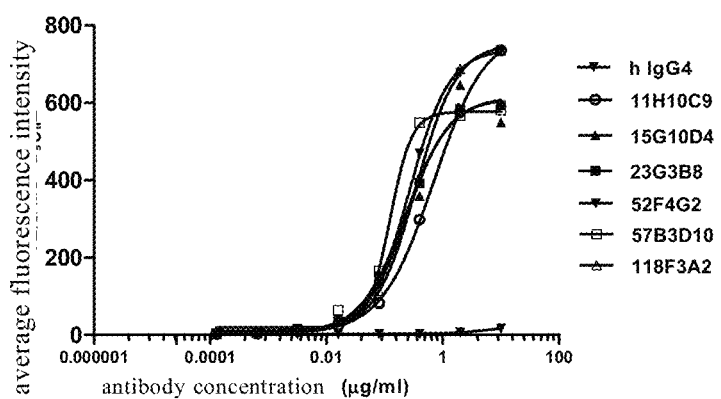
FIG. 9A-9D show the binding reaction of each 4-1BB fully human antibody to CHOk1-c4-1BB detected by FACS, respectively.
Figure 9B:
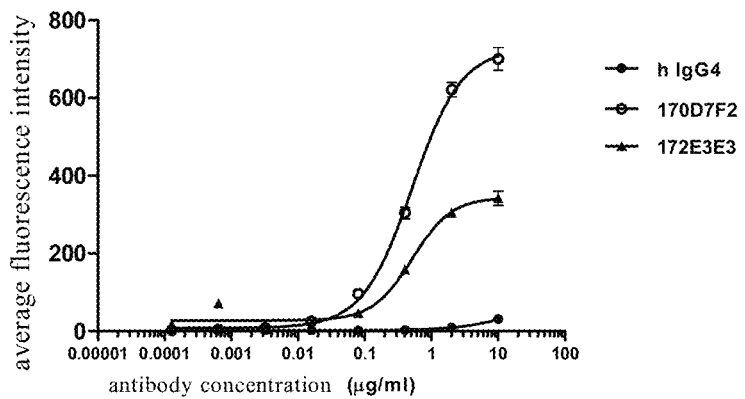
Figure 9C:
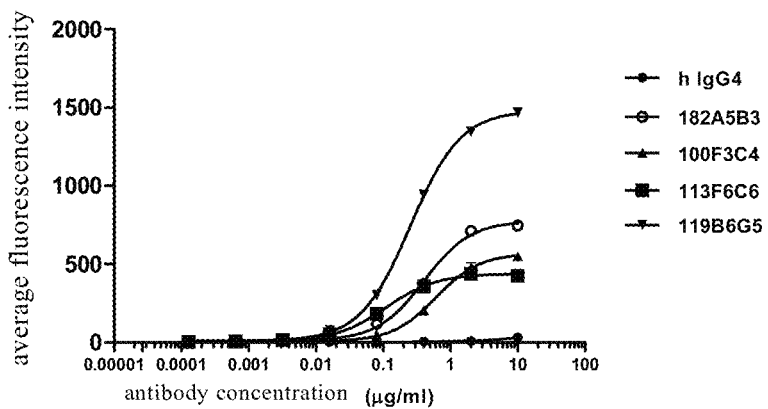
Figure 9D:
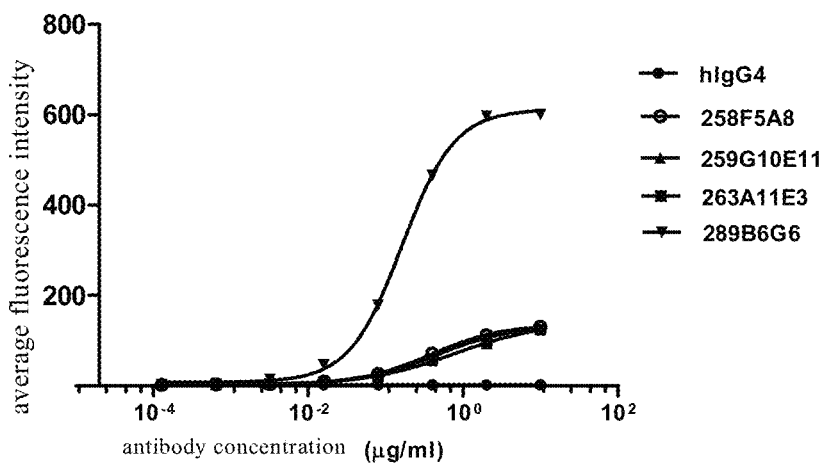

A. 6-8 week old Harbour human antibody transgenic mice (purchased from Beijing Viton Lihua Company) were used for immunization of Immunogen A. The mice were raised under SPF conditions. During the initial immunization, the immunogen (1) protein was emulsified with Freund's complete adjuvant and injected intraperitoneally 0.25 ml, that is, each mouse was injected with 100 micrograms of immunogen A protein. During booster immunization, immunogen A protein was emulsified with Freund's incomplete adjuvant and injected intraperitoneally 0.25 ml, that is, each mouse was injected with 50 micrograms of immunogen A protein. The interval between the first immunization and the first booster immunization was 2 weeks, and the interval between subsequent booster immunizations was 3 weeks. Blood was collected one week after each booster immunization, and the antibody titer and specificity of immunogen (1) in the serum were detected by ELISA and FACS. The results are shown in FIG. 3 and Table 5. Table 5 shows that the serum of mice immunized with 4-1BB-hFc all have different levels of binding to immunogens, showing antigen-antibody reactions, with the highest dilution of about one million. The blank control is 1% (w/w) BSA, wherein the batch refers to the mouse serum on the seventh day after the third booster immunization. The data in the table is the $OD_{450\ nm}$ value.

TABLE 5

ELISA detection on serum antibody titer of Harbour transgenic mice after 4-1BB protein immunization

| animal number | $OD_{450\ nm}$ serum dilution | | | | | | |
|---|---|---|---|---|---|---|---|
| | 1:100 | 1:10³ | 1:10⁴ | 1:10⁵ | 1:10⁶ | 1:10⁷ | Blank |
| 3003 (TB3) | 3.2 | 3.09 | 2.98 | 1.82 | 1.62 | 1.68 | 0.66 |
| 3004 (TB3) | 3.24 | 3.12 | 3.06 | 1.95 | 1.65 | 1.7 | 0.62 |
| 3005 (TB3) | 3.24 | 3.15 | 3.13 | 2.16 | 1.55 | 1.54 | 0.67 |

B. Immunogen B immunization adopted 6-8 week-old Harbour human antibody transgenic mice (purchased from Beijing Viton Lihua Company), and the mice were raised under SPF conditions. The HEK293-h4-1BB stable cell line containing human-derived 4-1BB obtained in step (2) of Example 1 was expanded and cultured in a T-75 cell culture flask to 90% confluence, and the culture medium was exhausted. It was washed twice with DMEM basal medium (purchased from Invitrogen), and then treated with enzyme-free cell dissociation solution (purchased from Invitrogen) at 37° C. until the cells were detached from the culture dish wall, and the cells were collected, washed twice with DMEM basal medium, and after counted, the cells were diluted with phosphate buffer (pH 7.2) to $2\times10^7$ cells per ml. Each mouse was injected intraperitoneally with 0.5 ml of cell suspension during each immunization. The interval between the first and second immunization was 2 weeks, and interval between each subsequent immunizations was 3 weeks. Except for the first immunization, blood was collected 1 week after each immunization, and antibody titer and specificity in serum were detected by FACS. After the second booster immunization, the titer of serum antibody detected by FACS usually reaches more than 1:1000.

Immunization was usually carried out with immunogens A and B. After three immunizations, the FACS titer of most mice can reach more than 1:1000.

Before the completion of steps A and B, each selected mouse was injected for the last time intraperitoneally with 100 μg of purified 4-1BB-hFc (a mouse that has undergone immune reaction against immunogen A and immunogen C) or an HEK293-h4-1BB stable cell line containing human-derived 4-1BB (a mouse that immunized against immunogen B). 5 days later, the mice were sacrificed and spleen cells were collected. $NH_4OH$ was added to a final concentration of 1% (w/w) to lyse the red blood cells in the spleen cells to obtain a spleen cell suspension. The cells were centrifuged and washed with DMEM basal medium at 1000 rpm for 3 times, and then mixed with a mouse myeloma cells SP2/0 (purchased from ATCC) at a ratio of 5:1 of viable cells. Cell fusion was performed by high-efficiency electrofusion or PEG methods. The fused cells were diluted into DMEM medium containing 20% fetal bovine serum and 1×HAT, and the percentage was the mass percentage, and then $1\times10^5/20$ microliters were added per well to a 96-well cell culture plate and placed in a 5% $CO_2$, 37° C. incubator. The percentage was the volume percentage. After 14 days, the cell fusion plate supernatant was screened by ELISA and Acumen (microplate cell detection method), and positive clones with $OD_{450\ nm}>1.0$ in ELISA and MFI value>100 in Acumen were amplified into 24-well plates, and the culture was expanded at 37° C. under 5% (v/v) $CO_2$ in DMEM medium (Invitrogen) containing 10% (w/w) fetal bovine serum. After culturing for 3 days, the culture medium of the expanded culture in the 24-well plate was centrifuged, the supernatant was collected, and the supernatant was analyzed for antibody subtypes. ELISA, FACS were used to determine the binding activity of 4-1BB protein and 4-1BB positive cells (for the detection method of binding activity, please refer to Example 5A and Example 5B, respectively), and then the NF-κB luciferase reporter gene experiment was used to determine the activity of the antibody sample on 4-1BB receptor activation (see Example 5 for detection method).

According to the screening results of the 24-well plate, selecting hybridoma cells with OD450 nm>1.0 in the ELISA experiment, MFI value>50 in the FACS experiment, and whose cell culture supernatant in the NF-κB luciferase reporter gene experiment activates the 4-1BB receptor by more than 1.0 times compared with the control IgG group as the eligible positive clones. Qualified hybridoma cells were selected for subcloning in 96-well plate by limiting dilution method, and cultured in DMEM medium (purchased from Invitrogen) containing 10% (w/w) FBS, it was cultured at 37° C., 5% (v/v) $CO_2$ conditions. Ten days after subcloning, preliminary screening was performed by ELISA and Acumen, and positive monoclonals were selected and amplified to a 24-well plate to continue cultivation. Three days later, FACS was used to confirm the positive antigen binding and the biological activity was evaluated by the 4-1BB receptor NF-κB luciferase reporter gene experiment (the evaluation criteria were $OD_{450\ nm}>1.0$ in ELISA experiment, MFI value>5 in FACS experiment, and in NF-κB luciferase reporter gene experiment, the hybridoma cell culture supernatant activated the 4-1BB receptor more than 1.0-fold compared to the control IgG group).

According to the test results of the 24-well plate samples, the positive clones were expanded and cultured in DMEM (purchased from Invitrogen) medium containing 10% (w/w) FBS at 37° C. and 5% (v/v) $CO_2$ conditions. The cells are suspended in the cryopreservation solution [DMEM containing 20% (w/w) FBS and 10% (w/w) DMSO], and the hybridoma cells of the present invention are obtained by cryopreservation according to the conventional method, and can be used for subsequent antibody sequencing.

EXAMPLE 2

Determination of Amino Acid Sequence of Light and Heavy Chain Variable Regions

Total RNA isolation: After the supernatant obtained from the subcloning culture of Example 1 has been tested for antigen binding (that is, after the verification and activity measurement of Examples 3 to 6), some antibodies (see Tables 6 and 7) were selected for sequencing. $5 \times 10^7$ hybridoma cells were collected by centrifugation, and 1 mL Trizol was added to mix and transferred to a 1.5 mL centrifuge tube, and placed at room temperature for 5 minutes. 0.2 mL of chloroform was added, shaked for 15 seconds, placed for 2 minutes and centrifuged at 12,000 g for 5 minutes at 4° C. The supernatant was taken and transferred to a new 1.5 mL centrifuge tube. 0.5 mL of isopropanol was added, and the liquid was mixed in the tube gently, placed at room temperature for 10 minutes. Then it was centrifuged at 12,000 g for 15 minutes at 4° C., and the supernatant was discarded. 1 mL of 75% ethanol (the percentage is volume percentage) was added, and the precipitate was gently washed, centrifuged at 12000 g at 4° C. for 5 minutes. The supernatant was discarded, and the precipitate was dried, added with DEPC-treated $H_2O$ to dissolve (promoting dissolution in a 55° C. water bath for 10 minutes) to give a total RNA.

Reverse transcription and PCR: 1 μg of total RNA was taken for configuring a 20 μl system. After reverse transcriptase was added, it was reacted at 42° C. for 60 minutes and at 7° C. for 10 minutes to terminate the reaction. 50 μl PCR system was configured, which includes 1 μl cDNA, 25 pmol of each primer, 1 μl DNA polymerase and a matching buffer system, 250 μmol dNTPs. The PCR program was set, subjected to initial denaturation at 95° C. for 3 minutes, denaturation at 95° C. for 30 seconds, annealed at 55° C. fo30 seconds, extension at 72° C. for 35 seconds, and extenr sion at 72° C. for 5 minutes after 35 cycles to obtain a PCR product. The kit used for reverse transcription was PrimeScript RT Master Mix, purchased from Takara, item number RR036; the kit used for PCR was Q5 super-fidelity enzyme, purchased from NEB, item number M0492.

Cloning and sequencing: 5 μl of PCR product was taken for agarose gel electrophoresis detection, and the column recovery kit was used to purify the test positive samples. The recovery kit was NucleoSpin® Gel & PCR Clean-up, purchased from MACHEREY-NAGEL, item No. 740609. Ligation reaction was performed: 50 ng of sample, 50 ng of T vector, 0.5 μl of ligase, 1 μl of buffer, 10 μl of reaction system, and the ligation product was obtained by reacting at 16° C. for half an hour. The ligation kit was T4 DNA ligase, purchased from NEB, item number M0402. 5 μl of the ligation product was taken and added to 100 μl of competent cells (Ecos 101 competent cells, purchased from Yeastern, item No. FYE607), subjected to ice bath for 5 minutes, and then heat shock at 42° C. for 1 minute in water bath. It was put back on ice for 1 minute, and 650 μl of antibiotic-free SOC medium was added, recovered at 200 RPM for 30 minutes on a 37° C. shaker, and 200 μl was coated on LB solid medium containing antibiotics and incubated in a 37° C. incubator overnight. The next day, primers M13F and M13R on the Tvector were used to configure a 30 μl PCR system, and colony PCR was performed, using a pipette tip to dip the colony into the PCR reaction system and blowing it up, and aspirating 0.5 μl spot on another LB solid petri dish containing 100 nM ampicillin to preserve the strain. After the PCR reaction was completed, 5 μl was removed for agarose gel electrophoresis detection, and the positive samples were sequenced. For the steps of sequencing, see Kabat, Sequences of Proteins of Immunological Interest, National Institutes of Health, Bethesda, Md. (1991).

The sequencing results are shown in Tables 6-7

TABLE 6

Sequence listing numbers of Amino Acid Sequences of 4-1BB Antibodies

| Clone number | Heavy chain protein | | | | Light chain protein | | | |
| --- | --- | --- | --- | --- | --- | --- | --- | --- |
| | Variable region | CDR1 | CDR2 | CDR3 | Variable region | CDR1 | CDR2 | CDR3 |
| 57B3D10 | 1 | 2 | 3 | 4 | 5 | 6 | 7 | 8 |
| 113F6C6 | 9 | 10 | 11 | 12 | 13 | 14 | 15 | 16 |
| 11H10C9 | 17 | 18 | 19 | 20 | 21 | 6 | 22 | 23 |
| 15G10D4 | 24 | 18 | 19 | 25 | 26 | 6 | 22 | 23 |
| 23G3B8 | 27 | 28 | 29 | 30 | 31 | 32 | 33 | 34 |
| 52F4G2 | 35 | 28 | 36 | 37 | 38 | 39 | 40 | 41 |
| 118F3A2 | 42 | 43 | 44 | 45 | 46 | 47 | 22 | 8 |
| 170D7F2 | 48 | 49 | 50 | 51 | 52 | 53 | 54 | 55 |
| 172E3E3 | 56 | 57 | 58 | 59 | 60 | 61 | 62 | 63 |
| 178D10D11 | 64 | 57 | 65 | 66 | 67 | 68 | 62 | 69 |
| 182A5B3 | 70 | 49 | 71 | 51 | 72 | 73 | 54 | 55 |
| 100F3C4 | 74 | 57 | 58 | 75 | 76 | 77 | 15 | 78 |
| 119B6G5 | 79 | 80 | 81 | 82 | 83 | 84 | 33 | 85 |
| 258F5A8 | 86 | 10 | 11 | 87 | 88 | 89 | 90 | 91 |
| 259G10E11 | 92 | 10 | 11 | 140 | 93 | 94 | 90 | 91 |
| 263A11E3 | 95 | 28 | 96 | 97 | 98 | 32 | 33 | 99 |
| 289B6G6 | 100 | 28 | 101 | 102 | 103 | 104 | 33 | 105 |

Wherein, the numbers in Table 6 are the numbers of "SEQ ID NO" in the sequence listing. For example, the amino acid sequence of the variable region of the heavy chain protein of 57B3D10 is SEQ ID NO: 1 in the sequence listing, and the amino acid sequence of the CDR1 domain in the variable region of the heavy chain protein of 57B3D10 is SEQ ID NO: 2 in the sequence listing.

TABLE 7

Sequence listing numbers of nucleotide
sequences of 4-1BB antibodies

| Clone number | Heavy chain variable region | Light chain variable region |
|---|---|---|
| 57B3D10 | 106 | 107 |
| 113F6C6 | 108 | 109 |
| 11H10C9 | 110 | 111 |
| 15G10D4 | 112 | 113 |
| 23G3B8 | 114 | 115 |
| 52F4G2 | 116 | 117 |
| 118F3A2 | 118 | 119 |
| 170D7F2 | 120 | 121 |
| 172E3E3 | 122 | 123 |
| 178D10D11 | 124 | 125 |
| 182A5B3 | 126 | 127 |
| 100F3C4 | 128 | 129 |
| 119B6G5 | 130 | 131 |
| 258F5A8 | 132 | 133 |
| 259G10E11 | 134 | 135 |
| 263A11E3 | 136 | 137 |
| 289B6G6 | 138 | 139 |

The numbers in Table 7 are the numbers of "SEQ ID NO" in the sequence listing. For example, the nucleotide sequence encoding the variable region of the heavy chain protein of 57B3D10 is SEQ ID NO: 106 in the sequence listing.

EXAMPLE 3

Conversion and Preparation of Fully Human Antibody IgG (1) Plasmid construction and preparation: purified 4-1BB antibody has been obtained from the culture supernatant of hybridoma cells in Example 2, and according to the sequencing results of Example 1, the heavy chain variable region and light chain variable region sequences of the 4-1BB antibody were identified. The sequence of the heavy chain variable region of the 4-1BB antibody was recombined into an expression vector containing the signal peptide and the constant region of the human heavy chain antibody IgG1 (wherein the expression vector was purchased from Invitrogen, and the recombination step was also completed by Shanghai ChemPartners). The light chain variable region sequence of the 4-1BB antibody was recombined into an expression vector containing the signal peptide and the human antibody light chain kappa constant region, and the recombinant plasmid was obtained and verified by sequencing (the sequencing method was the same as the sequencing method in Example 7). Using an alkaline lysis method kit (purchased from MACHEREY-NAGEL), the recombinant plasmid with high purity was medium extracted, with a mass of 500 μg or more, it was filtered through 0.22 μm filter (purchased from Millopore) for transfection.

(2) Cell Transfection:

293E cells (purchased from Invitrogen) were cultured in the Freestyle 293 expression medium (purchased from Invitrogen). The shaker was set to 37° C., 130 RPM, and 8% $CO_2$ (v/v) concentration.

Freestyle 293 expression medium was added with 10% (v/v) F68 (purchased from Invitrogen) to a final F68 concentration of 0.1% (v/v) at the time of transfection. Freestyle 293 expression medium containing 0.1% (v/v) F68 was obtained, namely medium A.

5 mL of medium A and 200 μg/mL PEI (purchased from Sigma) were mixed to obtain medium B. 5 mL of medium A and 100 μg/mL of the recombinant plasmid obtained in step (1) were mixed well to obtain medium C. After 5 minutes, the medium B and the medium C were combined and mixed well, and placed for 15 minutes to obtain a mixed solution D. 10 mL of mixed solution D was slowly added to 100 mL of Freestyle 293 expression medium containing 293E cells to a cell density of 293E of $1.5 \times 10^6$/mL. Shaking while adding to avoid excessive concentration of PEI and placing it in a shaker to be cultured. The next day peptone was added to a final concentration of 0.5% (w/v). On days 5-7, the antibody titer of the culture medium was measured. On days 6-7, the supernatant was collected by centrifugation (3500 RPM, 30 minutes) and filtered through a 0.22 μm filter membrane to obtain the filtered cell supernatant for purification.

(3) Antibody purification: for continuously produced endotoxin-free chromatography columns and Protein A packing (purchased from GE), 0.1M NaOH was used for the treatment of 30 minutes or 5 column volumes of 0.5M NaOH was used for wash. For column materials and chromatography columns that have not been used for a long time, 1M NaOH was used for soaking for at least 1 hour, rinsed with neutral water to neutrality, and the column materials were washed with 1% (v/v) Triton×100 of 10 times the column volume. Five column volumes of PBS (PBS phosphate buffer, pH 7.2) were used for equilibration, and the filtered cell supernatant obtained in step (2) was put on the column, and the flow-through liquid was collected if necessary. After being loaded to the column, it was washed with 5 column volumes of PBS and eluted with 5 column volumes of 0.1M pH 3.0 Glycine-HCl, the eluate was collected, and neutralized with 0.5 column volumes of eluent pH 8.5 1MTris-HCl (1.5M NaCl), and fully human 4-1BB antibody was obtained. The solutions used above all required new configuration. After obtaining the fully human 4-1BB antibody, dialysis was performed in 1×PBS for 4 hours to avoid endotoxin contamination. After dialysis, the concentration was measured using spectrophotometry or a kit, the antibody purity was measured using HPLC-SEC, and the endotoxin content of the antibody was detected using an endotoxin detection kit (purchased from Lonza). The obtained fully human 4-1BB antibody was characterized (the same as in Example 4-8), and the detection results are shown in FIG. 4-13 and Table 8-18, respectively. FIGS. 4 to 13 and Tables 8 to 17 show that the fully human 4-1BB antibody converted and prepared by fully human IgG can activate the downstream signaling pathway of the 4-1BB molecule.

EXAMPLE 4

Lead Antibody Identifying

A. Enzyme-Linked Immunosorbent Assay (ELISA) was Used to Detect the Binding of Antibody to 4-1BB Protein The purified fully human 4-1BB antibody obtained in Example 2 was cross-reacted with the human 4-1BB-hFc protein, with the monkey 4-1BB-his, and with other immune checkpoint proteins OX40 and GITR in the family of the 4-1BB protein, respectively.

The purified immunogen A (4-1BB-hFc), monkey 4-1BB-his, and mouse 4-1BB-his obtained in Example 1 [for the preparation method, see step 1 of Example 1, preparation of immunogen A], of which the extracellular domain of monkey-derived 4-1BB protein (purchased from ACROBiosystems), the extracellular domain of mouse 4-1BB protein (purchased from Sino Biological) or other immune detection point proteins respectively were diluted with PBS to a final concentration of 1.0 μg/mL, then added with 100 μl per well to 96-well ELISA plate. It was sealed with plastic film and incubated at 4° C. overnight. The next day, the plate was washed twice with the plate-washing solution [PBS containing 0.01% (v/v) Tween20] and blocking solution [PBS containing 0.01% (v/v) Tween 20 and 1% (v/v) BSA] was added and blocked at room temperature for 2 hours. The blocking solution was discarded and 100 µl of the purified 4-1BB antibody obtained in Example 2 was added per well. After incubated at 37° C. for 2 hours, the plate was washed 3 times with a plate-washing solution [PBS containing 0.01% (v/v) Tween20]. A secondary antibody (purchased from Sigma) labeled with HRP (horseradish peroxidase) was added, and after incubated at 37° C. for 2 hours, the plate was washed 3 times with a plate-washing solution [PBS containing 0.01% (v/v) Tween20]. 100 µl of TMB substrate was added per well. After incubated for 30 minutes at room temperature, 100 µl of stop buffer (1.0N HCl) was added per well. The A450 nm values were read using an ELISA plate reader (SpectraMax 384plus, Molecular Device). The results are shown in FIGS. 4-7 and Tables 8-11. Tables 8-11 illustrate that the purified antibody specifically binds to the 4-1BB recombinant protein at the ELISA level. The blank is human IgG, CTLA4-Fc is used as a negative control (NC), and the data in the table is the $OD_{450\ nm}$ value.

TABLE 8

ELISA detection of the binding reaction of fully human 4-1BB antibody to human 4-1BB-hFc protein

| Clone number | $OD_{450\ nm}$ antibody concentration (µg/ml) | | | | | | | |
|---|---|---|---|---|---|---|---|---|
| | 10 | 2 | 0.4 | 0.08 | 0.016 | 0.0032 | 0.0006 | 0.0001 |
| 57B3D10 | 3.06 | 3.05 | 3.08 | 3.07 | 2.54 | 0.94 | 0.35 | 0.28 |
| 113F6C6 | 3.42 | 3.46 | 3.45 | 3.36 | 2.51 | 1.1 | 0.34 | 0.16 |
| 11H10C9 | 3.55 | 3.59 | 3.58 | 3.27 | 1.55 | 0.49 | 0.19 | 0.15 |
| 15G10D4 | 3.53 | 3.61 | 3.55 | 3.35 | 1.72 | 0.52 | 0.19 | 0.17 |
| 52F4G2 | 3.06 | 3.10 | 3.09 | 3.08 | 2.51 | 0.89 | 0.34 | 0.26 |
| 118F3A2 | 2.73 | 2.72 | 2.73 | 2.26 | 0.99 | 0.54 | 0.44 | 0.43 |
| 170D7F2 | 3.44 | 3.49 | 3.50 | 3.24 | 1.64 | 0.48 | 0.19 | 0.13 |
| 172E3E3 | 3.43 | 3.44 | 3.44 | 3.18 | 1.65 | 0.51 | 0.20 | 0.14 |
| 182A5B3 | 3.50 | 3.54 | 3.56 | 3.29 | 1.48 | 0.38 | 0.18 | 0.13 |
| 23G3B8 | 2.78 | 2.78 | 2.77 | 2.53 | 1.10 | 0.28 | 0.10 | 0.07 |
| 57B3D10 | 2.76 | 2.75 | 2.75 | 2.49 | 1.10 | 0.29 | 0.10 | 0.06 |
| 113F6C6 | 2.79 | 2.78 | 2.79 | 2.58 | 1.07 | 0.28 | 0.10 | 0.06 |
| 119B6G5 | 2.78 | 2.76 | 2.77 | 2.62 | 1.25 | 0.33 | 0.11 | 0.07 |
| 258F5A8 | 2.68 | 2.67 | 2.69 | 2.47 | 1.06 | 0.26 | 0.09 | 0.06 |
| 259G10E11 | 2.80 | 2.80 | 2.79 | 2.64 | 1.29 | 0.33 | 0.11 | 0.07 |
| 263A11E3 | 2.75 | 2.74 | 2.75 | 2.59 | 1.23 | 0.30 | 0.10 | 0.07 |
| 289B6G6 | 2.80 | 2.77 | 2.79 | 2.73 | 1.47 | 0.34 | 0.11 | 0.07 |

TABLE 9

ELISA detection of the binding reaction of 4-1BB antibody with monkey 4-1BB-his protein

| Clone number | $OD_{450\ nm}$ antibody concentration (µg/ml) | | | | | | | |
|---|---|---|---|---|---|---|---|---|
| | 10 | 2 | 0.4 | 0.08 | 0.016 | 0.0032 | 0.0006 | 0.0001 |
| 57B3D10 | 2.42 | 2.47 | 2.44 | 2.03 | 0.81 | 0.25 | 0.10 | 0.08 |
| 113F6C6 | 2.36 | 2.20 | 2.14 | 1.58 | 0.47 | 0.14 | 0.08 | 0.07 |
| 119B6G5 | 2.48 | 2.46 | 2.54 | 2.15 | 0.77 | 0.24 | 0.11 | 0.08 |
| 258F5A8 | 1.98 | 1.78 | 1.32 | 0.55 | 0.13 | 0.08 | 0.07 | 0.07 |
| 259G10E11 | 1.83 | 1.51 | 1.18 | 0.46 | 0.12 | 0.07 | 0.07 | 0.07 |
| 263A11E3 | 0.87 | 0.39 | 0.14 | 0.08 | 0.07 | 0.07 | 0.07 | 0.07 |
| IgG control | 0.07 | 0.07 | 0.07 | 0.07 | 0.07 | 0.07 | 0.07 | 0.07 |

TABLE 10

ELISA detection of the binding reaction between 4-1BB antibody to mouse 4-1BB-hFc protein

| Clone number | $OD_{450\ nm}$ antibody concentration (µg/ml) | | | | | | | |
|---|---|---|---|---|---|---|---|---|
| | 10 | 2 | 0.4 | 0.08 | 0.016 | 0.0032 | 0.0006 | 0.0001 |
| 57B3D10 | 0.24 | 0.10 | 0.28 | 0.14 | 0.16 | 0.20 | 0.05 | 0.05 |
| 118F3A2 | 0.31 | 0.12 | 0.06 | 0.12 | 0.09 | 0.11 | 0.05 | 0.05 |
| 170D7F2 | 0.27 | 0.11 | 0.12 | 0.10 | 0.18 | 0.14 | 0.05 | 0.05 |
| 172E3E3 | 0.30 | 0.12 | 0.06 | 0.05 | 0.05 | 0.05 | 0.05 | 0.05 |
| 113F6C6 | 0.25 | 0.18 | 0.08 | 0.05 | 0.05 | 0.05 | 0.05 | 0.05 |
| 119B6G5 | 0.88 | 0.57 | 0.18 | 0.07 | 0.05 | 0.05 | 0.05 | 0.05 |

TABLE 10-continued

ELISA detection of the binding reaction between 4-1BB antibody to mouse 4-1BB-hFc protein

| Clone number | $OD_{450\,nm}$ antibody concentration (μg/ml) | | | | | | | |
|---|---|---|---|---|---|---|---|---|
| | 10 | 2 | 0.4 | 0.08 | 0.016 | 0.0032 | 0.0006 | 0.0001 |
| positive control antibody | 2.66 | 2.69 | 2.67 | 2.56 | 1.86 | 0.80 | 0.26 | 0.20 |
| h IgG4 | 0.23 | 0.09 | 0.06 | 0.11 | 0.12 | 0.06 | 0.05 | 0.05 |

TABLE 11

ELISA detection of binding reaction of 4-1BB antibody to other immune checkpoint proteins

| Clone number | $OD_{450\,nm}$ Immune checkpoint protein | | |
|---|---|---|---|
| | 4-1BB | GITR | OX40 |
| 57B3D10 | 2.68 | 0.44 | 0.61 |
| 113F6C6 | 2.73 | 0.74 | 1.03 |
| IgG control | 0.36 | 0.24 | 0.32 |

B. Flow Cytometry (FACS) Detection of Antibody Binding to Cells Expressing 4-1BB The pIRES plasmid containing the nucleotide sequence encoding the full-length amino acid sequence of human 4-1BB as described in step (2) of Example 1 was transfected into the CHOK1 cell line to obtain the CHOK1 stable transfected cell line containing human 4-1BB (here called CHOk1-h4-1BB stable cell line). The pIRES plasmid carrying the full-length gene of monkey-derived PDL1 (the preparation method is the same as the preparation method of the pCpC vector carrying the human-derived IgG Fc fragment (hFc) in "Preparation of immunogen A" of the step (1) in Example 1, in which the database accession number of the amino acid sequence of the extracellular region of monkey 4-1BB protein (Phe19-Thr239) is G7PSE7) was transfected into CHOK1 cell line to obtain CHOK1 stable transfected cell line containing monkey 4-1BB (herein referred to as CHOK1-c4-1BB stable cell line). The CHOK1-h4-1BB stable cell line and the CHOK1-c4-1BB stable cell line were expanded and cultivated to 90% confluence in T-75 cell culture flasks. The medium was exhausted, and washed twice with HBSS buffer (Hanks Balanced Salt Solution, purchased from Invitrogen), and then the cells were treated and collected with enzyme-free cell dissociation solution (Versene solution, purchased from Life Technology). The cells were washed twice with HBSS buffer, and after cell counting, the cells were diluted with HBSS buffer to $2\times10^6$ cells per ml, and 1% goat serum blocking solution was added, the percentage being the mass percentage. It was incubated on ice for 30 minutes, and then washed twice with HBSS buffer by centrifugation. The collected cells were suspended in FACS buffer (HBSS containing 1% BSA, the percentage was the mass percentage) to $2\times10^6$ cells/mL, and 100 μl per well was added to a 96-well FACS reaction plate. The purified 4-1BB antibody test sample obtained in Example 2 was added, 100 microliters per well and incubated on ice for 2 hours. It was washed twice by centrifugation with FACS buffer, 100 μl of fluorescent (Alexa 488)-labeled secondary antibody (purchased from Invitrogen) per well was added, and incubated on ice for 1 hour. It was washed three times with FACS buffer by centrifugation, and 100 μl of fixative [4% (v/v) paraformaldehyde] per well was added to suspend cells, and washed twice with FACS buffer after 10 minutes by centrifugation. The cells were suspended with 100 microliters of FACS buffer, and the results were detected and analyzed with FACS (FACS Calibur, purchased from BD). The results are shown in FIGS. 8-9 and Tables 12-13. The results show that the antibody to be tested can bind to the 4-1BB protein on the cell surface. The IgG control is human IgG, and the data in the table is the average fluorescence intensity value of the cell population measured by MFI.

TABLE 12

FACS detection of the binding reaction between 4-1BB antibody and CHOK1-h4-1BB

| Clone number | Average fluorescence intensity antibody concentration (μg/ml) | | | | | | | | |
|---|---|---|---|---|---|---|---|---|---|
| | 50 | 10 | 2 | 0.4 | 0.08 | 0.016 | 0.0032 | 0.00064 | 0.00013 |
| 11H10C9 | | 498.2 | 519.8 | 431.0 | 200.3 | 58.7 | 18.3 | 6.4 | 3.5 |
| 15G10D4 | | 531.6 | 521.4 | 491.7 | 321.8 | 98.2 | 28.8 | 9.3 | 4.2 |
| 23G3B8 | | | 618.7 | 541.0 | 399.0 | 126.2 | 38.5 | 11.2 | 4.6 |
| 52F4G2 | | 614.9 | 600.5 | 584.5 | 409.5 | 140.7 | 38.3 | 11.7 | 4.8 |
| 57B3D10 | | 537.5 | 555.0 | 489.8 | 388.9 | 148.4 | 42.7 | 12.5 | 4.9 |
| 118F3A2 | | 527.0 | 540.1 | 508.0 | 346.2 | 125.1 | 34.4 | 10.8 | 4.4 |
| 170D7F2 | | 735.3 | 735.9 | 540.1 | 182.6 | 48.8 | 14.0 | 4.9 | 2.6 |
| 172E3E3 | | 489.4 | 485.8 | 413.3 | 172.5 | 46.9 | 13.0 | 49.5 | 13.8 |
| 178D10D11 | 387.7 | 415.6 | 408.8 | 171.2 | 33.8 | 9.2 | 3.8 | 2.7 | |
| 182A5B3 | | 769.1 | 759.6 | 530.4 | 199.6 | 52.7 | 14.8 | 5.0 | 2.6 |
| 100F3C4 | | 458.4 | 389.9 | 154.0 | 43.1 | 12.7 | 4.6 | 2.5 | 2.0 |
| 113F6C6 | | 405.1 | 476.7 | 322.8 | 154.5 | 46.2 | 13.7 | 4.8 | 2.7 |
| 119B6G5 | | 1084.9 | 1075.7 | 636.0 | 198.7 | 49.1 | 17.8 | 5.1 | 2.6 |
| 258F5A8 | | 835.4 | 766.1 | 590.6 | 252.3 | 68.0 | 21.1 | 7.0 | 4.1 |

TABLE 12-continued

FACS detection of the binding reaction between 4-1BB antibody and CHOK1-h4-1BB

| Clone number | Average fluorescence intensity antibody concentration (µg/ml) | | | | | | | | |
|---|---|---|---|---|---|---|---|---|---|
| | 50 | 10 | 2 | 0.4 | 0.08 | 0.016 | 0.0032 | 0.00064 | 0.00013 |
| 259G10E11 | | 826.8 | 802.8 | 625.4 | 251.8 | 67.2 | 19.4 | 7.1 | 3.9 |
| 263A11E3 | | 1784.2 | 1694.9 | 1118.9 | 355.5 | 85.6 | 22.9 | 8.0 | 4.0 |
| 289B6G6 | | 2283.0 | 1921.0 | 1520.3 | 453.0 | 100.8 | 26.7 | 8.9 | 4.0 |

TABLE 13

FACS detection of the binding reaction between 4-1BB antibody and CHOK1-c4-1BB

| Clone number | Average fluorescence intensity antibody concentration (µg/ml) | | | | | | | |
|---|---|---|---|---|---|---|---|---|
| | 10 | 2 | 0.4 | 0.08 | 0.016 | 0.0032 | 0.00064 | 0.00013 |
| 11H10C9 | 735.6 | 576.4 | 298.3 | 82.6 | 24.7 | 10.4 | 3.7 | 3.0 |
| 15G10D4 | 549.9 | 646.0 | 359.0 | 156.5 | 37.3 | 12.0 | 4.8 | 3.3 |
| 23G3B8 | 594.6 | 585.5 | 392.5 | 154.2 | 34.2 | 10.8 | 4.7 | 3.4 |
| 52F4G2 | 735.6 | 679.3 | 468.7 | 129.9 | 41.2 | 13.7 | 4.5 | 3.2 |
| 57B3D10 | 581.3 | 567.2 | 548.9 | 165.9 | 63.5 | 15.0 | 5.6 | 3.3 |
| 118F3A2 | 734.8 | 687.5 | 407.7 | 114.3 | 41.2 | 11.8 | 4.9 | 2.9 |
| 170D7F2 | 700.1 | 621.4 | 304.3 | 96.3 | 25.9 | 8.5 | 4.0 | 2.6 |
| 172E3E3 | 342.3 | 304.8 | 158.8 | 47.0 | 16.7 | 6.6 | 71.7 | 17.6 |
| 182A5B3 | 745.7 | 711.7 | 373.0 | 117.8 | 33.2 | 10.4 | 4.4 | 2.7 |
| 100F3C4 | 551.5 | 478.7 | 204.5 | 51.1 | 15.2 | 5.4 | 2.9 | 2.2 |
| 113F6C6 | 426.4 | 437.5 | 357.4 | 182.0 | 51.5 | 15.1 | 5.5 | 2.9 |
| 119B6G5 | 1469.8 | 1346.7 | 944.5 | 303.0 | 77.9 | 20.7 | 6.6 | 3.2 |
| 258F5A8 | 130.6 | 112.5 | 71.4 | 26.6 | 9.9 | 4.5 | 3.0 | 2.5 |
| 259G10E11 | 125.7 | 106.8 | 64.3 | 25.4 | 9.3 | 4.3 | 2.9 | 2.5 |
| 263A11E3 | 124.0 | 93.5 | 56.5 | 21.1 | 8.0 | 3.8 | 2.8 | 2.4 |
| 289B6G6 | 601.0 | 597.2 | 466.1 | 178.7 | 47.2 | 14.1 | 5.3 | 3.0 |

EXAMPLE 5

Figure 10A:
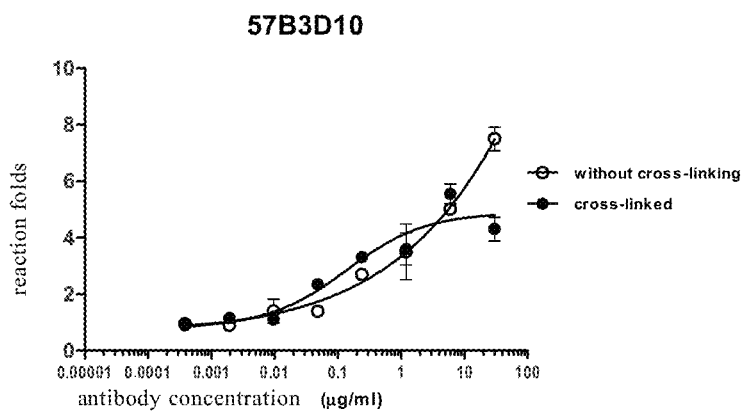
FIG. 10A and FIG. 10B show a reporter gene experiment in which each 4-1BB fully human antibody activates the NF-κB downstream promoter, respectively.
Figure 10B:
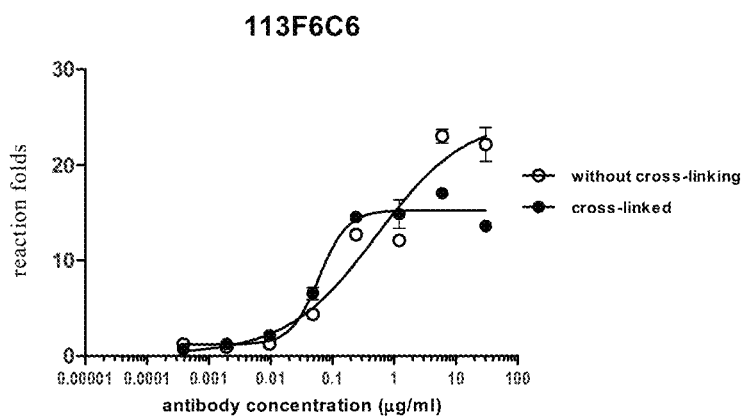

Detection of 4-1BB Antibody Activity in NFκB Luciferase Reporter Gene Experiment The human 4-1BB protein positive HEK293 stable cell line (see Example 1 for the preparation method) was further transfected with the NFκB luciferase reporter gene plasmid to prepare human 4-1BB protein positive NFκB luciferase reporter gene-stable cell lines. Anti-human or rat Fc F(ab')$_2$ was used to cross-link the antibody to be detected, and then the antibody with or without cross-linking was added to this stable cell line for cell culture. After 5 hours, luciferase detection reagent was added and the fluorescence value was read. The results are shown in FIGS. 10A-10B and Table 14. Table 14 shows that the fully human 4-1BB antibody strongly activates the NFκB signaling pathway downstream of the 4-1BB protein, and the antibody activation ability is further enhanced after the antibody is cross-linked (EC50 value decreases), indicating that when the 4-1BB antibody is used in vivo, it can be cross-linked through cell-mediated expression of FcR after reaching a specific area, such as tumor tissue, thereby enhancing antibody activity and safety. Table 14 shows the fluorescence multiples and EC50 values of the fully human 4-1BB antibody group relative to the control group (human IgG).

TABLE 14 activation of NFκB transcription factor downstream of 4-1BB protein by fully human 4-1BB antibody

| Clone number | | Fluorescence value antibody concentration (µg/ml) | | | | | | | | EC50 (nM) |
|---|---|---|---|---|---|---|---|---|---|---|
| | | 10 | 2 | 0.4 | 0.08 | 0.016 | 0.0032 | 0.00064 | 0.00013 | |
| 57B3D10 | Non-cross-linked group | 7.5 | 5 | 3.5 | 2.7 | 1.4 | 1.4 | 0.9 | 0.95 | — |
| | Cross-linking group | 4.3 | 5.55 | 3.6 | 3.3 | 2.35 | 1.1 | 1.15 | 0.9 | 0.94 |
| 113F6C6 | Non-cross-linked group | 22.15 | 23 | 12.1 | 12.7 | 4.35 | 1.3 | 0.95 | 1.25 | 3.46 |
| | Cross-linking group | 13.6 | 17.05 | 14.85 | 14.55 | 6.55 | 2.15 | 1.3 | 0.7 | 0.41 |

EXAMPLE 6

Detection of the Blocking of the Binding Between 4-1BB Protein and its Receptor 4-1BBL by 4-1BB Antibody CHO cells expressing 4-1BB protein were used to detect blocking of the binding between 4-1BB protein and its receptor 4-1BBL by 4-1BB antibody.

Figure 11:
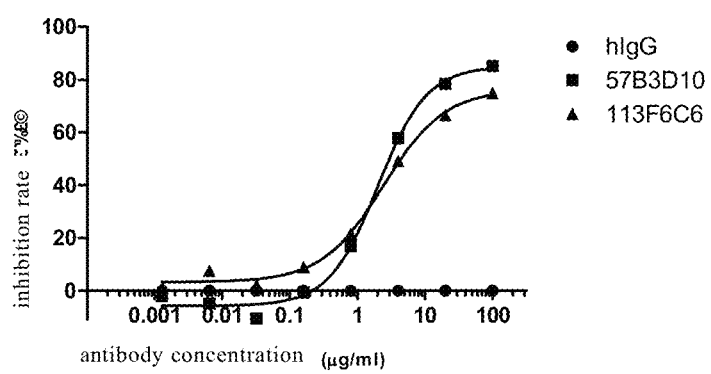
FIG. 11 shows that 4-1BB fully human antibody blocks the binding reaction of 4-1BB protein to its ligand 4-1BBL.

The CHOK1-h4-1BB cell line was treated according to Example 4 Part B to obtain $2 \times 10^6$ cells/mL of single-suspended cell, which was added to a 96-well FACS reaction plate at 100 µl per well, and 50 µl per well of the purified 4-1BB antibody test sample obtained in Example 3 was added, then 50 microliters of fusion protein his-muCD8a-4-1BBL$^{ECD}$ wad added (for manufacturing method see Example 1), and incubated on ice for 2 hours. It was washed twice by centrifugation with FACS buffer, 100 µl of anti-mouse CD8a fluorescent (Alexa 488) labeled secondary antibody was added to each well, and incubated on ice for 1 hour. It was washed three times with FACS buffer by centrifugation, and 100 µl of fixative [4% (v/v) paraformaldehyde] per well was added to suspend cells, and it was washed twice with FACS buffer by centrifugation after 10 minutes. The cells were suspended with 100 microliters of FACS buffer, and the results were detected and analyzed with FACS (FACS Calibur, purchased from BD). The results are shown in FIG. 11 and Table 15. Table 15 shows that the antibody to be tested can inhibit the binding of 4-1BB ligand protein to 4-1BB. The IgG control is human IgG, and the data in the table is the inhibition rate of the ligand binding by the fully human 4-1BB antibody relative to the control group (human IgG).

TABLE 15

Inhibition of the binding of 4-1BB protein to its receptor 4-1BBL by fully human 4-1BB antibody

| Clone number | Inhibition rate (%) antibody concentration (µg/ml) | | | | | | | |
|---|---|---|---|---|---|---|---|---|
| | 100 | 20 | 4 | 0.8 | 0.16 | 0.032 | 0.0064 | 0.00128 |
| 57B3D10 | 85.2 | 78.3 | 57.8 | 16.8 | −0.7 | −10.6 | −4.8 | −2.1 |
| 113F6C6 | 74.9 | 66.5 | 49.1 | 21.6 | 8.9 | 2.1 | 7.5 | 1.2 |

EXAMPLE 7

T Lymphocyte Stimulation Experiment (1) Ficoll Isolates Whole Blood to Obtain Peripheral Blood Mononuclear Lymphocyte PBMC.

Freshly obtained whole blood was diluted with phosphate buffered saline PBS at a volume ratio of 1:1 to obtain a diluted whole blood, and the diluted whole blood was gently spread on the Ficoll liquid surface (purchased from GE Healthcare) with a sterile pipette. The volume ratio of Ficoll to diluted whole blood was 3:4, avoiding shaking and mixing, and it was centrifuged at 400 g at room temperature and 20° C. gradient for 30 minutes. The centrifuge tube was divided into three layers, wherein the upper layer was a plasma, and the middle milky white layer was a mononuclear lymphocyte. A sterile pipette was used to gently aspirate the middle layer cell. It was collected into a new centrifuge tube, diluted with three times the volume of PBS phosphate buffer, centrifuged at 100 g for 10 minutes at room temperature, and the supernatant was discarded. The lymphocytes were resuspended to 10 mL with PBS phosphate buffer and the previous steps were repeated to remove the platelets. Finally, the lymphocytes were resuspended to 10 mL of a multi-component RPMI1640 medium (purchased from Invitrogen) containing 10% fetal bovine serum for use, that is, peripheral blood mononuclear lymphocyte PBMC, and the percentage was the mass percentage.

(2) T Lymphocyte Stimulation Experiment

Construction of CHOK1 cell line with anti-CD3 single chain antibody expressed on cell membrane: to make anti-CD3 (OKT3) (see Kipriyanov et al. 1997, PEDS 10:445-453) chimeric ScFv anchored on the cell membrane, the ScFv was linked to the 113-220 amino acid sequence of mouse CD8a (NCBI Accession No: NP-001074579.1) at C-terminal to construct plasmid pIRES-OS8. For the preparation method of plasmid pIRES-OS8, see Joe Sambrook, Molecular Cloning: A Laboratory Manual. The above plasmid pIRES-OS8 was transfected into CHOK1 cells, and the stable passage cell line CHOK1-OS8 was prepared according to the method of transfecting cells with plasmid as described in Example 1, and used as a T lymphocyte stimulating factor. At the same time, the purified 4-1BB antibody obtained in Example 2 to be tested diluted in equal volume ratio was prepared to obtain the sample solution to be tested.

Human CD3 positive T cells were purified from human peripheral blood mononuclear lymphocytes obtained in step (1) of Example 7 using a T cell purification kit (purchased from Stemcell) according to the method provided by the manufacturer. The CD3 positive T cells and the cell stimulating factor CHOK1-OS8 were added to the 96-well cell culture plate, and the antibody to be tested cross-linked with anti-human or rat Fc F(ab')$_2$ was added at the same time. Each reaction well had a final volume of 200 microliters. The supernatant was collected after co-cultivation at 37° C. in a 5% $CO_2$ incubator for 72 hours, and the resulting cell supernatant was frozen at −20° C., and the above percentage was a volume percentage.

(3) Enzyme-Linked Immunosorbent Assay Detection of Cytokine Gamma Interferon (IFN-γ) or Interleukin IL-2 in the Cell Supernatant.

The cytokine gamma interferon (IFN-γ) or interleukin IL-2 enzyme-linked immunosorbent assay in the cell supernatant were detected using R&D system related detection kits Human IFN-gamma Quantikin (DIF50) and Quantikine ELISA human IL-2 (S2050) following the instructions. All detection reagents except the detection antibody were provided by the detection kit.

The double-antibody sandwich ELISA kit (purchased from R&D Systems, IFN-γCat #DIF50 and IL-2 Cat #S2050) was used for the detection the content of cytokine gamma interferon (IFN-γ) or interleukin IL-2 in the cell supernatant. The experimental operation was strictly in accordance with the requirements of the kit instructions, and all detection reagents were provided by the kit. The specific experiment was briefly described as follows: IFN-γ or IL-2 polyclonal antibody was coated on the ELISA microplate, the cell supernatant obtained in step (2) of Example 5 was used as the test sample, and the standard and the sample to be tested were added and incubated for 2 hours at room temperature. 400 µl of washing solution was added to each well and the plate was washed for 4 times; horseradish peroxidase-labeled antibody against human IFN-γ or IL-2 was added, incubated at room temperature for 2 hours, and an immune complex was formed with IFN-γ or IL-2 on a microplate, and the microwells were washed; substrate was added to develop color, avoiding the light at room temperature for 30 minutes. Finally stop solution was added, and the absorbance of A450 nm was measured with a microplate reader.

Figure 12:
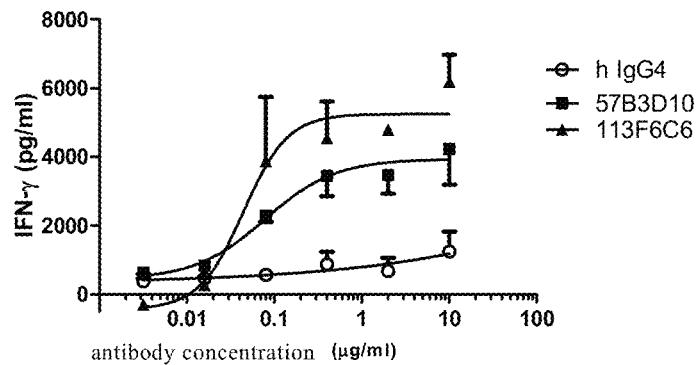
FIG. 12 shows the effect of 4-1BB fully human antibody on IFN-γ secretion in a T lymphocyte stimulation test.

The effect of antibodies on IFN-γ secretion in the T cell stimulation experiment was detected described in step (2) of Example 7. The results are shown in FIG. 12 and Table 16, Table 16 shows that the antibody to be tested in the PBMC lymphocyte stimulation test can increase the IFN-γ secretion of PBMC. The hIgG control is human IgG, and the data in the table is IFN-g value (pg/mL).

TABLE 16

The effect of 4-1BB fully human antibody on IFN-γ secretion in T cell stimulation test

| Clone number | IFN-γ antibody concentration (µg/mL) | | | | | |
|---|---|---|---|---|---|---|
| | 10 | 2 | 0.4 | 0.08 | 0.016 | 0.0032 |
| 57B3D10 | 4226.8 | 3472.0 | 3451.4 | 2280.7 | 832.4 | 621.6 |
| 113F6C6 | 6182.8 | 4787.6 | 4539.3 | 3872.0 | 270.5 | −300.8 |
| human IgG control | 1242.6 | 681.9 | 868.6 | 568.4 | 460.1 | 381.4 |

Figure 13:
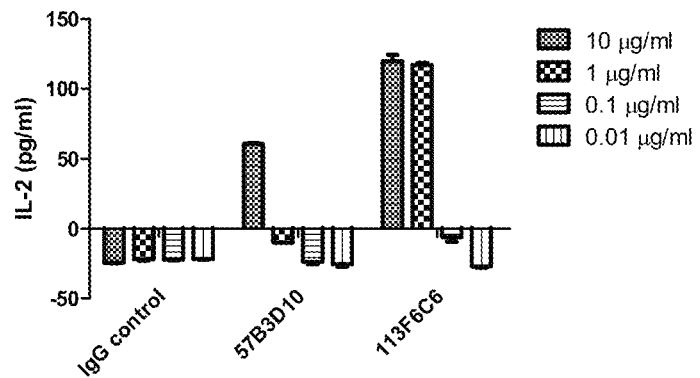
FIG. 13 shows the effect of 4-1BB fully human antibody on IL-2 secretion in a T lymphocyte stimulation test.

The effect of antibody on IL-2 secretion in the T cell stimulation experiment was detected described in step (2) of Example 7. Table 17 and FIG. 13 show that the fully humanized 4-1BB antibody can stimulate IL-2 secretion in the T cell stimulation test. The IgG control is human IgG (hIgG), and the data in the table is the IL-2 value (pg/mL).

TABLE 17

The effect of 4-1BB fully human antibody on IL-2 secretion in T cell test

| Clone number | IL-2 antibody concentration (µg/mL) | | | |
|---|---|---|---|---|
| | 10 | 1 | 0.1 | 0.01 |
| 57B3D10 | 60.8 | −9.9 | −23.7 | −25.3 |
| 113F6C6 | 119.7 | 117.1 | −6.0 | −26.9 |
| human IgG control | −24.4 | −22.0 | −22.2 | −21.6 |

EXAMPLE 8

Analysis and Determination on the Affinity of Anti-4-1BB Antibody

The Biacore T200 instrument (purchased) was used to determine the affinity constant. The specific operation and method were based on the instrument manual and the detailed method provided by the manufacturer. Sensors labeled with anti-human Fc were combined with anti-4-1BB fully human antibodies to detect the binding and dissociation of five different gradients of his-tagged human 4-1BB protein antigen. Then software was used to fit the dissociation constant and the binding constant. The affinity constant is the ratio of the dissociation constant and the binding constant. The results of the affinity test are shown in Table 18.

TABLE 18 affinity constants of 4-1BB antibodies to human 4-1BB

| Clone number | Affinity constant KD(nM) | Binding constant Ka(1/Ms) | Dissociation constant Kd(1/s) |
|---|---|---|---|
| 57B3D10 | 2.15E−08 | 5.74E+05 | 1.24E−02 |
| 113F6C6 | 1.76E−08 | 1.68E+06 | 3.00E−02 |

EXAMPLE 9

Evaluation on Anti-Tumor Activity of Anti-4-1BB Antibody Mice In Vivo

Using a MC38 homologous mouse model, the anti-tumor activity of the antibody in mice was evaluated using C57BL/6 mice knocked in by the human 4-1BB gene. The experimental design was as follows:

C57BL/6 mice with human 4-1BB gene knock-in were selected and divided into 4 groups, 6 mice per group. Utomilumab, Urelumab and isotype antibody hIgG4 were used as controls. The administration sample was 113F6C6 antibody. The route of administration was intraperitoneal injection, and the dose was 3 mg/kg (hIgG control), 1 mg/kg (Utomilumab, Urelumab and 113F6C6). Intraperitoneal injection was performed on day 0, 4, 7, 11, 14, 18, measured twice a week, measuring tumor volume, mouse body weight and mouse survival rate. Calculation formula for tumor volume was $½*L_{long}*L_{short}^2$.

Figure 15:
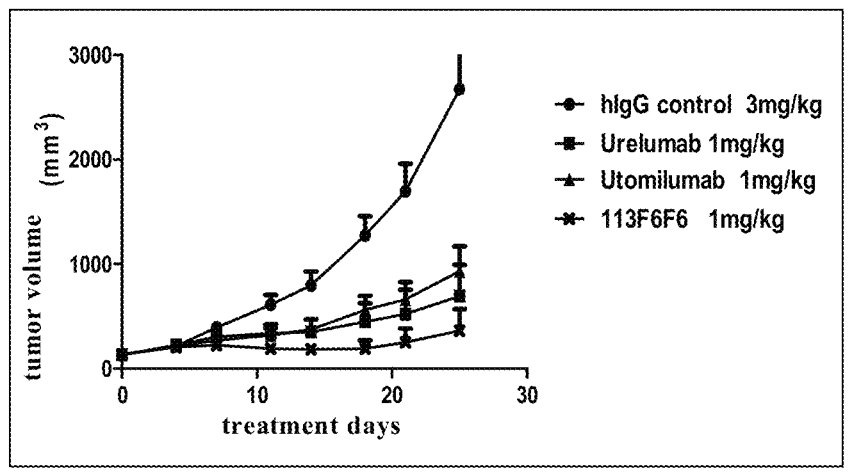
FIG. 15 shows an experimental result of 4-1BB antibody on mouse MC38 tumor growth.
Figure 16:
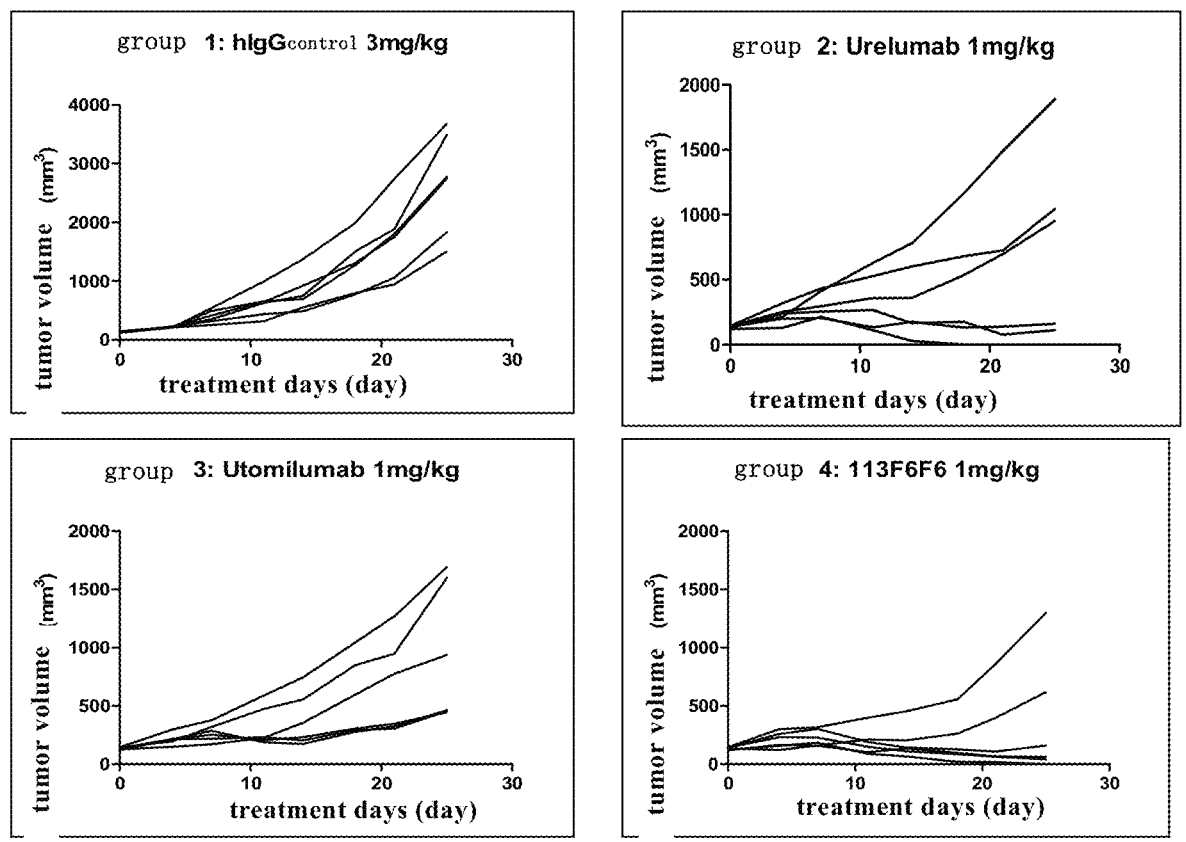
FIG. 16 shows the tumor volumes of individual mice in different antibody treatment groups.

The results are shown in Table 20 and FIGS. 15 and 16. The antibody of the present invention (113F6C6) can significantly inhibit tumor growth, and the inhibitory effect is significantly better than the control antibodies Utomilumab and Urelumab.

TABLE 20

Summary of growth inhibition of mouse MC38 tumor by 4-1BB antibody summary of MC38 tumor growth inhibition

| | Antibody name | | |
|---|---|---|---|
| | 113F6F6 | Utomilumab | Urelumab |
| Dosage (mg/kg) | 1 | 1 | 1 |
| TGI % | 90.98 | 68.61 | 78.01 |
| CR | 2(6) | 0(6) | 1(6) |

COMPARATIVE EXAMPLE

The Pfizer Utomilumab antibody (PF-05082566), which was the same as the antibody target of this application was used as a comparison antibody to conduct a comparative test, and the test method was completely the same as that in Example 7.

Figure 14:
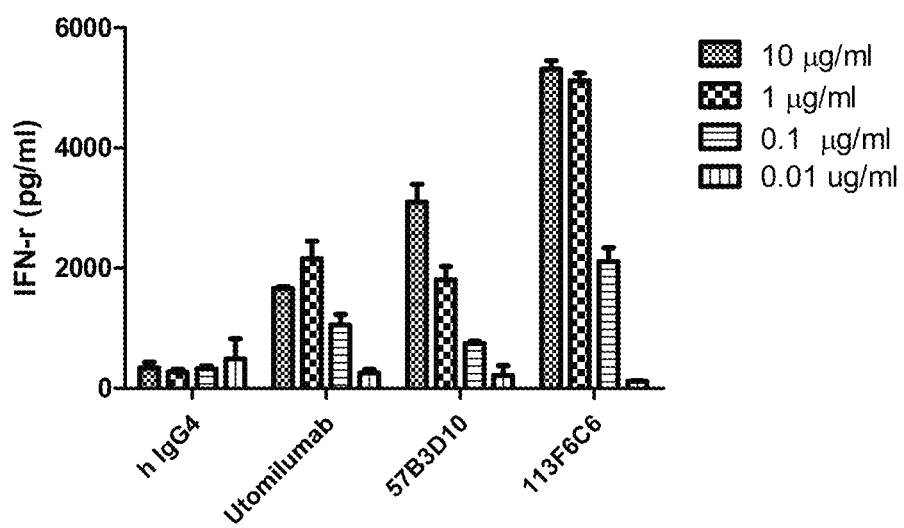
FIG. 14 shows the results of a comparative test using Pfizer's Utomilumab antibody as a comparative antibody.

The results are shown in FIG. 14 and Table 19. Compared with Utomilumab, the 4-1BB antibody of the present application can stimulate T cells to secrete more IFN-γ cytokines and have stronger activation of T cells.

TABLE 19

Effect of antibodies on IFN-γ secretion in T cell stimulation test

| Clone number | IFN-γ antibody concentration (µg/mL) | | | |
|---|---|---|---|---|
| | 10 | 1 | 0.1 | 0.01 |
| Utomilumab | 1664.6 | 2159.1 | 1053.2 | 258.65 |
| 57B3D10 | 3103.4 | 1805.8 | 749.4 | 214.2 |
| 113F6C6 | 5315.2 | 5115.9 | 2106.2 | 115.45 |
| human IgG control | 344.8 | 273.4 | 322.05 | 493.85 |

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. An anti-4-1BB antibody comprising:
   (1) a heavy chain variable region comprising the following three complementary determining regions (CDRs):
   CDR1 having the amino acid sequence as set forth in SEQ ID NO: 2;
   CDR2 having the amino acid sequence as set forth in SEQ ID NO: 3;
   CDR3 having the amino acid sequence as set forth in SEQ ID NO: 4; and
   (2) a light chain variable region comprising the following three complementary determining regions (CDRs):
   CDR1' having the amino acid sequence as set forth in SEQ ID NO: 6
   CDR2' having the amino acid sequence as set forth in SEQ ID NO: 7; and
   CDR3' having the amino acid sequence as set forth in SEQ ID NO: 8.

2. An anti-4-1BB antibody comprising:
   (1) a heavy chain variable region comprising the following three complementary determining regions (CDRs):
   CDR1 having the amino acid sequence as set forth in SEQ ID NO: 10;
   CDR2 having the amino acid sequence as set forth in SEQ ID NO: 11;
   CDR3 having the amino acid sequence as set forth in SEQ ID NO: 12; and
   (2) a light chain variable region comprising the following three complementary determining regions (CDRs):
   CDR1' having the amino acid sequence as set forth in SEQ ID NO: 14,
   CDR2' having the amino acid sequence as set forth in SEQ ID NO: 15, and
   CDR3' having the amino acid sequence as set forth in SEQ ID NO: 16.

3. An anti-4-1BB antibody selected from:
   (1) an anti-4-1BB antibody having a heavy chain variable region having the amino acid sequence as set forth in SEQ ID NO: 1 and a light chain variable region having the amino acid sequence as set forth in SEQ ID NO: 5; and
   (2) an anti-4-1BB antibody having a heavy chain variable region having the amino acid sequence as set forth in SEQ ID NO: 9 and a light chain variable region having the amino acid sequence as set forth in SEQ ID NO: 13.

4. A recombinant protein comprising:
   (i) the anti-4-1BB antibody of claim 1; and
   (ii) a tag sequence to facilitate expression or purification.

5. A recombinant protein comprising:
   (i) the anti-4-1BB antibody of claim 2; and
   (ii) a tag sequence to facilitate expression or purification.

6. The anti-4-1 BB antibody of claim 1, wherein the antibody is a fully human antibody.

7. The anti-4-1 BB antibody of claim 2, wherein the antibody is a fully human antibody.

8. A method for treating a 4-1BB related cancer, wherein the method comprises administering to a subject in need thereof an active ingredient comprising the anti-4-1BB antibody of claim 1.

9. A method for treating a 4-1BB related cancer, wherein the method comprises administering to a subject in need thereof an active ingredient comprising the anti-4-1 BB antibody of claim 2.

10. A method for treating a 4-1 BB related cancer, wherein the method comprises administering to a subject in need thereof an active ingredient comprising the anti-4-1 BB antibody of claim 3.

11. A method for treating a 4-1 BB related cancer, wherein the method comprises administering to a subject in need thereof an active ingredient comprising the recombinant protein of claim 4.

12. A method for treating a 4-1 BB related cancer, wherein the method comprises administering to a subject in need thereof an active ingredient comprising the recombinant protein of claim 5.

* * * * *